(12) United States Patent
Waterson et al.

(10) Patent No.: US 6,313,127 B1
(45) Date of Patent: Nov. 6, 2001

(54) HETEROCYCLIC COMPOUNDS USEFUL AS PHARMACEUTICAL AGENTS

(75) Inventors: David Waterson; Elaine Sophie Elizabeth Stokes; George Robert Brown; John Graham Cumming; Nicholas John Newcombe; Robin Wood; William John Watkins, all of Macclesfield (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/117,523

(22) PCT Filed: Jan. 31, 1997

(86) PCT No.: PCT/GB97/00282

§ 371 Date: Jul. 31, 1998

§ 102(e) Date: Jul. 31, 1998

(87) PCT Pub. No.: WO97/28128

PCT Pub. Date: Aug. 7, 1997

(30) Foreign Application Priority Data

Feb. 2, 1996 (GB) .................................................. 9602156
Feb. 2, 1996 (GB) .................................................. 9602157

(51) Int. Cl.[7] ...................... A61K 31/496; C07D 401/04
(52) U.S. Cl. ................................ 514/253.01; 514/252.18; 514/340; 514/341; 544/295; 544/360; 546/268.1; 546/274.1
(58) Field of Search .................... 514/219, 318, 514/332, 333; 544/354; 546/193, 194, 255, 256

(56) References Cited

U.S. PATENT DOCUMENTS

| | | | |
|---|---|---|---|
| 4,167,567 | 9/1979 | McCall | 424/250 |
| 4,231,938 | 11/1980 | Monaghan et al. | 260/343.5 |
| 4,537,896 | 8/1985 | Claeson et al. | 514/330 |

(List continued on next page.)

FOREIGN PATENT DOCUMENTS

| | | |
|---|---|---|
| 10177/92 | 7/1992 | (AU) . |
| 39 05 364 A1 | 8/1990 | (DE) . |
| 39 43 225 A | 6/1991 | (DE) . |
| 42 43 858 A1 | 6/1994 | (DE) . |
| 43 06 506 A1 | 9/1994 | (DE) . |
| 0 097 630 A2 | 1/1984 | (EP) . |
| 0 232 740 A1 | 8/1987 | (EP) . |
| 0 233 051 A2 | 8/1987 | (EP) . |
| 0 244 115 | 11/1987 | (EP) . |
| 0 244 155 A1 | 11/1987 | (EP) . |
| 0 308 337 | 3/1989 | (EP) . |
| 0 324 421 A2 | 7/1989 | (EP) . |
| 0 352 946 A1 | 1/1990 | (EP) . |
| 0 359 389 | 3/1990 | (EP) . |
| 0 409 413 | 1/1991 | (EP) . |
| 0 495 750 | 7/1992 | (EP) . |
| 0 515 240 A1 | 11/1992 | (EP) . |
| 0 519 449 A1 | 12/1992 | (EP) . |
| 0 555 824 A1 | 8/1993 | (EP) . |
| 0 576 941 A1 | 1/1994 | (EP) . |
| 0 608 759 A2 | 8/1994 | (EP) . |
| 2 697 252 A1 | 4/1994 | (FR) . |
| 1 449 100 | 9/1976 | (GB) . |
| WO 92/08709 | 5/1992 | (WO) . |
| WO 92/18478 | 10/1992 | (WO) . |
| WO 93/06085 | 4/1993 | (WO) . |
| WO 94/18185 | 8/1994 | (WO) . |
| WO 94/20467 | 9/1994 | (WO) . |
| WO 94/20468 | 9/1994 | (WO) . |
| WO 94 22835 | 10/1994 | (WO) . |
| WO 96/05189 | 2/1996 | (WO) . |
| WO 96 10022 | 4/1996 | (WO) . |
| WO 96/26196 | 8/1996 | (WO) . |
| WO 96/30343 | 10/1996 | (WO) . |
| WO 96/33171 | 10/1996 | (WO) . |
| WO 97 06802 | 2/1997 | (WO) . |
| WO 97/28128 | 8/1997 | (WO) . |
| WO 97/28129 | 8/1997 | (WO) . |
| WO 97/29104 | 8/1997 | (WO) . |
| WO 97/30971 | 8/1997 | (WO) . |
| WO 98/06705 | 2/1998 | (WO) . |
| WO 98/21188 | 5/1998 | (WO) . |

OTHER PUBLICATIONS

O. Mitsunobu et al., "Preparation of Carboxylic Esters and Phosphoric Esters by the Activation of Alcohols", Bull. Chem. Soc. Jpn., 44(12):3427–3430 (1971).

M.M. Bowers Nemia et al., "Synthetic Routes to 3–Pyrrolidinol", Synth. Comm., 13(13):1117–1123 (1983).

T. Kato et al., "Studies on ketene and Its Derivatives. LXXVI.[1]) REactions of Acetoacetamide and B–Aminocrotonamide with B–Diketone, B–Ketoaldehyde and Related Compounds", Chem. Pharm. Bull., 24(2):303–309 (1976).

T. Kato et al., "Reactivities of 4–Chloropyridine Derivatives and Their 1–Oxides", Chem. Pharm. Bull., 15:1343–1348 (1967).

Conway et al., "Approaches to the Generation of 2,3–Indolyne"; Heterocycles, 1992, 34(11) 2095–2108.

Hinbio et al.; "N–Phenylsulfonylindole derivatives", Chemical Abstracts, 118: 147461, Apr. 1993.

(List continued on next page.)

Primary Examiner—Richard L. Raymond
(74) Attorney, Agent, or Firm—Pillsbury Winthrop LLP

(57) ABSTRACT

Compounds of formula (I)

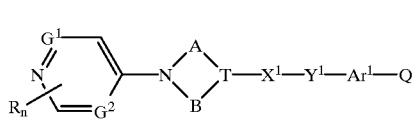

in which all variables are defined in the description and their salts inhibit the enzyme oxido squalene cyclase and are useful in treating hypercholesterolemia and also as antifungal agents. Processes for their preparation are also described together with their use in medicine.

17 Claims, No Drawings

U.S. PATENT DOCUMENTS

| | | | |
|---|---|---|---|
| 4,564,610 | | 1/1986 | Rahtz et al. ............ 428/246 |
| 4,629,728 | * | 12/1986 | Regnier et al. ............ 514/252 |
| 4,788,196 | | 11/1988 | Cross et al. ............ 514/252 |
| 4,806,536 | * | 2/1989 | Cross et al. ............ 514/252 |
| 4,835,165 | * | 5/1989 | Cross et al. ............ 514/318 |
| 4,840,963 | | 6/1989 | Shepard et al. ............ 514/418 |
| 4,968,704 | * | 11/1990 | Cross et al. ............ 514/318 |
| 5,032,604 | * | 7/1991 | Baldwin et al. ............ 514/361 |
| 5,138,058 | | 8/1992 | Geisen et al. ............ 544/295 |
| 5,254,563 | | 10/1993 | Huth et al. ............ 514/292 |
| 5,332,822 | | 7/1994 | Misra ............ 546/164 |
| 5,364,865 | * | 11/1994 | Diana ............ 514/318 |
| 5,371,091 | | 12/1994 | Misra et al. ............ 514/314 |
| 5,411,971 | | 5/1995 | Emonds-Alt et al. ............ 514/318 |
| 5,556,977 | * | 9/1996 | Wayne et al. ............ 544/360 |
| 5,563,141 | * | 10/1996 | Wayne et al. ............ 514/252 |
| 5,580,881 | | 12/1996 | Binet ............ 514/307 |
| 5,606,065 | | 2/1997 | Emonds-Alt et al. ............ 546/223 |
| 5,681,954 | * | 10/1997 | Yamamoto et al. ............ 544/114 |
| 5,795,893 | * | 8/1998 | Bondinell et al. ............ 514/252 |
| 5,856,326 | | 5/1999 | Anthony et al. ............ 514/252 |
| 6,022,869 | | 2/2000 | Faull ............ 514/227.8 |
| 6,037,343 | * | 3/2000 | Ali ............ 514/252 |

OTHER PUBLICATIONS

Kataoka et al., Chemical Abstracts, vol. 123, No. 14, Oct. 2, 1995 Columbus, Ohio, US; abstract No. 179521d, "Homopiperazines as cell migration inhibitors."Xp002081582 see abstract & JP 95 145060 A (TEJIN LTD).

Sundberg et al. "Synthesis with N–Protected 2–Lithioindoles"; J. Org. Chem., 1973 38(19) 3324–3330.

Von G.Krüger, et al.; (Thomae et al.) Arzneim–Fosch., Synthesen von N–Benzyl–aminocarbonsäuren und thren Derivaten; (Synthesis and N–benzylaminocarboxylic acids and their derivatives), vol. 23(2a), pp. 290–295 (1973).

Yokoyama et al. "Palladium–catalyzed cross–coupling reaction: direct allylation of aryl bromides with ally acetate" Tetrahedron Letters., vol. 26, No. 52–(1985) pp. 6457–6460, XP002081581 Oxford GB * p. 6458–6459: Compound 7.

Zaoral et al., "Amino acids and peptides, LIX. Synthesis and some biological properties of L–DABB–vasopressin", Collect. Czech. Chem. Commun., vol. 31, 1966, pp. 90–95, XP002081879 see compound 11, p. 95.

Budavari: Merck Index, vol. 11 Ed., 1989, See Monograph numbers 804 and 2807.

Cattel et al: "Drug design based on biosynthetic studies: synthesis, biological activity, and kinetics of new inhibitors of 2,3–oxidosualene cyclase and squalene epoxidase.", Steroids., vol. 53, No. 3–5, 1989, pp. 363–391, XP000611661.

Chambers et al., "Preparation of arylpyridine compounds for treating leukotriene–related diseases", Chemical Abstracts, Abstract No. 139113, vol. 119 (1993).

Cross et al., "Preparation of N–[(heterocyclicylmethoyx-)phenyl] sulfamides and analogs as antiarrhythmics", Chemical Abstracts, Abstract No. 231211, Vol. 113 (1989).

E. Jucker, "Über C–substituierte Piperazinderativate", Helv. Chim. Acta., 45:2383–2042 (1962).

Kettner et al., "The Selective Inhibition of Thrombin by Peptides of Boroarginine", The Journal of Biological Chemistry, vol. 265, No. 30, pp. 18289–18297 (1990).

Sartori et al., "Synthesis and analgesic activities of urea derivatives of α–amino–N–pyridyl benzene propanamide", Eur. J. Med Chem (1994), 431–439.

Smith et al., "Fibrin, Red Cell and Platelet Interactions in an Experimental Model of Thrombosis", Br. J. Pharmac., vol. 77, pp. 29–38 (1982).

Szmant et al., "Concerning the Variable Character of the Sulfone Group", J. Amer. Chem. Soc., vol. 78, pp. 3400–3403 (1956).

Tabacik et al: "Squalene expoxidase, oxideo–squalene cyclase and cholesterol bio synthesis in normal and tumoral mucosa of the human gastrointestinal tract. Evidence of post–HMGCoA regulation.", Biochim. Biophys. Acta, vol. 666, No. 3, 1982, pp. 433–441, XP000610864.

Vigroux e tal., "Cyclization–Activated Prodrugs: N–(Substituted 2–hydroxyphenyl and 2–hydroxypropyl)carbamates Based on Ring–Opened Derivatives of Active Benzoxazolones and Oxazolidones as Mutual Prodrugs of Acetamiophen", J. Med. Chem. vol. 38, pp. 3983–3994 (1995).

Vogel et al., "Comparison of Two Experimental Thrombosis Models in Rats Effects of Four Glycosaminoglycans", Thrombosis Research, vol. 54, No. 5, pp. 399–410 (1989).

Wallis, "Inhibitors of Coagulation Factor Xa: From Macromolecular Beginnings to Small Molecules", Current Opinion in Therapeutic Patents, Aug. 1993, pp. 1173–1179.

Deratani et al. (Polymer, 28(5), 825–830, (1987).*

Prasad et al. (Curr. Sci., 53(15), 778–781), (1984).*

Saxena et al. (Indian J. Chem. Sect. B, 19b(10), 873–878), (1980).*

Sato et al. (Yakugaku Zasshi, 98(3), 335–348), (1978).*

Jain et al. (J. Med. Chem., 10(5), 812–818), (1967).*

Ratouis et al. (J. Med. Chem., 8, 104–107), (1965).*

Boissier et al. (J. Med. Chem., 6, 541–544), (1963).*

* cited by examiner

HETEROCYCLIC COMPOUNDS USEFUL AS PHARMACEUTICAL AGENTS

This application is a 371 of PCT/GB97/00282, filed Jan. 31, 1997.

This invention concerns heterocyclic compounds which are useful in inhibiting oxido-squalene cyclase, processes for their preparation and pharmaceutical compositions containing them. The present invention is also concerned with heterocyclic compounds capable of inhibiting cholesterol biosynthesis and hence in lowering cholesterol levels in blood plasma. The present invention also relates to methods of using such heterocyclic compounds in diseases and medical conditions such as hypercholesterolemia and atherosclerosis.

There is clinical evidence that raised serum cholesterol levels increase the risk of coronary heart disease and associated diseases such as atherosclerosis and ischaemic heart disease. As a result there has been a great deal of interest in finding ways of lowering cholesterol levels in blood plasma. Although it has been possible to obtain some reduction by means of diet, only modest reductions have been obtained by controlling the dietry intake of cholesterol. Consequently, there is a need for therapeutic approaches to reducing cholesterol levels.

Several different classes of compounds have been reported to possess the capability of being able to lower cholesterol levels in blood plasma. For example agents which inhibit the enzyme HMGCoA reductase, which is essential for the production of cholesterol, have been reported to reduce levels of serum cholesterol. Illustrative of this class of compounds is the HMGCoA reductase inhibitor known as lovastatin which is disclosed in U.S. Pat. No. 4,231,938. Other agents which are reported to lower serum cholesterol include those which act by complexing with bile acids in the intestinal system and which are hence termed "bile acid sequestrants". It is believed that many of such agents act by sequestering bile acids within the intestinal tract. This results in a lowering of the levels of bile acid circulating in the enteroheptatic system and promotes replacement of bile acids by synthesis in the liver from cholesterol, which results in an upregulation of the hepatic LDL cholesterol receptor and in a lowering of circulating blood cholesterol levels.

The biosynthesis of cholesterol is a complex process which will be considered here as three principal stages, namely 1) the conversion of acetic acid to mevalonic acid 2) the conversion of mevalonic acid to squalene and 3) the conversion of squalene to cholesterol. In the last stage, squalene is first converted into 2,3-oxido-squalene and then to lanosterol. Lanosterol is then converted to cholesterol through a number of enzymatic steps.

The conversion of 2,3-oxido-squalene to lanosterol is a key step in the biosynthesis of cholesterol. This conversion is catalysed by the enzyme oxido-squalene cyclase. It follows that inhibition of this enzyme decreases the amount of lanosterol available for conversion to cholesterol. Consequently, inhibition of oxido-squalene cyclase should interupt cholesterol biosynthesis and give rise to a lowering of cholesterol levels in blood plasma via LDL receptor upregulation.

The present invention is based on the discovery that certain heterocyclic compounds are inhibitors of oxido-squalene cyclase and are hence useful in treating diseases and medical conditions in which inhibition of oxido-squalene cyclase is desirable.

According to the present invention there is provided a compound of formula I, or a pharmaceutically acceptable salt thereof, wherein According to the present invention there is provided a compound of formula I,

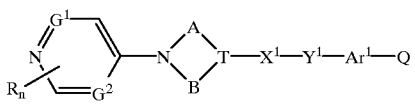

wherein
$G^1$ is CH or N;
$G^2$ is CH or N;
n is 1 or 2;
R is hydrogen, halogeno, trifluoromethyl, trifluoromethoxy, cyano, amino, hydroxy, nitro, (1–4C)alkyl, (1–4C)alkoxy, (1–4C)alkylamino, di(1–4C)alkylarnino or phenyl(1–4C)alkyl;
A is methylene or ethylene; B is ethylene; and wherein A and B may independently optionally bear a substituent selected from (1–6C)alkyl, (1–6C)alkoxy, phenyl (1–4C)alkyl, halogeno and (1–6C)alkoxycarbonyl;
T is CH or N;
when T is CH, $X^1$ is selected from $CR^1R^2$, $SO_2$, SO, CO, $CR^3R^4O$, a bond, O, S and $NR^5$; and when T is N, $X^1$ is selected from $CR^1R^2$, $SO_2$, SO, CO, $CR^3R^4O$ and a bond; wherein $R^1$, $R^2$, $R^3$, $R^4$ and $R^5$ are independently selected from hydrogen and (1–4C)alkyl;
$Y^1$ represents $CR^6R^7$ or a bond, wherein $R^6$ and $R^7$ are independently selected from hydrogen and (1–4C) alkyl;
$Ar^1$ is a phenylene, naphthylene, a 5- or 6-membered monocyclic heteroaryl ring containing 1, 2 or 3 heteroatoms selected from nitrogen, oxygen and sulphur, or a 9- or 10-membered bicyclic heteroaryl ring containing 1, 2 or 3 heteroatoms selected from nitrogen, oxygen and sulphur;
Q is selected from hydrogen and a group of formula $L^1X^2L^2Z$ in which $L^1$ is a bond, (1–4C)alkylene or (2–4C)alkenylene, $L^2$ is a bond or (1–4C)alkylene, $X^2$ is a bond, O, S, SO, $SO_2$, $CR^8R^9$, CO, $OSO_2$, $OCR^8R^9$, OCO, $SO_2O$, $CR^8(R^9)O$, COO, $NR^{10}SO_2$, $SO_2NR^{11}$, $NR^{12}CO$, $CONR^{12}$, $NR^{13}CONR^{14}$ and $NR^{14}$ in which $R^8$ and $R^9$ are independently selected from hydrogen, hydroxy and (1–4C)alkyl; and $R^{10}$, $R^{11}$, $R^{12}$, $R^{13}$ and $R^{14}$ are independently selected from hydrogen and (1–4C)alkyl;
Z is hydrogen, (1–4C)alkyl, phenyl, naphthyl, phenyl (2–4C)alkenyl, phenyl(2–4C)alkynyl or a heterocyclic moiety containing 1, 2, 3 or 4 heteroatoms selected from nitrogen, oxygen and sulphur;
and wherein the phenyl, naphthyl or heteroaryl moiety in $Ar^1$ and the alkyl, phenyl, naphthyl, or heterocyclic moiety in Z may optionally bear one or more substituents selected from halogeno, hydroxy, oxy, amino, nitro, cyano, carboxy, carbamoyl, (1–6C)alkyl, (2–6C) alkenyl, (2–6C)alkynyl, hydroxy(1–6C)alkyl, (1–6C) alkoxy, (3–6C)cycloalkyl, (3–6C)cycloalkyl(1–4C) alkyl, (1–4C)alkylenedioxy, (1–6C)alkylamino, di-[(1–6C)alkyl]amino, N-(1–6C)alkylcarbamoyl, di-N [(1–6C)alkyl]carbamoyl, (1–6C)alkanoylamino, (1–6C)alkoxycarbonyl, (1–6C)alkylthio, (1–6C) alkylsulphinyl, (1–6C)alkylsulphonyl, halogeno(1–6C) alkyl, halogeno(1–6C) alkylthio, halogeno(1–6C) alkoxy, (1–6C)alkanoyl, tetrazoyl, phenyl, phenoxy, phenylsulphonyl, piperidinocarbonyl, morpholinocarbonyl, hydroxy(1–6C)alkyl and amino (1–6C)alkyl; wherein any phenyl containing substituents may optionally bear one or more substituents selected from halogeno, trifluoromethyl, trifluoromethoxy, cyano, amino, hydroxy, nitro, (1–4C) alkyl, (1–4C)alkoxy, (1–4C)alkylamino and di(1–4C) alkylamino;

provided that the compound is not N-[4-[4-(4-pyridyl) piperazin-1-ylcarbonyl]phenyl]-(E)-4-chlorostyrenesulphonamide or N-[4-[4-(4-pyridyl) piperazin-1-ylcarbonyl]phenyl]4'-bromio-4-biplhenylesulphonamide;

and pharmaceutically acceptable salts thereof.

The chemical formulae referred to herein by Roman numerals are, for convenience, set out on a separate sheet following the Examples.

It will be understood that when formula I compounds contain a chiral centre, the compounds of the invention may exist in, and be isolated in, optically active or racemic form. The invention includes any optically active or racemic form of a compound of formula I which possesses the beneficial pharmacological effect of inhibiting oxido-squalene cyclase. The synthesis of optically active forms may be carried out by standard techniques of organic chemistry well known in the art, for example by, resolution of a racemic form, by synthesis from optically active starting materials or by asymmetric synthesis. It will also be appreciated that certain compounds of formula I may exist as geometrical isomers. The invention includes any geometrical isomer of a compound of formula I which possesses the beneficial pharmacological effect of inhibiting oxido-squalene cyclase.

It will also be understood that certain compounds of the present invention may exist in solvated, for example hydrated, as well as unsolvated forms. It is to be understood that the present invention encompasses all such solvated forms which possess the property of inhibiting oxido-squalene cyclase.

It is also to be understood that generic terms such as "alkyl" include both the straight chain and branched chain groups such as butyl and tert-butyl. However, when a specific term such as "butyl" is used, it is specific for the straight chain or "normal" butyl group, branched chain isomers such as "t-butyl" being referred to specifically when intended.

In one embodiment of the present invention there is provided a compound of formula I, or a pharmaceutically acceptable salt thereof, as herein before defined, provided that when $X^1$ is CO, $Ar^1$ is phenylene which optionally bears 1 or 2 substituents selected from halogeno, trifluoromethyl, (1–4C)alkyl and (1–4C)alkoxy, and $L^2$ is a bond to Q, then $X^2$ is a bond.

Particular values for optional substituents which may be present on a phenyl, napthyl, heteroaryl or heterocyclic moiety include, for example, for alkyl; (1–4C)alkyl, such as methyl, ethyl, propyl, isopropyl, butyl, isobutyl, sec-butyl or tert-butyl;

for cycloalkyl cyclopropyl, cyclobutyl or cyclopentyl;

for cycloalklalkyl (3–6C)cycloalkyl(1–2C)alkyl such as cyclopropylmethyl, cyclopropylethyl, cyclobutylmethyl or cyclopentylmethyl;

for alkenyl; (2–4C)alkenyl, such as allyl, prop-1-enyl, 2-methyl-2-propenyl or 2-butenyl;

for alkynyl; (2–4C)alkynyl, such as prop-2-ynyl or but-2-ynyl;

for alkoxy; (1–6C)alkoxy, such as methoxy, ethoxy, propoxy, isopropoxy, butoxy, pentoxy or 3-methylbutoxy;

for alkylarnino; (1–4C)alkylamino, such as methylamino, ethylamino, propylamino or butylamino;

for di-alkylamino; di-[(1–4C)alkyl]amino such as dimethylamino, diethylamino, methylpropylamino or dipropylamino;

for alkylcarbamoyl; (1–4C)alkylcarbamoyl such as N-methylcarbamoyl, N-ethylcarbamoyl, N-propylcarbamoyl, N-butylcarbamoyl or N-tert-butylcarbamoyl or (N-(2-methylpropyl)carbamoyl;

for di-alkylcarbamoyl; di-[(1–4C)alkyl]carbamoyl, such as N,N-dimethylcarbamoyl or N,N-diethylcarbamoyl;

for alkoxycarbonyl; (1–4C)alkoxycarbamoyl such as methoxycarbonyl, ethoxycarbonyl, propoxycarbonyl, iso-propoxycarbonyl, butoxycarbonyl or tert-butoxycarbonyl;

for alkylthio; (1–4C)alkylthio such as methylthio, ethylthio, propylthio, isopropylthio or butylthio;

for alkylsulphinyl; (1–4C)alkylsulphinyl such as methylsulphinyl, ethylsulphinyl, propylsulphinyl, isopropylsulphinyl or butylsulphinyl;

for alkylsulphonyl; (1–4C)alkylsulphonyl such as methylsulphonyl, ethylsulphonyl, propylsulphonyl, isoproylsulphonyl or butylsulphonyl;

for halogeno; fluoro, chloro, bromo or iodo;

for halogenoalkyl; halogeno(1–4C)alkyl such as halogenoalkyl containing one, two or three halo groups selected from fluoro, chloro, bromo and iodo and an alkyl group selected from methyl, ethyl, propyl, iso-propyl, butyl, iso-butyl and sec-butyl, thus particular values will include trifluoromethyl, difluoromethyl and fluoromethyl;

for alkanoylamino; (1–4C)alkanoylamino such as formamido, acetamido, propionamido, iso-propionamido, butyramido or iso-butyramido;

for alkylenedixoy; methylenedioxy or ethylenedioxy;

for alkanoyl; (1–4C)alkanoyl such as formyl, acetyl, propionyl or butyryl;

for hydroxyalkyl 1-hydroxy-1-methylethyl, hydroxymethyl, 2-hydroxyethyl, or 2-hydroxypropyl;

for aminoalkyl; aminomethyl, 2-aminoethyl, 1-aminoethyl or aminopropyl.

Particular values for optional substituents on A and B include, for example:

for alkyl; (1–4C)alkyl such as methyl, ethyl, propyl, isopropyl, butyl, isobutyl, sec-butyl or tert-butyl;

for alkoxy; (1–4C)alkoxy such as methoxy, ethoxy, propoxy, isopropoxy or butoxy;

for phenylalkyl; phenyl (1–2C)alkyl such as benzyl, 2-phenylethyl or 1-phenylethyl for halogeno; fluoro, chloro, bromo or iodo for alkoxycarbonyl; methoxycarbonyl, ethoxycarbonyl, isopropoxycarbonyl or butoxycarbonyl;

Particular values for R include, for example, for alkyl; methyl, ethyl, propyl, iso-propyl or tert-butyl;

for alkoxy methoxy, ethoxy, propoxy, isopropoxy or butoxy;

for alkylamino methylamino, ethylamino or propylamino;

for di-alkylamino dimethylamino, N-ethyl-N-methylamino or diethylamino;

for halogeno fluoro, chloro, bromo or iodo.

A particular value for R when trifluoromethyl is 3-trifluoromethyl and/or 5-trifluoromethyl. A further particular value for R is hydrogen, also (1–2C) alkyl, for example 2-methyl.

A particular value for $Ar^1$ when it is a 5- or 6-membered heteroaryl ring is, for example, furandiyl, thiopheniediyl, pyridinediyl, pyrazinediyl, pyrimidinediyl, pyridazinediyl, pyrrolediyl, pyrazolediyl, imidazolediyl, oxazolediyl, isoxazolediyl, thiazolediyl, isotliazolediyl, 1,2,3-trizolediyl, 1,2,4-triazolediyl, oxadiazolediyl, furazandiyl, thiadiazolediyl and 1,3,5-triazinediyl which may be attached through any available position including any available nitrogen atom. It will be appreciated that when Q=H the above group will only have one position of attachment and so group such as furandiyl will be furanyl etc.

A particular value for Z when it is a heterocyclic moiety is, for example, a monocyclic 5- or 6-membered heterocyclic ring or a 5- or 6-membered heterocyclic ring which is fused to a benzene moiety. Thus, particular values will include, furyl, benzofuranyl, thienyl, benzothienyl, pyridyl, quinolyl, isoquinolyl, 1,2,3,4-tetrahydroquinolyl, 1,2,3,4-tetrahydroisoquinolyl, pyrimidinyl, pyrazinyl, pyrrolyl, indolyl, indolinyl, benzimidazolyl, oxazolyl, benzoxazolyl, isoxazolyl, thiazolyl, benzthiazolyl and oxadiazolyl.

A particular value for $R^1$ to $R^{14}$ when alkyl, is, for example methyl, ethyl, propyl, isopropyl and tert-butyl.

A particular value for $L^1$ or $L^2$ when alkylene is, for example, methylene, ethylene or trimethylene.

A particular value for $Ar^1$ when naphthyl is, for example, 1-naphthyl or 2-naphthyl.

A particular value for $Ar^1$ when phenylalkenyl is, for example, styryl, cinnamyl or 3-phenylprop-2-enyl.

A particular value for $Ar^1$ when phenylalkynyl is, for example, 2-phenylethynyl, 3-phenylprop-2-ynyl or 2-phenylprop-1-ylnyl.

A particular value for A is methylene.

A particular value for T is CH.

More particularly, $G^2$ is CH or N; $G^1$ is CH.

More particular values are $G^1$ is CH or N; $G^2$ is CH.

More particularly when T is N, $X^1$ is selected from a bond, CO, $SO_2$, and $CR^1R^2$.

More particularly when T is CN, $X^1$ is selected from a bond, CO, $SO_2$, $CR^1R^2$ and O.

More particularly $Y^1$ is a bond.

More particularly, $Ar^1$ is selected from a phenylene ring and a 6-membered heteroaryl moiety selected from these mentioned above.

More particularly, Q is selected from hydrogen and a group of formula $L^1X^2L^2Z$ in which $L^1$ is (1–4C)alkylene or a bond, $X^2$ is selected from $NR^{12}CO$, $NR^{10}SO_2$, $NR^{13}COR^{14}$ and $SO_2$, and $L^2$ is a bond or (1–4C)alkylene; and Z is as defined above.

More particularly $X^1$—$Y^1$ taken together are O or S.

In general, it is preferred that $G^1$ and $G^2$ are both CH.

In general, it is preferred that when Q is hydrogen, $X^1$ is selected from $CR^1R^2$, $SO_2$ and CO.

In general, it is preferred that $L^1$ and $L^2$ are selected from $CH_2$ and a bond.

In general, it is preferred that when Q is a group of formula $L^1X^2L^2Z$, $X^1$ is a bond.

In general, it is preferred that T is N.

In general, it is preferred that $Ar^1$ is a phenylene ring or a pyridyl ring.

In general, it is preferred that Z is a phenyl, phenyl(2–4C) alkenyl, or naphthyl moiety.

In general it is preferred that $Ar^1$ and $Ar^2$, if substituted are independently mono- or di-substituted.

More preferably, $Ar^1$ is a phenylene ring optionally substituted as hereinbefore defined.

More preferably, Z is a phenyl ring, optionally substituted as hereinbefore defined.

More preferably A and B are both ethylene.

A specific value for $G^1$ is CH or N.

A specific value for $G^2$ is CH or N (especially CH).

A specific value for T is CH or N.

A specific value for $X^1$ is a bond, CO, $SO_2$, $CH_2$ and O. A further specific value is O or S.

A specific value for $Ar^1$ is a phenylene ring or a pyridyl ring. In particular the pyridyl ring is 2-pyridyl. More particular values include furanyl, pyrimidinyl, thiazolyl and oxazolyl.

A specific value for the group $L^1X^2L^2$ is $CH_2NHSO_2$, $NHSO_2$, $CH_2SO_2$, $CH_2NHCONH$, $CH_2NHCO$, $CH_2N(Me)SO_2$, $SO_2$, CO, O, $CH_2$, $OCH_2$, $CH_2CH_2O$, $COCH_2CH_2$ and a bond.

Further specific values for the group $L^1X^2L^2$ include $CH_2NHCO$, $NHSO_2$, $CH_2NHSO_2$, $CH_2NH$, CONH and $SO_2$.

A specific value for Z is phenyl, styryl and naphthyl.

A specific value for A is unsubstituted ethylene or unsubstituted methylene.

A specific value for B is unsubstituted ethylene.

A suitable pharmaceutically-acceptable salt of an aminoheterocyclic derivative of the invention is, for example, an acid-addition salt of an aminoheterocyclic derivative of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of an aminoheterocyclic derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

In one embodiment of the present invention there is provided a compound of formula I, or a pharmaceutically acceptable salt thereof, wherein $G^1$ is CH or N;

$G^2$ is CH or N;

n is 1 or 2;

R is hydrogen, halogeno, trifluoromethyl, trifluoromethoxy, cyano, amino, hydroxy, nitro, (1–4C) alkyl, (1–4C)alkoxy, (1–4C)alkylamino or di(1–4C) alkylamino;

A is methylene or ethylene; B is ethylene; and wherein A and B may independently optionally bear a substituent selected from (1–6C)alkyl, (1–6C)alkoxy, phenyl (1–4C)alkyl, halogeno and (1–6C)alkoxycarbonyl;

T is CH or N;

when T is CH, $X^1$ is selected from $CR^1R$, $SO_2$ SO, CO, a bond, $CR^3R^4O$, O, S and $NR^5$, and when T is N, $X^1$ is selected from $CR^1R^2$, $SO_2$, SO, CO, $CR^3R^4O$ and a bond, wherein $R^1$, $R^2$, $R^3$, $R^4$ and $R^5$ are independently selected from hydrogen and (1–4C)alkyl;

$Y^1$ represents $CR^6R^7$ or a bond, wherein $R^6$ and $R^7$ are independently selected from hydrogen and (1–4C) alkyl;

$Ar^1$ is a phenylene ring or a 5- or 6-membered monocyclic heteroaryl ring containing 1,2 or 3 heteroatoms selected from nitrogen, oxygen and sulphur;

Q is selected from hydrogen and a group of formula $L^1X^2L^2Z$ in which $L^1$ is a bond or (1–4C)alkylene, $L^2$ is a bond or (1–4C)alkylene, $X^2$ is a bond, S, SO, $SO_2$, $CR^8R^9$, CO, $NR^{10}SO_2$, $SO_2NR^{11}$, $NR^{12}CO$, $CONR^{12}$ and $NR^{13}CONR^{14}$ in which $R^8, R^9, R^{10}, R^{11}, R^{12}$, $R^{13}$ and $R^{14}$ are independently selected from hydrogen and (1–4C)alkyl;

Z is selected from phenyl, naphthyl, phenyl(2–4C) alkenyl, phenyl(2–4C)alkvnyl and a heterocyclic moiety containing 1, 2, 3 or 4 heteroatoms selected from nitrogen, oxygen and sulphur:

and wherein the phenyl or heteroaryl moiety in $Ar^1$ and the phenyl, naphthyl, or heterocyclic moiety in Z may optionally bear one or more substituents selected from halogeno, hydroxy, amino, nitro, cyano, carboxy, carbamoyl, (1–6C)alkyl, (2–6C)alkenyl, (2–6C) alkynyl, (1–6C)alkoxy, (3–6C)cycloalkyl, (3–6C) cycloalkyl(1–4C)alkyl, (1–4C)alkylenedioxy, (1–6C) alkylamino, di-[(1–6C)alkyl]amino, N-(1–6C) alkylcarbamoyl, di-N[(1–6C)alkyl]carbamoyl, (1–6C) alkanoylamino, (1–6C)alkoxycarbonyl, (1–6C) alkylthio. (1–6C)alkylsulphinyl, (1–6C) alkylsulphonyl, halogeno(1–6C)alkyl, halogeno(1–6C) alkoxy, (1–6C)alkanoyl and tetrazoyl;

provided that the compound is not N-[4-[4-(4-pyridyl) piperazin-1-ylcarbonyl]phenyl]-(E)-4-chlorostyrenesulphonamide, and pharmaceutically acceptable salts thereof.

Particular, prepared and specific values include the appropriate values mentioned above. In a particular aspect of this embodiment when $X^1$ is CO, $Ar^1$ is phenylene which optionally bears 1 or 2 substituents selected from halogeno, trifluoromethyl, (1–4C)alkyl and (1–4C)alkoxy, and $L^2$ is a bond to Q, then $X^2$ is not a bond.

In a further embodiment of the present invention Q is hydrogen and $G^1$, $G^2$, R, n, A, B, T, $X^1$, $Ar^1$ and the optional substituents for the phenyl or heteroaryl moieties in $Ar^1$ may have any of the values hereinbefore defined.

Particular compounds of this embodiment include compounds of formula I and their pharmaceutically acceptable salts in which R, n, Z, the optional substituents for a phenyl or heteroaryl moiety on $Ar^1$ and the optional substituents for A and B may take the values hereinbefore defined, (unless stated otherwise) and:

(a) $G^1$ is CH or N; $G^2$ is CH; T is N or CH; when T is N, $X^1$ is $CR^1R^2$, $SO_2$, CO; when T is CH, $X^1$ is $CR^1R^2$, $SO_2$, CO, O, S, $NR^3$ or a bond, in which $R^1$, $R^2$ and $R^3$ are independently selected from hydrogen and (1–4C)alkyl; $Y^1$ is a bond, A and B are both ethylene; $Ar^1$ is a phenyl ring;

(b) $G^1$ is CH or N; $G^2$ is CH, T is N, $X^1$ is $CH_2$, $SO_2$ or CO, A and B are ethylene $Y^1$ is a bond, $Ar^1$ is a phenyl ring;

(c) $G^1$ is CH, $G^2$ is CH, T is N, $X^1$ is $CH_2$, $SO_2$ or CO, A and B are ethylene. $Y^1$ is a bond, $Ar^1$ is a phenyl ring;

(d) $G^1$ is CH or N, $G^2$ is CH, T is CH, A is methylene, B is ethylene, $X^1$ is O or a bond, $Y^1$ is a bond, $Ar^1$ is a phenyl or pyridyl ring;

(e) $G^1$ is CH or N, $G^2$ is CH, T is N, $X^1$ is $CH_2$, $SO_2$, CO, A and B are ethylene, $Y^1$ is a bond, $Ar^1$ is a pyridyl ring; or additionally (f) which is as (d) above but wherein $X^1$ is O or S. It will be appreciated that Q is H in each of the above.

Further particular compounds of this embodiment (Q=H), include compounds of formula I and their pharmaceutically acceptable salts in which R, n, the optional substituents for a phenyl or heteroaryl moiety on $Ar^1$ and the optional substituents for A and B may take the values hereinbefore defined, (unless stated otherwise) and:

(a) $G^2$ is CH or N; $G^1$ is CH; T is N or CH; when T is N, $X^1$ is $CR^1R^2$, $SO_2$, CO; when T is CH, $X^1$ is $CR^1R^2$, $SO_2$, CO, O, S, $NR^3$ or a bond, in which $R^1$, $R^2$ and $R^3$ are independently selected from hydrogen and (1–4C)alkyl; $Y^1$ is a bond, A and B are both ethylene; $Ar^1$ is a phenyl ring;

(b) $G^2$ is CH or N; $G^1$ is CH, T is N, $X^1$ is $CH_2$, $SO_2$ or CO, A and B are ethylene, $Y^1$ is a bond, $Ar^1$ is a phenyl ring;

(c) $G^2$ is CH or N, $G^1$ is CH, T is CH, A is methylene, B is ethylene, $X^1$ is O or a bond, $Y^1$ is a bond, $Ar^1$ is a phenyl or pyridyl ring;

(d) $G^2$ is CH or N, $G^1$ is CH, T is N, $X^1$ is $CH_2$, $SO_2$, CO, A and B are ethylene, $Y^1$ is a bond, $Ar^1$ is a pyridyl ring; or additionally (e) which is as (c) above but wherein $X^1$ is O or S.

In a further embodiment of the present invention, Q is a group of formula $L^1X^2L^2Z$ and $G^1$, $G^2$, R, n, A, B, T, $X^1$, $Ar^1$, Z and the optional substituents for the phenyl, naphthyl, heteroaryl and heterocyclic moieties in $Ar^1$ and Z are as defined above.

Particular compounds of this embodiment include compounds of formula I and their pharmaceutically acceptable salts in which R, n, $Ar^1$, Z the optional substituents for A and B and the optional substituents for a phenyl, heteroaryl, naphthyl or benzene moieties in $Ar^1$ or Z may take the values hereinbefore defined (unless stated otherwise) and:

(a) $G^1$ is CH or N, $G^2$ is CH, T is N or CH, A is ethylene, or methylene, B is ethylene, $X^1$ and $Y^1$ are bonds, Q is a group of formula $L^1X^2L^2Z$ in which $L^1$ is (1–4C)alkylene or a bond, $X^2$ is selected from $CONR^{12}$, $NR^{12}CO$, $NR^{10}SO_2$, $NR^{13}CONR^{14}$ and $SO_2$, L is a (1–4C)alkylene or a bond, $R^{10}$, $R^{12}$, $R^{13}$ and $R^{14}$ are independently selected from hydrogen and (1–4C)alkyl;

(b) $G^1$ is CH or N, $G^2$ is CH, T is N or CH, A and B are ethylene. $X^1$ and $Y^1$ are bonds; Q is a group of formula $L^1X^2L^2Z$ in which $L^1$ is (1–4C)alkylene or a bond, $X^2$ is NHCO, $NHSO_2$, NHCONH or $SO_2$, $L^2$ is (1–4C)alkylene or a bond, and R and n are as hereinbefore defined;

(c) $G^1$ is CH, $G^2$ is CH, T is N or CH, A and B are ethylene. $X^1$ and $Y^1$ are bonds, Q is $L^1X^2L^2Z$ in which $L^1$ is (1–4C)alkylene, $L^2$ is a bond, $X^2$ is NHCO, $NHSO_2$, NHCONH and $SO_2$; or (d) $G^1$ is CH or N (preferably CH), $G^2$ is CH; T is N or CH (preferably N), $X^1$ and $Y^1$ are bonds, A and B are ethylene, $Ar^1$ is phenyl, Q is a group of formula $L^1X^2L^2Z$ in which $L^1$ is (1–4C)alkylene or a bond (preferably alkylene such as $CH_2$), $X^2$ is NHCO, $NHSO_2$, NHCONH or $SO_2$, $L^2$ is (1–4C)alkylene or a bond (preferably a bond);

Further particular compounds of this embodiment include compounds of formula I and their pharmaceutically acceptable salts in which R, n, $Ar^1$, Z the optional substituents for A and B and the optional substituents for a phenyl, heteroaryl, naphthyl or benzene moieties in $Ar^1$ or Z may take the values hereinbefore defined (unless stated otherwise) and:

(a) $G^2$ is CH or N, $G^1$ is CH, T is N or CH, A is ethylene, or methylene, B is ethylene, $X^1$ and $Y^1$ are bonds, Q is a group of formula $L^1X^2L^2Z$ in which $L^1$ is (1–4C)alkylene or a bond, $X^2$ is selected from $CONR^{12}$, $NR^{12}CO$, $NR^{10}SO_2$, $NR^{13}CONR^{14}$ and $SO_2$, L is a (1–4C)alkylene or a bond, $R^{10}$, $R^{12}$, $R^{13}$ and $R^{14}$ are independently selected from hydrogen and (1–4C)alkyl;

(b) $G^2$ is CH or N, $G^1$ is CH, T is N or CH, A and B are ethylene, $X^1$ and $Y^1$ are bonds; Q is a group of formula $L^1X^2L^2Z$ in which $L^1$ is (1–4C)alkylene or a bond. $X^2$ is NHCO, $NHSO_2$, NHCONH or $SO_2$, $L^2$ is (1–4C)alkylene or a bond, and R and n are as hereinbefore defined;

(c) $G^2$ is CH or N (preferably CH), $G^1$ is CH; T is N or CH (preferably N), $X^1$ and $Y^1$ are bonds, A and B are ethylene, $Ar^1$ is phenyl, Q is a group of formula $L^1X^2L^2Z$ in which $L^1$ is (1–4C)alkylene or a bond (preferably alkylene such as $CH_2$), $X^2$ is NHCO, $NHSO_2$, NHCONH or $SO_2$, $L^2$ is (1–4C)alkylene or a bond (preferably a bond);

In a preferred embodiment there is provided a compound of formula I or a pharmaceutically acceptable salt thereof, wherein:

$G^1$ is CH, $G^2$ is CH, T is N, $X^1$ is CO, $SO_2$, or $CH_2$, A and B are ethylene, $Ar^1$ is phenyl, Q is hydrogen, and R, m and the optional substituent for the phenyl moiety of $Ar^1$ are as hereinbefore defined.

Particular, preferred and specific values include the appropriate values mentioned above.

In a further preferred embodiment there is provided a compound of formula I or a pharmaceutically acceptable salt thereof wherein: $G^1$ is CH, $G^2$ is CH, T is N, $X^1$ is a bond, $Y^1$ is a bond, A and B are ethylene, $Ar^1$ is phenyl, Q is of formula $L^1X^2L^2Z$ in which $L^1$ is (1–4C)alkylene (preferably $CH_2$), $X^2$ is $NR^6SO_2$ in which $R^6$ is (1–4C)alkyl or hydrogen (preferably hydrogen), and Z is phenyl, wherein the phenyl moiety of $Ar^1$ and Z may optionally be substituted as hereinbefore defined and R and m are as hereinbefore defined.

Particular, preferred and specific values include the appropriate values mentioned above.

In a further embodiment of the present invention, Z is (1–4C)alkyl or hydrogen, more particularly (1–4C)alkyl, and the other groups are as hereinbefore defined.

Compounds of particular interest include the compounds described in the accompanying examples and as such they and their pharmaceutically acceptable salts are provided as a further feature of the present invention.

The compounds of formula I and their pharmaceutically acceptable salts may be prepared by processes known to be applicable to the preparation of structurally related compounds. These procedures are illustrated by the following representative processes in which the various groups and radicals such as $G^1$, $G^2$, A, B, $X^1$, $Ar^1$ and Q are as hereinbefore defined (unless stated otherwise), and are provided as a further feature of the present invention. In cases where the compounds contain a group such as an amino, hydroxy, or carboxy group, this group may be protected using a conventional protecting group which may be removed when desired by conventional means.

(a) For the production of those compounds of the formula I wherein T is N and $X^1$ is CO, the reaction, conveniently in the presence of a suitable base, of an amine of the formula II,

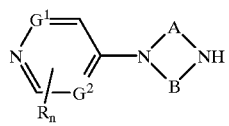

II with an acid of the formula III,

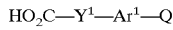

$HO_2C—Y^1—Ar^1—Q$  III or a reactive derivative thereof.

A suitable reactive derivative of an acid of the formula III is, for example, an acyl halide, for example an acyl chloride formed by the reaction of the acid and an inorganic acid chloride, for example thionyl chloride; a mixed anhydride, for example an anhydride formed by the reaction of the acid with a chloroformate such as isobutyl chloroformate or with an activated ketone such as 1,1'-carbonyldiimidazole: an active ester, for example an ester formed by the reaction of the acid and a phenol such as pentafluorophenol, an ester such as pentafluorophenyl trifluoroacetate or an alcohol such as N-hydroxybenzotriazole or N-hydroxysuccinimide; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as N,N'-dicyclohexylcarbodiimide or N-(3-dimethylaminopropyl)-N'-ethylcarbodiimide.

The reaction is conveniently carried out in the presence of a suitable base such as, for example, an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride, or an organometallic base such as an alkyl-lithium, for example n-butyl-lithium, or a dialkylamino-lithium, for example lithium di-isopropylamide, or, for example, an organic amine base such as, for example, pyridine, 2,6-lutidine, collidine, 4-dimethylaminopyridine, triethylamine, morpholine or diazabicyclo[5.4.0]undec-7-ene. The reaction is also preferably carried out in a suitable inert solvent or diluent, for example methylene chloride, chloroform, carbon tetrachloride, tetrahydrofuran, 1,2-dimethoxyethane, N,N-dimethylformamide, N,N-dimethylacetamide, N-methylpyrrolidin-2-one, dimethylsulphoxide or acetone, and at a temperature in the range, for example, −78° to 150° C. conveniently at or near ambient temperature.

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium-on-carbon.

An analogous procedure may be used for those compounds of formula I wherein $X^1$ is a group of the formula SO or $SO_2$.

(b) For the production of those compounds of the formula I wherein T is CH and $X^1$ is O the reaction, conveniently in the presence of a suitable coupling agent, of a compound of the formula IV.

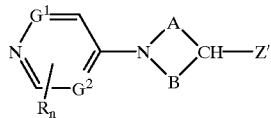

IV wherein Z' is a displaceable group, with a compound of the formula V.

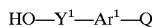

V

A suitable value for the displaceable group Z' is, for example, a halogeno or sulphonyloxy group, for example a fluoro, chloro, bromo, mesyloxy or 4-tolylsulphonyloxy group.

A suitable reagent for the coupling reaction when Z' is a halogeno or suiphonyloxy group is, for example, a suitable base, for example, an alkali or alkaline earth metal carbonate, hydroxide or hydride, for example sodium carbonate, hydroxide or hydride, for example sodium carbonate, potassium carbonate, sodium hydroxide, potassium hydroxide, sodium hydride or potassium hydride. The alkylation reaction is preferably performed in a suitable inert solvent or diluent, for example N,N-dimethylformamide, N,N-dimethylacetamide, dimethylsulphoxide, acetone, 1,2-dimethoxyethane or tetrahydrofuran, and at a temperature in the range, for example, −10° to 150° C., conveniently at or near ambient temperature.

Alternatively, the displaceable group Z' is provided in place of the HO-group in the compound of formula V and the HO-group is provided in place of the displaceable group Z' in the compound of formula IV.

A suitable reagent for the coupling reaction of the alcohol of the formula IV wherein Z is a hydroxy group is, for example, the reagent obtained when said alcohol is reacted with a di-(1–4C)alkyl azodicarboxylate in the presence of a triarylphosphine or tri-(1–4C)alkylphosphine, for example with diethyl azodicarboxylate in the presence of triphenylphosphine or tributylphosphine. The reaction is preferably performed in a suitable inert solvent or diluent, for example acetone, 1,2-dimethoxyethane or tetrahydrofuran, and at a temperature in the range, for example, 10° to 80° C., conveniently at or near ambient temperature.

An analogous procedure may be employed for the preparation of those compounds of the formula I wherein T is CH and $X^1$ is a group of the formula S.

(c) For the production of those compounds of the formula I wherein $T^1$ is N and $X^1$ is $CH(R^2)$, the reductive amination of a keto compound of the formula VI,

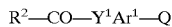

VI with an amine of the formula II.

Any reducing agent known in the art for promoting a reductive amination reaction may be employed. A suitable reducing agent is, for example, a hydride reducing agent, for example an alkali metal aluminium hydride such as lithium aluminium hydride or, preferably, an alkali metal borohydride such as sodium borohydride, sodium cyanoborohydride, sodium triethylborohydride, sodium trimethoxyborohydride and sodium triacetoxyborohydride. The reaction is conveniently performed in a suitable inert solvent or diluent, for example tetrahydrofuran and diethyl ether for the more powerful reducing agents such as lithium aluminium hydride, and, for example, methylene chloride or a protic solvent such as methanol and ethanol for the less powerful reducing agents such as sodium triacetoxyborohydride. The reaction is performed at a temperature in the range, for example, 10° to 80° C., conveniently at or near ambient temperature.

(d) The reaction of an amine of formula II with a compound of formula VII,

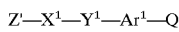

XI wherein Z' is a displaceable group as defined hereinbefore. The reaction may be performed, for example, in the presence of a catalytic amonut of sodium hydride. The reaction is conveniently performed in a suitable inert solvent or diluent as defined hereinbefore and at a temperature in the range, for example, 0° to 150° C., conveniently at or near ambient temperature.

(e) The reaction of a compound of formula VIII

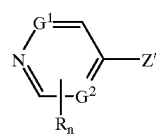

VIII wherein Z' is a displaceable group as defined herein before with a compound of formula IX

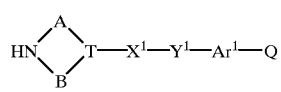

IX

The reaction is conveniently performed in a suitable inert solvent or diluent as defined hereinbefore and at a temperature in the range, for example, 0° to 150° C., conveniently at or near ambient temperature.

(f) For the production of those compounds of the formula I wherein $X^2$ is a group of the formula $NR^{10}SO_2$, the reaction, conveniently in the presence of a suitable base as defined hereinbefore, of an amine of the formula X, with a compound of the formula XI,

XI wherein Z' is a displaceable group as defined hereinbefore.

The reaction is conveniently performed in a suitable inert solvent or diluent as defined hereinbefore and at a temperature in the range, for example, 0° to 150° C., conveniently at or near ambient temperature.

An analogous procedure may be employed for those compounds of the formula I wherein $X^2$ is a group of the formula $NR^{12}CO$.

(g) For the production of those compounds of the formula I wherein $X^2$ is a group of the formula $NR^{13}CONR^{14}$, the reaction, conveniently in the presence of a suitable base as defined hereinbefore, of an amine of the formula X,

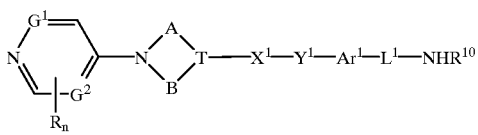

X with a compound of the formula XII, $$O=C=N-L^1-Z \quad \text{XII}$$

The reaction is conveniently performed in a suitable inert solvent or diluent as defined hereinbefore and at a temperature in the range, for example, 0° to 150° C., conveniently at or near ambient temperature.

(h) For the production of those compounds of the formula I wherein $X^2$ is a group of the formula $NR^{10}SO_2$ and $R^{10}$ represents (1–4C)alkyl, the reaction, conveniently in the presence of a suitable base as defined hereinbefore, of a corresponding sulphonamide of the formula XIII,

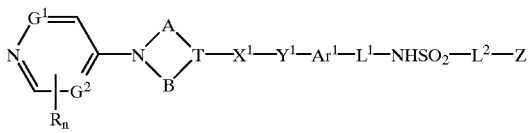

XIII with a compound of the formula XIV, $$R^{10}-Z' \quad \text{XIV}$$

wherein Z' is a displaceable group as defined hereinbefore.

The reaction is conveniently performed in a suitable inert solvent or diluent as defined hereinbefore and at a temperature in the range, for example, 0 to 150° C. conveniently at or near ambient temperature.

An analogous procedure may be employed for those compounds of the formula I wherein $X^2$ is a group of the formula $SO_2NR^{11}$ or $NR^{12}CO$.

(i) For the production of those compounds of the formula I wherein $L^1$ represents (1–4C)alkylene and $X^2$ is S, the reaction, conveniently in the presence of a suitable base as defined hereinbefore, of a compound of the formula XV,

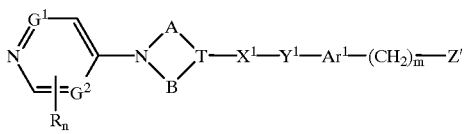

XV wherein m is 1,2,3 or 4, and Z' is a displaceable group as defined hereinbefore with a thiol of the formula XVI, $$HS-L^2-Z \quad \text{XVI}$$

The reaction is conveniently performed in a suitable inert solvent or diluent as defined hereinbefore and at a temperature in the range, for example, 0° to 150° C. conveniently at or near ambient temperature.

(j) For the production of those compounds of the formula I wherein $Ar^1$ or Z bears a carboxy or carboxy-containing group, the hydrolysis of a compound of the formula I wherein $Ar^1$ or Z bears a (1–6C)alkoxycarbonyl group.

The hydrolysis reaction may conveniently be carried out in a conventional manner using, for example, acidic or basic catalysis. A suitable acid for the acidic hydrolysis of an ester group is, for example, an inorganic acid such as hydrochloric or sulphuric acid. A suitable base for the basic hydrolysis of an ester group is, for example, an alkali or alkaline earth metal hydroxide such as sodium hydroxide or potassium hydroxide.

The reaction is conveniently performed in a suitable solvent or diluent such as an alcohol, for example methanol or ethanol, and at a temperature in the range, for example 0° to 120° C. conveniently in the range of 15° to 60° C.

(k) For the production of those compounds of the formula I wherein $Ar^1$ or Z bears a carbamoyl, N-(1–6C) alkylcarbamoyl or alkyldi-N[(1–6C)carbamoyl group, the reaction of a compound of the formula I wherein $A^1$ or Z bears a carboxy group, or a reactive derivative thereof as defined hereinbefore, with ammonia or an appropriate alkylamine or dialkylamine.

The reaction is conveniently performed in a suitable inert solvent or diluent as defined hereinbefore and at a temperature in the range, for example, 0° to 120° C. conveniently in the range 15° to 60°.

(l) For the production of those compounds of the formula I wherein $X^1$ is a group of the formula SO or $SO_2$ wherein $Ar^1$ or Z bears a (1–6C)alkylsulphinyl or (1–6C) alkylsulphonyl, substituent or wherein $X^2$ is a group of the formula SO or $SO_2$ the oxidation of the corresponding compound of the formula I which contains a thio group.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising a gent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, at or near ambient temperature, that is in the range 15 to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

As mentioned above, it will be appreciated that in some of the reactions mentioned herein it may be necessary/desirable to protect any sensitive groups in the compounds. The instances where protection is necessary or desirable and suitable methods for protection are known to those skilled in the art. Thus, if reactants include groups such as amino, carboxy or hydroxy it may be desirable to protect the group in some of the reactions mentioned herein. Suitable protecting groups are mentioned under (a) above. The protecting groups may be removed at any convenient stage in the synthesis, using conventional techniques well known in the chemical art.

It will also be appreciated that certain of the various optional substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acylhalide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

When a pharmaceutically-acceptable salt of a compound of the formula I is required, it may be obtained, for example, by reaction of said compound with the appropriate acid (which affords a physiologically acceptable anion), or with the appropriate base (which affords a physiologically acceptable cation), or by any other conventional salt formation procedure.

When an optically active form of a compound of the formula I is required, it may be obtained, for example, by carrying out one of the aforesaid procedures using an optically active starting material or by resolution of a racemic form of said compound using a conventional procedure. As mentioned previously, the compounds of the formula I (and their pharmaceutically-acceptable salts) are inhibitors of the enzyme oxido-squalene cyclase. Thus, the compounds of the present invention are capable or inhibiting cholesterol biosynthesis and hence in lowering cholesterol levels in blood plasma.

The beneficial pharmacological properties of the compounds of the present invention may be demonstrated using one or more of the following techniques.

(a) In vitro Test to Measure Inhibition of Oxido-squalene Cyclase

This test measures the inhibition of microsomal oxido-squalene cyclase in vitro by compounds at set concentrations in the incubation medium.

Microsomes are prepared from rat liver according to methods known in the art, for example, the method described in published European Patent Application No 324,421 and stored in liquid nitrogen prior to assay. Assay vials are kept at 37° C. throughout the incubation. The microsomes typically contain 15–20 mg of protein per ml of microsomes. For assay, 1 ml of microsomes are diluted by the addition of 722 µl of 50 mM phosphate buffer pH 7.4.

Phosphate buffered Tween 80 (polyoxyethylene sorbitan monolaurate) is prepared by adding 0.1 g Tween 80 to 100 ml of 50 mM phosphate buffer.

A stock solution of oxido-squalene is made up as a solution in ethanol (0.65 mg.ml$^{-1}$). 18 µl of radio-labelled oxido-squalene (1 µCi.ml$^{-1}$) is evaporated to dryness under a stream of nitrogen and redissolved in 1 ml of ethanol and 1 ml of the stock solution of oxido-squalene is added.

The test compound is dissolved in dimethyl sulphoxide to give a 10$^{-4}$M stock solution. Dilutions are made from the stock to give 10$^{-5}$M, 10$^{-6}$M etc.

Phosphate buffered Tween 80 (28 µl) is placed in 5 ml disposable plastic vials and 4 µl of the solution of the test compound is added and mixed well. An aliquot of the oxido-squalene mix (15 µl) is added and the vials preincubated for 10 minutes at 37° C. A portion of the microsomes (14.6 µl) are then added and incubated for a further 1 hour. The reaction is stopped by the addition of 315 µl of a mixture of 16% KOH in 20% ethanol.

The samples are then placed in a water bath at 80° C. for 2 hours to saponify. At the end of this process water (630 µl) is added followed by hexane (5 ml). The samples are tumble mixed for 5 minutes and then centrifuged. The hexane phase is removed and evaporated under nitrogen. The samples are then reconstituted in 300 µl of a 80:20 mixture of acetonitrile:isopropyl alcohol. The samples are then chromatographed using a Hichrom 30DS1 column with an isocratic elution using a 95:5 mixture of acetonitrile:isopropyl alcohol and a flow rate of 1 ml.min$^{-1}$. The output from the UV detector is connected to a radio-chemical detector to visualise radiolabelled sterols. Reaction rate is measured as the conversion of oxido-squalene to lanosterol, and the effects of test compounds are expressed as an inhibition of this process.

By way of example, the compound described in Example 25 cave 100% inhibition at 1 µM.

(b) In vivo Test to Measure Inhibition of Oxido-Squalene Cyclase

The ability of a compound to inhibit oxido-squalene cyclase and/or inhibit cholesterol biosynthesis may be assessed by a routine laboratory procedure carried out in the rat. The test involves administration of the compound to rats on a reversed lighting regimen. Female rats (35–55 g) are housed in reverse lighting conditions (red light from 0200 h–1400 h) for a period of about 2 weeks prior to test. Animals are allowed free access to chow and drinking water throughout this period. At test, animals should weigh 100–140 g. The rats are dosed orally, with the compound (typically 10–50 mg/kg) formulated in a polyethylene glycol/hydroxypropylmethyl cellulose mix. After 1 hour the rats are given triturated sodium mevalonate (15 µCi/kg) intraperitoneally. Two hours after administration of the compound the rats are terminated and a piece of liver removed and weighed. The tissue is saponified at 80° C. for 2 hours in an ethaniolic/potassium hydroxide solution (80% w/v aqueous KOH diluted 1:10 with ethanol). Water (2 ml) is added and the mixture extracted with iso-hexane (2×5 ml). The organic extracts are combined, evaporated to dryness under a stream of nitrogen and the residue is dissolved in a mixture of acetonitrile/iso-propanol (300 µl). An aliquot (200 µl) of this solution is loaded onto a HPLC column to separate the sterols. The radio-label content of each fraction is assessed using a radio chemical flow detector. Inhibitors of oxido-squalene cyclase are classed as those compounds which caused a build up of substrate and a concomitant disappearance of cholesterol and its precursors. ED50 values are generated in the usual manner.

By way of example, the compound described in Example 18 below gave 59% inhibition of cholesterol biosynthesis when dosed at 2 mg/kg; and the compound described in Example 27 70% inhibition when dosed at 2 mg/kg.

The compounds of the present invention are oxido-squalene cyclase inhibitors and hence possess the property of inhibiting cholesterol biosynthesis. Accordingly, there is also provided the use of a compound of formula I, or a pharmaceutically acceptable salt thereof. (as hereinbefore defined) for the manufacture of a medicament for inhibiting cholesterol biosynthesis. The compound N-[4-[4-(4-pyridyl)

piperazin-1-ylcarbonyl]phenyl](E)-4-chlorostyrenesulphonamide and its salts are included in this aspect of the present invention and the aspect which follow relating to uses of the compounds of the present invention. Thus the compounds of the present invention will be useful in treating diseases or medical conditions in which an inhibition of oxido-squalene cyclase is desirable, for example those in which a lowering of the level of cholesterol in blood plasma is desirable.

In particular, the compounds of the present invention will be useful in treating hypercholesterolemia and hypertriglyceridaemia, and in the treatment of atherosclerotic vascular diseases such as atherosclerosis, coronary heart disease including myocardial infarction, angina, stroke and peripheral vascular disease. Such uses may lead to a reduction of morbidity in patients with ischaemic heart disease, whether or not they have a medical history of coronary heart disease. Compounds of the invention may also have benefit in the treatment of dermatological conditions such as xanthomas and xanthelasmas and in the treatment of gallstones.

Thus according to a further feature of the present invention there is provided a method of inhibiting oxido-squalene cyclase in a warm-blooded animal (such as man) requiring such treatment, which method comprises administering to said animal an effective amount of a compound of formula I (as herein defined), or a pharmaceutically-acceptable salt thereof. In particular, the present invention provides a method of inhibiting cholesterol biosynthesis, and more particularly to a method of treating hypercholesterolemia and atheromatous vascular degeneration (such as atherosclerosis).

Thus the present invention also provides the use of a compound of formula I (as herein defined), or a pharmaceutically-acceptable salt thereof, for the manufacture of a medicament for treating diseases or medical conditions in which a lowering of the level of cholesterol in blood plasma is desirable (such as hypercholesterolemia and atherosclerosis).

In particular, the compounds of the present invention are potentially useful in inhibiting cholesterol biosynthesis in man and hence in treating the above-mentioned medical conditions in man.

When used in the treatment of diseases and medical conditions such as those mentioned above it is envisaged that a compound of formula I (or a pharmaceutically acceptable salt thereof) will be administered orally, intravenously, or by some other medically acceptable route so that a dose in the general range of, for example, 0.01 to 10 mg per kg body weight is received. However it will be understood that the precise dose administered will necessarily vary according to the nature and severity of the disease, the age and sex of the patient being treated and the route of administration.

In general, the compounds of formula I (or a pharmaceutically-acceptable salt thereof) will usually be administered in the form of a pharmaceutical composition, that is together with a pharmaceutically acceptable diluent or carrier, and such a composition is provided as a further feature of the present invention.

A pharmaceutical composition of the present invention may be in a variety of dosage forms. For example, it may be in the form of tablets, capsules, solutions or suspensions for oral administration, in the form of a suppository for rectal administration; in the form of a sterile solution or suspension for parenteral administration such as by intravenous or intramuscular injection.

A composition may be obtained by conventional procedures using pharmaceutically acceptable diluents and carriers well known in the art. Tablets and capsules for oral administration may conveniently be formed with a coating, such as an enteric coating (for example, one based on cellulose acetate phthalate), to minimise dissolution of the active ingredient of formula I (or a pharmaceutically-acceptable salt thereof) in the stomach or to mask unpleasant taste.

The compounds of the present invention may, if desired, be administered together with (or sequentially to) one or more other pharmacological agents known to be useful in the treatment of cardiovascular disease, for example, together with agents such as HMG-CoA reductase inhibitors, bile acid sequestrants, other hypocholesterolaemic agents such as fibrates, for example gemfibrozil, and drugs for the treatment of coronary heart disease.

As inhibitors of oxido-squalene cyclase, the compounds of the present invention may also find utility as antifungal agents, and so the present invention also provides a method of inhibiting cholesterol biosynthesis in fungi. In particular the present invention provides a method of treating fungal infections which comprises administration to a warm blooded animal, such as man, in need of such treatment an effective amount of a compound of formula I, or a pharmaceutically acceptable salt thereof. When used in this way the compounds of the present invention may, in addition to the formulations mentioned above, be adapted for topical administration and such a composition is provided as a further feature of the present invention. Such compositions may be in a variety of forms, for example creams or lotions.

Selected compounds of the, invention having utility as antifungal agents are compounds of the formula I wherein $G^1$ is CH, $G^2$ is CH or N R is as defined hereinbefore n is 1 or 2

T is CH or N, when T is CH then $X^1Y^1$ together are O or S, when T is N then $X^1Y^1$ together are a bond, $Ar^1$ is a phenylene ring, a pyridyl ring, or a 9- or 10-membered bicyclic heteroaryl ring containing 1, 2, or 3 hetereoatoms selected from nitrogen, oxygen and sulphur, and may optionally bear one or more substituents selected from halogeno, nitro, cyano, (1–6C) alkyl, (1–6C)alkylthio, halogeno(1–6C)alkyl, halogeno (1–6C)alkylthio, halogeno(1–6C)alkoxy, (1–6C) alkoxycarbonyl, Q is selected from hydrogen and a group of formula $L^1X^2L^2Z$ in which $L^1$ is a bond or (1–4C)alkylene, $L^2$ is a bond or (1–4C)alkylene, $X^2$ is a bond, $NR^8$, O or S, in which $R^8$ is hydrogen or (1–4)C alkyl; and Z is selected from phenyl, and a monocyclic heterocyclic moiety containing 1,2,3 or 4 heteroatoms selected from nitrogen, oxygen and sulphur, and may optionally bear one or more substituents selected from halogeno, nitro, cyano, (1–6C) alkyl, (1–6C)alkylthio, halogeno(1–6C) alkyl, halogeno(1–6C)alkylthio, halogeno(1–6C) alkoxy, (1–6C)alkoxycarbonyl;

Further selected antifungal compounds are as above and wherein $Ar^1$ is a phenylene ring, a 2-pyridyl ring, a benzthiazol-2yl ring, a 2-quinoyloxy ring, a benzoxazolyl ring, a thiazolopyridin-2yl ring, or a quinoxalinyloxy ring. Further selected antifungal compounds are as above and wherein R is hydrogen, halogeno or (1–4C)alkyl. Further selected antifungal compounds are as above and wherein the substituent Q on $Ar^1$ is in the 4-position. Further selected antifungal compounds are as above and wherein the substituent(s) on $Ar^1$ and/or Z are independently selected from methyl, methylthio, cyano, nitro, trifluoromethyl, trifluoromethoxy, trifluoromethylthio, chlorine, bromine, fluorine and methoxycarbonyl.

In a further aspect of the invention we claim the use of a compound as defined above as an antifungal agent. We also claim a method for inhibiting cholesterol biosynthesis in fungi which comprises the use of a compound as defined above.

In a further aspect of the invention we claim a pharmaceutical composition comprising one or more compounds as defined above for use in the treatment of fungal infections of the human or animal body.

The antifungal activity of the compounds of the invention may be determined in vitro in standard agar dilution tests and disc-diffusion tests and minimum inhibitory concentrations are obtained. Standard in vivo tests in mice are used to determine the effective dose of the test compounds in controlling systemic fungal infections.

By way of example the following test protocols may be used:

Primary in-vitro Screen

Compounds are formulated in DMSO at 2560 $\mu$g/ml and diluted to four-times the top test concentration in a synthetic medium RPMI-1640. Serial 2-fold dilutions are prepared in microtitre plates and an equal volume of the inoculum added. Compounds are tested against 11 fungal species strains including Candida spp. *Cryptococcus neoformans, Saccharomyces cerevisiae, Aspergillus fumigatus* and *Trichophyton quinckeanum*. The plates are incubated at 30° C., read by eye at 24 h and then at 48 h. MICs and $IC_{50}$s are determined from visual and multiscan (540 nm) readings respectively.

Primary in-vivo Screen

Mice are inoculated intravenously with a lethal challenge of *Candida albicans*. Groups of 4 mice are dosed with test compound at 0.5 and 24 h after infection. The health of the mice is monitored for 72 h at which point the test is terminated. Untreated mice would be expected to die or be culled within 24 h of infection. Activity is determined by increased survival of the treated group over that of control animals.

The invention will now be illustrated in the following Examples in which, unless otherwise stated:

(i) evaporations were carried out by rotary evaporation in vacuo and work-up procedures were carried out after removal of residual solids by filtration;

(ii) operations were carried out at room temperature, that is in the range 18–25° C. and under an atmosphere of an inert gas such as argon;

(iii) column chromatography (by the flash procedure) and medium pressure liquid chromatography (MPLC) were generally performed on Merck Kieselgel silica (Art. 9385) or Merck Lichroprep RP-18 (Art. 9303) reversed-phase silica obtained from E. Merck, Darmstadt, Germany; alternatively high pressure liquid chromatography (HPLC) was performed on a Dynamax C-18 60A preparative reversed-phase column;

(iv) yields are given for illustration only and are not necessarily the maximum attainable;

(v) the structures of the end-products of the formula I were confirmed by nuclear magnetic resonance (NMR) and mass spectral techniques; unless otherwise stated, $CD_3SOCD_3$ solutions of the end-products of the formula I were used for the determination of NMR spectral data, chemical shift values were measured on the delta scale: the following abbreviations have been used; s, singlet; d, doublet; t, triplet; q, quartet; m, multiplet;

(vi) intermediates were not generally fully characterised and purity was assessed by thin layer chromatographic, infra-red (IR) or NMR analysis;

(vii) melting points were determined using a Mettler SP62 automatic melting point apparatus or an oil-bath apparatus: melting points for the end-products of the formula I were generally determined after crystallisation from a conventional organic solvent such as ethanol, methanol, acetone, ether or hexane, alone or in admixture; and (viii) the following abbreviations have been used:
DMF N,N-dimethylformamide; THF tetrahydrofuran; DMSO dimethylsulphoxide; $Et_3N$ triethylamine; $CH_2Cl_2$ dichloromethane; $Na_2SO_4$ sodium sulphate (anhydrous);
$K_2CO_3$ potassium carbonate; NaOH sodium hydroxide; MeOH methanol; $NH_4OH$ ammonium hydroxide;
EtOAc ethyl acetate; $^iPrNH_2$ isopropylamine;
$Et_2O$ diethyl ether; MTBE methyl t-butyl ether;

'Column chromatography' refers to separation of components of a mixture by passage of a solution through a sinter filled with silica gel (230–400 mesh, E Merck, Darmstadt, Germany), with suction applied from beneath.

The starting materials are described below or are known materials. Many of the starting materials are commercially available. The following lists some of the commercially available starting materials:

| Compound | Supplier |
| --- | --- |
| 4-chloropyridine hydrochloride | Aldrich |
| 3-hydroxypyrrolidine | Aldrich |
| (3R)-3-hydroxypyrrolidine | Fluorochem |
| 4-hydroxypiperidine | Aldrich |
| 2-bromo-5-trifluoromethylpyridine | Fluorochem |
| 2-bromo-5-nitropyridine | Aldrich |
| 2,5-dichloropyridine | Aldrich |
| 2,5-dibromopyridine | Aldrich |
| 2-bromo-5-methylpyridine | Aldrich |
| methyl 6-chloronicotinate | Lancaster |
| 2-chloro-5-cyanopyridine | Avocado |
| 2-chloro-3-nitro-4-methylpyridine | Aldrich |
| 2,3-dichloropyridine | Aldrich |
| 2-bromo-5-nitropyridine | Aldrich |
| 2-chloroquinoline | Aldrich |
| 1-(4-pyridyl)piperazine | Emkachem |
| 2,3-dichloro-5-trifluoromethylpyridine | Aldrich |
| 2,3,5-trichloropyridine | Fluka |
| 4-nitrobromobenzene | Aldrich |
| 4-chlorophenol | Aldrich |
| 4-(trifluoromethyloxy)phenol | Fluorochem |
| 4-methylmercaptophenol | Aldrich |
| 4-trifluoromethylmercaptophenol | Fluorochem |
| 4-trifluoromethylphenol | Janssen |
| 4-bromophenol | Aldrich |

EXAMPLE 1

A solution of 4-toluenesulphonyl chloride (0.38 g) in dichloromethane (25 ml) was added dropwise to a stirred solution of 1-(4-aminomethylphenyl)-4-(4-pyridyl) piperazine (536 mg) in dichloromethane (50 ml) containing triethylamine (0.5 ml). The reaction mixture was stirred at ambient temperature overnight. The mixture was washed with aqueous sodium carbonate solution, water, brine, dried ($MgSO_4$) and evaporated. The residue was recrystallised from methanol to give 1-(4-pyridyl)-4-(4-toluenesulphonamidomethylphenyl)piperazine (0.36 g) as a solid, m.p. 196–198° C.; microanalysis, found: C, 65.2; H,6.2; N,13.2%; $C_{23}H_{26}N_4O_2S$ requires: C,65.4; H,6.2; N,13.3%; NMR: 2.37(s, 3H), 3.15–3.3(m, 4H), 3.4–3.55(m, 4H), 3.81–3.88(d, 2H), 6.8–6.93(dd, 4H), 7.03–7.15 (d, 2H), 7.32–7.4(d, 2H), 7.6–7.7(d, 2H), 7.8–7.95(t, 1H), 8.1–8.2(d, 2H); MS: m/z 423 $(MH)^+$.

The 1-(4-aminomethylphenyl)-4-(4-pyridyl)piperazine used as starting material was prepared as follows:

A solution of N-(4-pyridyl)piperazine (9.78 g), 4-fluorobenzonitrile (7.26 g) and powdered potassium carbonate(10 g) was stirred at 100° C. in DMSO (100 ml) overnight. The solution was poured into water (500 ml) to give a precipitate which was filtered and washed with water. The crude solid was dried in a vacuum oven overnight then dissolved in dichloromethane and purified by flash chromatography on alumina (ICN Alumina N 32–63) using an increasing concentration of ethyl acetate in dichloromethane (up to 100% ethyl acetate) as eluant. This gave a solid which was recrystallised from a mixture of ethyl acetate/isohexane to give 1-(4-cyanophenyl)-4-(4-pyridyl)piperazine (7.5 g) as a solid, m.p.157–158° C.; microanalysis. found: C,72.7; H,6.1; N,21.0%; $C_{16}H_{16}N_4$ requires: C,72.7; H,6.1; N,21.2%; NMR: 3.45–3.55(bs, 8H), 6.8–6.9(d, 2H), 7.0–7.1 (d, 2H), 7.55–7.65(d, 2H), 8.1–8.2(d, 2H); MS: m/z 265 $(MH)^+$.

A solution of 1-(4-cyanophenyl)-4-(4-pyridyl)piperazine (1.8 g) in ethanol saturated with ammonia gas (150 ml) was hydrogenated at 150 atmospheres and 100° C. (using Raney Nickel as catalyst) in a high pressure hydrogenation apparatus for 18 hours. The solution was filtered through diatomaceous earth and the filtrate evaporated to give a solid which was purified by flash chromatography on alumina (ICN Alumina N 32–63) using a mixture of 95:5 dichloromethane:methanol as eluant. The residue was recrystallised from tetrahydrofuran/isohexane to give 1-(4-aminomethylphenyl)-4-(4-pyridyl)piperazine (1.3 g) m.p.168–170° C.; microanalysis, found: C,71.5; H,7.6; N,20.5%; $C_{16}H_{20}N_4$ requires: C,71.6; H,7.5; N,20.9%; NMR: 3.2–3.4(m,4H), 3.4–3.6(m,4H), 3.65(s,2H), 6.8–6.9 (d,2H), 6.9–7.0(d,2H), 7.15–7.25(d,2H), 8.15–8.25(d,2H); MS: m/z 269 $(MH)^+$.

EXAMPLE 2

4-Toluenesulphonyl chloride (95 mg) was added to a solution of 1-(4-aminophenyl)-4-(4-pyridyl)piperazine (127 mg) in dichloromethane (25 ml) and the mixture was stirred at ambient temperature for 16 hours. The resulting precipitate was collected by filtration and washed with dichloromethane. There was thus obtained 1-(4-pyridyl)-4-[4-methylsulphonamido)phenyl]piperazine hydrochloride as a grey solid (160 mg). mp. 293–294° C.; microanalysis, found: C,59.4; H,5.7; N,12.6; $C_{22}H_{24}N_4O_2S.HCl$ requires: C,59.1; H,5.8; N,12.6; NMR: 2.35(s,3H), 3.24(t,4H), 3.81 (t,4H), 6.84(d,2H), 6.96(d,2H), 7.24(d,2H) 7.33(d,2H), 7.58 (d,2H), 8.26(d,2H), 9.78(s,1H), 13.45(broad,1H); MS: m/z 409 $(MH)^+$.

EXAMPLE 3

4-Chlorostyrylsulphonyl chloride (118 mg) in dichloromethane (5 ml) was added to a solution of 1-(4-aminophenyl)-4-(4-pyridyl)piperazine (127 mg) in dichloromethane (5 ml) and stirred at ambient temperature for 2 hours. The resulting precipitate was collected by filtration, washed with dichloromethane then triturated with 10% methanol in dichloromethane. There was thus obtained (E)-1-(4-pyridyl)-4-[4-chlorostyrylsulphonamido] piperazine hydrochloride as a yellow solid (77 mg). mp. 285–287° C.; microanalysis, found: C,55.3; H,4.6; N,11.1; $C_{23}H_{23}ClN_4O_2S.HCl. 1/2H_2O$ requires: C,55.1; H,4.8; N,11.2; NMR: 3.24(m,4H), 3.81(m,4H), 6.92(d,2H), 7.11(d, 2H), 7.20(d,1H), 7.23(d,2H), 7.33(d,1H), 7.46(d,2H), 7.71 (d,2H), 8.24(d,2H), 9.65(s,1H), 13.25(broad,1H); MS: m/z 455 $(MH)^-$.

EXAMPLE 4

4-Dimethylamino-pyridine (30 mg) and 4-bromophenylsulphonl chloride (260 mg) was added to a solution of 1-(4-aminomethylphenyl)-4-(4-pyridyl) piperazine (268 mg) in pyridine(5 ml). The solution was heated on a steam bath for three hours. The solution was cooled to ambient temperature and evaporated. Water (100 ml) was added to the residue and the solution acidified to pH 1 by addition of concentrated hydrochloric acid. The aqueous solution was washed with ether (2×100 ml) and then basified by addition of aqueous ammonia.

The mixture was extracted with methylene chloride and the methylene chloride extracts were washed with water, brine, dried $(MgSO_4)$ and evaporated. The residue was recrystallised from a mixture of ethyl acetate/ tetrahydrofuran/isohexane to give 1-(4-pyridyl)-4-(4-bromophenylsulphonamidomethyl-phenyl)piperazine (155 mg.) as a solid m.p. 180–182° C.; microanalysis, found: C,54.4; H,4.8; N,11.3%; $C_{22}H_{23}BrN_4O_2S$ requires: C,54.2; H,4.7; N,11.5%; NMR: 3.15–3.3(m,4H), 3.4–3.55(m,4H), 3.85–3.95(d,2H), 6.8–6.9(bm,4H), 7.0–7.1(d,2H), 7.6–7.8 (q,4H), 8.05–8.15(t,2H), 8.18–8.25(bd,1H); MS: m/z 487 $(MH)^+$.

EXAMPLE 5

4-Cyanophenylsulphonyl chloride (202 mg) was added to a solution of 1-(4-aminomethylphenyl)-4-(4-pyridyl) piperazine (268 mg) in pyridine (20 ml). The mixture was heated on a steam bath for three hours. The solvents were removed by evaporation and water (100 ml) added to give a precipitate which was extracted into ethyl acetate (2×100 ml). The ethyl acetate extracts were combined, washed with water, brine, dried $(MgSO_4)$-10% methanol/methylene chloride as eluent to give a solid which was recrystallised from a mixture of tetrahydrofuran/methanol/isohexane to give 1-(4-pyridyl)-4-(4-cyanophenylsulphonamidomethyl-phenyl)piperazine (52 mg) as a solid m.p.229–230° C.; microanalysis found: C,62.8; H,5.6; N,15.7%; $C_{23}H_{23}N_5O_2S.0.25H_2O$ requires: C,62.4; H,5.4; N,15.8%; NMR: 3.15–3.3(m,4H), 3.4–3.55(m,4H), 3.85–4.0(d,2H), 6.8–6.9(dd,4H), 7.0–77.1(d,2H), 7.8–7.9(d,2H), 7.95–8.05 (d,2H), 8.18–8.25(d,2H), 8.25–8.4(bt,1H); MS: m/z 434 $(MH)^+$

EXAMPLE 6

4-Methoxybenzenesulphonyl chloride (0.25 g) was dissolved in dry tetrahydrofuran (2.0 ml) and treated with a warm solution of 1-(4-aminomethylphenyl)-4-(4-pyridyl) piperazine (0.27 g) in tetrahydrofuran (8.0 ml) and triethylamine (0.2 ml) in one portion. The reaction mixture was stirred overnight and then quenched by concentrating the reaction solution to a volume of 1 ml followed by the addition of 1 M solution of aq.$NaHCO_3$ (8 ml). The mixture was stirred for 2 hours. The resulting precipitate was collected by filtration, washed with water and dried to give 1-(4-pyridyl)-4-(4-methoxyphenylsulphonamidomethyl-phenyl)piperazine (0.29 g) as a solid m.p. 212–213° C.; microanalysis found: C,62.9; H,5.9; N,12.6%;

$C_{23}H_{26}N_4O_3S$ requires C,63.0; H,5.98; N,12.8%: NMR: 3.23(t,4H), 3.47(t,4H), 3.82(s,3H), 3.89(d,2H), 6.88(d,4H), 7.07(m,4H),7.71(dd,2H), 7.79(t,1H), 8.18(bs,2H); MS: m/z 439 (MH)$^+$.

EXAMPLE 7

A solution of 4-bromophenyl isocyanate (198 mg) in tetrahydrofuran was added dropwise to a solution of 1-(4-aminomethylphenyl)-4-(4-pyridyl)piperazine (268 mg) in tetrahydrofuran (50 ml). When the addition was complete, the solution was stirred at ambient temperature overnight. The precipitate was collected by filtration, filtered, washed with ether and recrystallised from methanol to give 1-(4-pyridyl)-4-(4-bromophenylureidomethyl-phenyl)piperazine (185 mg) as a solid, m.p. 258–260° C.; microanalysis found: C,59.1; H,5.3; N,14.8%; $C_{23}H_{24}BrN_5O$ requires: C,59.2; H,5.2; N,15.0%; NMR: 3.15–3.3(m,4H), 3.4–3.55(m,4H), 4.15–4.25(d,2H), 6.45–6.55(t,1H), 6.8–6.9(d,2H), 6.9–7.0 (d,2H), 7.15–7.25(d,2H), 7.38(s,4H), 8.18–8.25(d,2H), 8.6 (bs,1H); MS: m/z 466 (MH)$^+$.

EXAMPLE 8

A solution of 4-cyanophenyl isocyanate (144 mg) in tetrahydrofuran was added dropwise to a solution of 1-(4-aminomethylphenyl)-4-(4-pyridyl)piperazine (268 mg) in tetrahydrofuran (50 ml). When the addition was complete, the solution was stirred at ambient temperature overnight. The precipitate was collected by filtration, washed with ether and recrystallised from a mixture of tetrahydrofuran/methanol/isohexane to give 1-(4-pyridyl)-4-(4-cyanophenylureidomethyl-phenyl)piperazine (52 mg) as a solid, m.p. 254–255° C.; microanalysis, found: C,69.5; H,6.0; N,20.1%; $C_{24}H_{24}N_6O$ requires: C,69.9; H,5.9; N,20.4%; NMR: 3.15–3.3(m,4H), 3.4–3.55(m,4H), 4.15–4.25(d,2H), 6.65–6.75(t,1H), 6.80–6.90(d,2H), 6.90–7.00(d,2H), 7.15–7.25(d,2H), 7.50–0.70(q,4H), 8.18–8.25(d,2H), 9.0(bs,1H); MS: m/z 413 (MH)$^+$.

EXAMPLE 9

A solution of 4-bromobenzoyl chloride (240 mg) in dichloromethane (10 ml) was added dropwise to a stirred solution of 1-(4-aminomethylphenyl)-4-(4-pyridyl) piperazine (268 mg) in dichloromethane (50 ml) containing triethylamine (0.5 ml). The resulting solution was stirred at ambient temperature for three hours. The solution was poured into water and the solid which precipitated was collected by filtration and washed with water, acetone and recrystallised from methanol to give 1-(4-pyridyl)-4-(4-bromobenzoylamido-methylphenyl)piperazine (230 mg) as a solid, microanalysis, found: C,61.3; H,5.2; N,11.9%; $C_{23}H_{23}BrN_4O$ requires: C,61.2; H,5.14; N,12.4%; NMR: 3.15–3.3(m,4H), 3.4–3.55(m,4H), 4.35–4.45(d,2H,), 6.8–6.93(bm,2H), 6.90–7.00(d,2H), 7.15–7.25(d,2H), 7.6–7.7(d,2H), 7.75–7.85(d,2H), 8.10–8.25(b,2H), 8.90–9.00(bt,1H); MS: m/z 451 (MH)$^+$.

EXAMPLE 10

A solution of methanesulphonyl chloride (0.155 ml) in dichloromethane (10 ml) was added dropwise to a stirred solution of 1-(4-aminomethylphenyl)-4-(4-pyridyl) piperazine (536 mg) in dichloromethane (50 ml) containing triethylamine (0.5 ml). The resulting solution was stirred at ambient temperature for 7 hours. The solution was evaporated and the residue was extracted with ethyl acetate. The ethyl acetate extracts were washed with water, sodium bicarbonate solution, brine, dried (MgSO$_4$) and evaporated. The solid residue was recrystallised from methanol to give 1-(4-pyridyl)-4-(methanesulphonamidomethylphenyl) piperazine (356 mg) as a solid, m.p.236–238° C.; microanalysis found: C,59.3; H,6.4; N,16.2%; $C_{17}H_{22}N_4O_2S$ requires: C,58.8; H,6.4; N,16.2%; NMR: 2.8(s,3H), 3.15–3.3(m,4H), 3.4–3.55(m,4H), 4.00–4.10(d, 2H,), 6.80–6.90(d,2H), 6.90–7.00(d,2H), 7.15–7.25(d,2H), 7.3—7.5(t,1H), 8.20(d,1H); MS: m/z 311 (MH)$^+$.

EXAMPLE 11

Sodium hydride (55 mg) (50% dispersion in oil) was added to a stirred solution of 1-(4-pyridyl)-4-(4-toluenesulphonamidomethyl-phenyl)piperazine (422 mg) in dimethyl formamide (20 ml) under argon. The solution was stirred at 70–80° C. for 1 hour. The solution was cooled to ambient temperature and a solution of methyl iodide (150 mg) in dimethyl formamide (1 ml) was added dropwise. When the addition was complete, the solution was stirred at ambient temperature for 4 hours. Water (120 ml) was added and the solution extracted with hot ethyl acetate (2×100 ml). The combined extracts were washed with water, brine, dried (MgSO$_4$) and evaporated. A solid residue was recrystallised from a mixture of ethyl acetate/isohexane to give 1-(4-pyridyl)-4-(4-toluenesulphonamethylamidomethyl-phenyl) piperazine (65 mg) as a solid, m.p. 183–185° C.; microanalysis, found: C,65.7; H,6.5; N,12.3%; $C_{24}H_{28}N_4O_2S$ requires: C,66.0; H,6.46; N,12.8%; NMR: 2.43(s,3H), 3.2–3.35(m,4H), 3.4–3.55(m,4H), 4.0(s,2H), 6.9–7.0(d,2H), 7.1–7.2(d,2H), 7.4–7.5(d,2H), 7.7–7.8(d, 2H); MS: m/z 437 (MH)$^+$.

EXAMPLE 12

Triethylamine (0.43 ml) was added to a stirred suspension of 1-(4-anilinocarboxy)-4-(4-pyridyl)piperazine hydrochloride (356 mg) in dry DMF (4 ml). After 1 hour, 4-methylbenzenesulphonylchloride (210 mg) was added and stirring continued for 16 hours. The reaction mixture was diluted with dichloromethane (25 ml) and washed with water (2×7 ml), saturated brine (7 ml), dried (MgSO$_4$) and evaporated. The resulting oil, was purified by flash chromatography on silica gel using an increasing polar mixture of 2 to 10% v/v methanol in dichloromethane as eluant to give 1-(4-pyridyl)-4-(4-toluenesulphonamido-benzoyl) piperazine (94 mg), as a solid. m.p. 139–141° C.; microanalysis, found: C,61.5; H,5.9; N,12.4%; $C_{23}H_{24}N_4O_3S.0.5H_2O$ requires: C,61.9; H,5.6; N,12.6%; NMR: 2.34(3H, s), 3.40(4H,m), 3.57(4H,m), 6.80(2H,d), 7.14(2H,d), 7.33(4H, m), 7.70(2H,d), 8.18(2H, d), 10.55 (1H, bs); MS: m/z 437 (MH)$^+$.

The 1-(4-anilinocarboxy)-4-(4-pyridyl)piperazine hydrochloride used as starting material was prepared as follows:

10% w/w Palladium on charcoal (200 mg) was added to a solution of 1-(4-nitrobenzenecarboxy)-4-(4-pyridyl) piperazine (936 mg) in a mixture of dichloromethane (25 ml) and methanol (10 ml) containing 4.55M hydrogen chloride in dry ether (1.3 ml). The mixture was hydrogenated at ambient temperature and pressure until the theoretical amount of hydrogen had been taken up. The mixture was filtered through diatomaceous earth and the filtrate evaporated. Trituration of the resulting solid with ether gave 1-(4-anilinocarboxy)-4-(4-pyridyl)piperazine dihydrochloride (980 mg) as a pale yellow solid, m.p.>350° C.; microanalysis, found: C,54.1; H,5.8, N,15.7%; $C_{16}H_{18}N_4O.2HCl$ requires: C,54.1; H,5.7; N,15.8%; NMR: 3.67(4H,m), 3.78(4H,m), 3.3 to 4.5 (b), 6.97(2H,d), 7.19 (2H,d), 7.37(2H,d), 8.29(2H,d); MS: m/z 283 (MH)$^+$.

EXAMPLE 13

To a stirred cooled (0° C.) solution of 4-(naphthalene-2-sulphonyl)benzoic acid (312 mg) in DMF (4 ml), was added 1,1'-carbonyldiimidazole (162 mg. The mixture was stirred at 0° C. for 30 minutes and then N-(4-pyridyl)piperazine (163 mg) was added. The cooling bath was removed and the mixture was stirred at room temperature overnight. The solvent was removed by evaporation under high vacuum. The residue was dissolved in a mixture of ethyl acetate and water. The ethyl acetate extract was dried ($MgSO_4$) and evaporated to give a solid residue (70 mg), which was recrystallised from a mixture of methanol, ethyl acetate and isohexane to afford 1-(4-pyridyl)-4-(4-naphthalene-2-sulphonyl)benzoyl)piperazine (124 mg) as white needles. NMR: 3.25–3.5(m,6H); 3.6–3.9(m,2H); 6.8(d,2H); 7.7(d, 2H); 7.77(dd,1H); 7.95(dd,1H); 8.05–825(m,8H); 8.77(d, 1H); microanalysis: found C,63.5; H,5.5; N,8.5%; $C_{26}H_{23}N_3O_3S.2H_2O$ requires C,63.5; H,5.5; N,8.6; MS: m/z 457 $(MH)^+$.

The 4-(naphthalene-2-sulphonyl)-benzoic acid used as starting material was prepared as follows:

4-(Naphthalene-2-sulphonyl)benzaldehyde (0.97 g) was suspended in water (25 ml) containing cetyltrimethylammonium bromide (58 mg). The mixture was stirred and heated to 60° C., and potassium permanganate (0.95 g) was added in small portions over 1 hour. Heating was continued for a further 2 hours. The mixture was cooled to room temperature and was acidified with 2M hydrochloric acid. Ethyl acetate was added to the stirred mixture, which was filtered through a pad of celite. The ethyl acetate layer was washed with brine, dried ($MgSO_4$), and evaporated to afford 4-(naphthalene-2-sulphonyl)benzoic acid (0.42 g) as solid residue; NMR: 7.7(dd,1H); 7.95(dd,1H), 8.1–8.2(m,8H); 8.7(d,1H); microanalysis, found; C,58.6; H,3.9%; $C_{17}H_{12}O_4S.2H_2O$ requires: C,58.6; H,4.6%; MS: m/z 312$(MH)^+$.

EXAMPLE 14

Carbonyl diimidazole (340 mg) was added to a solution of 4-benzoylbenzoic acid (440 mg) in dimethylformamide (10 ml). After stirring at ambient temperature for 45 minutes, N-(4-pyridyl)piperazine (326 mg) was added as a solid, in one portion and stirring continued at ambient temperature overnight. The reaction mixture was poured into water (50 ml) and extracted with ethyl acetate (3×20 ml). The extracts were combined, washed with water, brine, dried ($MgSO_4$) and evaporated to give a solid which was purified by recrystallisation from a mixture of ethyl acetate, methanol and hexane (10/3/9) to give 1-(4-pyridyl)-4-(4-benzoylbenzoyl)piperazinie as pale yellow crystals (660 mg), m.p. 153–154° C.; microanalysis, found: C,74.5; H,5.6; N,11.3%; $C_{23}H_{21}N_3O_2$ requires: C,74.4; H,5.7; N, 11.3%; NMR: 3.3–3.9(m,8H), 6.9(d,2H), 7.5–7.9(m,9H), 8.2(d,2H); MS: m/z 372 $(MH)^+$.

EXAMPLE 15

To a solution of 4-phenoxybenzaldehyde (198 mg) in dichloromethane (20 ml), N-(4-pyridyl)piperazine (163 mg) and acetic acid (240 mg) were added. The mixture was stirred at ambient temperature for 30 mins, and then sodium triacetoxyborohydride (318 mg) was added in one portion. Stirring was continued at ambient temperature overnight. The reaction mixture was poured into 1M hydrochloric acid (50 ml) and washed With ethyl acetate (50 ml). The aqueous layer was made basic with 2M sodium hydroxide solution and extracted with dichloromethane (2×25 ml). The combined extracts were washed with water, dried ($MgSO_4$) and evaporated to give a white solid which was purified by chromatography on silica gel (Mega Bond Elut column) using an increasing concentration of methanol in dichloromethane (up to 4% methanol) as eluant to give 1-(4-pyridyl)-4-(4-phenoxy-phenyl)piperazine (168 mg) as a solid: microanalysis, found: C,76.5; H,6.6; N,11.9%; $C_{22}H_{23}N_3O$ requires: C,76.5; H,6.7; N,12.2%; NMR: 3.2–3.45(m,8H); 3.5(s,2H); 6.8(d,2H); 6.9–7.05(m,4H); 7.1–7.2(m,1H); 7.25–7.45(m,4H); 8.1(d,2H); MS: m/z 345 $(MH)^+$.

EXAMPLE 16

A solution of N-(4-pyridyl)piperazine (0.33 g) in dry dimethylformamide (15 ml) was treated with sodium hydride (0.14 g) (45–55% dispersion in oil). The reaction mixture was then stirred for 45 minutes at ambient temperature under argon. 4-Bromobenzyl bromide (0.58 g) was added and the mixture heated slowly to 60° C. and then maintained at this temperature for 2 hours. The resulting mixture was then poured into water, basified with aq.$NaHCO_3$ solution and then extracted with diethyl ether. The organic extracts were then washed with aq.$NaHCO_3$, water, brine, dried ($Na_2SO_4$) and evaporated. The residue was recrystallised from acetonitrile to give 1-(4-pyridyl)-4-(4-bromobenzyl)piperazine (0.2 g) as a solid, m.p. 140–141° C.; microanalysis, found: C,55.3; H,5.2; N,12.0%; $C_{16}H_{18}N_3Br$ requires: C,55.4; H,5.7; N,12.1%; NMR: ($CDCl_3$) 2.54(t,4H); 3.2(t,4H); 3.51(s,2H); 6.66(d,2H); 7.23 (d,2H); 7.46(d,2H); 8.29(d,2H); MS: m/z 332 $(MH)^+$.

EXAMPLE 17

A solution of N-(4-pyridyl)piperazine (0.33 g) in dry dimethylformamide (15 ml) was treated with sodium hydride (0.14 g) (45–55% dispersion in oil). The reaction mixture was then stirred for 30 minutes at ambient temperature under argon. 4-Cyanobenzyl bromide (0.41 g) was added and the mixture heated slowly to 80° C. and then maintained at this temperature for 2 hours. The resulting mixture was then poured into water, basified with aq.$NaHCO_3$ solution and then extracted with diethyl ether. The organic extracts were then washed with aq.$NaHCO_3$, water. brine, dried ($MgSO_4$) and evaporated. The residue was recrystallised from toluene/hexane to give 1-(4-pyridyl)-4-(4-cyanobenzyl)piperazine (0.08 g) as a solid. m.p. 137–138° C.; microanalysis, found: C, 73.3; H, 6.5; N, 19.8%; $C_{17}H_{18}N_4$ requires: C, 73.4; H, 6.5; N, 20.1%; NMR: ($CDCl_3$) 2.56(t,4H); 3.35(t,4H); 3.61(s,2H); 6.67(dd, 2H); 7.49(d,2H); 7.63(d,2H); 8.28(dd,2H); MS: m/z 279 $(MH)^+$.

EXAMPLE 18

A solution of N-(4-pyridyl)piperazine (0.33 g) in dry dimethylformamide (15 ml) was treated with sodium hydride (0.14 g) (45–55% dispersion in oil). The reaction mixture was then stirred for 30 minutes at ambient temperature under argon. A solution of 2-fluoro-4-bromobenzyl bromide (2.6 ml) (20% w/v in dichlorobenzene) was added and the mixture was heated slowly to 70° C. and then maintained at this temperature for 24 hours. The resulting mixture was then poured into water and then extracted with diethyl ether. The organic extracts were then washed with aq.$NaHCO_3$, water, brine, dried ($Na_2SO_4$) and evaporated. The residue was then purified by flash chromatography on alumina (ICN Alumina N 32–63) using an increasing concentration of ethyl acetate in isohexane (50–100% ethyl acetate) and then up to 10% methanol in ethyl acetate as eluent to give after recrystallisation 1-(4-pyridyl)-4-(2-fluoro-4-bromobenzyl)piperazine (0.08 g) as a solid, m.p. 77–78° C.; microanalysis, found: C, 54.4; H, 4.8; N, 11.1%; $C_{16}H_{17}N_3FBr$ requires: C, 54.9; H, 4.9; N, 12.0%; NMR: 3.28(s,8H), 3.54(s,2H); 6.79(d,2H); 7.41(d,2H); 7.52(d,1H); 8.13(d,2H); MS: m/z 350 (MH)$^+$.

EXAMPLE 19

Using an analogous procedure to that described in Example 16, but using 3,4-dichlorobenzylbromide as starting material was prepared 1-pyridyl-4-(3,4-dichlorobenzyl)piperazine (43% yield), microanalysis, found: C, 59.3; H, 5.4; N, 12.75%; $C_{16}H_{17}Cl_2N_3$ requires C, 59.6; H, 5.3; N, 13.0%; NMR: 2.4–2.45 (m,4H), 3.3–3.45 (m,4H), 3.55 (s,2H), 6.6 (d,2H), 7.3–7.4 (dd,1H), 7.55–7.65 (m,2H), 8.15 (d,2H); MS m/z 322 (MH)$^+$.

EXAMPLE 20

Using an analogous procedure to that described in Example 16, but using 4-nitrobenzylbromide as starting material, was prepared 1-pyridyl-4-(4-nitrobenzyl)piperazine (47% yield), NMR: 3.7 (s,2H), 6.8 (d,2H), 7.65 (d,2H), 8.15 (d,2H), 8.2 (d,2H); MS: m/z 299 (MH)$^+$.

EXAMPLE 21

1-(4-Pyridyl)piperazine (9.78 g) and 1-bromo-4-nitrobenzene (6.67 g) were stirred as a melt at 120° C. for 1 hour. The mixture was cooled to ambient temperature and 5% methanol in dichloromethane (100 ml) was added. The solid mass broken up by sonication and the mixture was stirred for 16 hours. The resulting solid was collected by filtration and purified by flash chromatography on silica gel using a gradient of 5–15% methanol/0.1% ammonia (SG. 0.88) in dichloromethane as eluant to give a product of sufficient purity to continue (6.35 g) m.p. 225–226° C.

A solution of this solid (1.0 g) in concentrated hydrochloric acid (10 ml) was treated with granulated zinc (0.5 g) and stirred at 110° C. for 2 hours. Water (50 ml) was added to the mixture and unreacted zinc was removed by filtration. The product hydrochloride precipitated from the filtrate on cooling. This solid was collected, dissolved in 20% potassium hydroxide, extracted with dichloromethane (4×25 ml), washed with water, brine, dried (MgSO$_4$) and evaporated. There was thus obtained 1-(4-aminophenyl)-4-(4-pyridyl)piperazine as a free base (0.88 g), microanalysis, found: C, 70.8; H, 7.1; N, 22.0; $C_{15}H_{18}N_4$ requires: C, 71.0; H, 7.3; N, 22.0; NMR: 3.01(t,4H), 3.41(t,4H), 6.52(d,2H), 6.75(d,2H), 6.86(d,2H), 8.17(d,2H); MS: m/z 255 (MH)$^+$.

EXAMPLE 22

A solution of 1-(4-pyridyl)piperazine (0.49 g) in dry dichloromethane (20 ml) and triethylamine (0.7 ml) was treated slowly with a solution of 4-bromobenzoyl chloride (0.7 g) in dry dichloromethane (10 ml). The reaction mixture was then stirred under argon for 2 hours. The dichloromethane solvent was removed by evaporation and the residue dissolved in ethyl acetate. The organic extracts were then washed with aqueous sodium hydrogen carbonate solution, water, brine, dried (Na$_2$SO$_4$) and evaporated to yield a colourless oil. The residual oil was then triturated with diethyl ether and recrystallised from ethyl acetate/isohexane to give 1-(4-pyridyl)-4-(4-bromobenzoyl)piperazine (0.62 g) as a solid, m.p. 128–129° C.; microanalysis, found: C, 55.7; H, 4.7; N, 12.0%; $C_{16}H_{16}N_3OBr$ requires: C, 55.5; H, 4.7; N, 12.1%; NMR: (CDCl$_3$) 3.36(s,4H), 3.73(s,4H), 6.67(dd,2H), 7.33(dd,2H), 7.58(dd,2H), 8.34(dd,2H); MS: m/z 346 (MH)$^+$.

EXAMPLE 23

A solution of 1-(4-pyridyl)piperazine (0.49 g) in dry dichloromethane (20 ml) and triethylamine (0.7 ml) was treated slowly with a solution of 4-cyanobenzoyl chloride (0.50 g) in dry dichloromethane (30ml). The reaction mixture was then stirred under argon for 2 hours. The dichloromethane solvent was removed by evaporation and the residue dissolved in ethyl acetate. The organic extracts were then washed with aqueous sodium hydrogen carbonate solution, water, brine, dried (Na$_2$SO$_4$) and evaporated to give a colourless oil which was crystallised from ethyl acetate/isohexane to afford 1-(4-pyridyl)4-(4-cyanobenzoyl)piperazine (0.25 g) as a solid, m.p. 164–165° C.; microanalysis, found: C, 69.7; H, 5.6; N, 18.5%; $C_{17}H_{16}N_4O$ requires: C, 69.8; H, 5.52; N, 19.2%; NMR: (CDCl$_3$) 3.38(bs,4H), 3.75(bs,4H), 6.67(dd,2H), 7.56(dd, 2H), 7.76(dd,2H), 8.32(dd,2H): MS: m/z 293 (MH)$^+$.

EXAMPLE 24

A solution of 2-fluoro-4-bromobenzoic acid (0.24 g) in dry dimethylformamide (10 ml) was treated with 1-(3-dimethylaminopropyl)-3-ethylcarbodiimide hydrochloride (0.17 g) and stirred for 30 minutes at ambient temperature under argon. A solution of 1-(4-pyridyl)piperazine (1.6 g) in dry dimethylformamide (3 ml) was added to the mixture and the mixture cooled to 50° C. The reaction was then allowed to warm to room temperature and stirred overnight. The solution was poured into water and then extracted into diethyl ether, washed with aqueous sodium hydrogen carbonate solution, water, brine. dried (Na$_2$SO$_4$) and evaporated to yield a colourless oil. This oil was then triturated with diethyl ether and recrystallised from ethyl acetate/isohexane to give 1-(4-pyridyl)-4-(2-fluoro-4-bromobenzoyl)piperazine (0.14 g) as a solid, m.p. 125–126° C.: microanalysis, found: C, 52.6; H, 4.1; N, 11.2%; $C_{16}H_{15}BrFN_3O$ requires: C, 52.8; H, 4.15; N, 11.5%; NMR: (CDCl$_3$) 3.32(t,2H), 3.46(t,4H), 3.94(t,2H), 6.68(dd,2H), 7.29–7.43(m,3H), 8.33(d,2H); MS: m/z 364 (MH)$^+$.

EXAMPLE 25

A solution of 1-(4-pyridyl)piperazine (0.49 g) and triethylamine (0.7 ml) in dry dichloromethane (20 ml) was treated slowly with a solution of 4-bromophenylsulphonyl chloride (0.77 g) in dry dichloromethane (10 ml). The reaction mixture was then stirred under argon for 2 hours. The dichloromethane solvent was removed by evaporation and the residue dissolved in ethyl acetate. The organic extracts were washed with water, brine, dried (MgSO$_4$) and evaporated to yield a white crystalline solid which was recrystallised from ethyl acetate to give 1-(4-pyridyl)-4-(4-bromophenylsulphonyl)piperazine (0.84 g) as a solid, m.p. 199–200° C.: microanalysis, found: C, 47.3; H, 4.1; N, 10.9%; $C_{15}H_{16}BrN_3O_2S$ requires: C, 47.1; H, 4.22; N, 11.0%; NMR: (CDCl$_3$) 3.13(t,4H), 3.42(t,4H), 6.62(dd,2H), 7.67(q,4H), 8.29(d,2H): MS: m/z 382 (MH)$^-$.

EXAMPLE 26

Pyridine (1 ml) was added to a solution of 1-(4-pyridyl)piperazine (0.33 g) in dry dichloromethane (20 ml) and triethylamine (1 ml) at 5° C. The reaction mixture was treated with 4-cyanobenzenesulphonyl chloride (0.40 g). The reaction mixture was then stirred under argon for 4 hours allowing to warm to room temperature. The dichloromethane solvent was removed by evaporation and the residual pyridine solution poured into aqueous sodium hydrogen carbonate solution and then extracted with ethyl acetate. The organic extracts were then washed with aqueous sodium hydrogen carbonate solution, water, brine, dried (MgSO$_4$) and evaporated to yield a pale cream solid which was then recrystallised from ethyl acetate isohexane to give 1-(4-pyridyl)-4-(4-cyanophenylsulphonyl)piperazine (0.31 g) as a solid. m.p. 212–213° C.; microanalysis, found: C, 58.8; H, 4.9; N, 17.1%; C$_{16}$H$_{16}$N$_4$O$_2$S requires: C, 8.5: H, 4.91; N, 17.1%; NMR: (CDCl$_3$) 3.18(t,4H), 3.44(t,4H), 6.62(dd,2H), 7.88(q,4H), 8.30(dd,2H); MS: m/z 329 (MH)$^+$.

EXAMPLE 27

1-(4-Pyridyl)-4-(4-aminophenyl)piperazine (0.4 g) was dissolved in dry dichloromethane (40 ml) and cooled to 0° C. Triethylamine (0.4 ml) was added followed by 4-cyanobenzenesulphonyl chloride (0.6 g). The reaction mixture was then stirred overnight. The mixture was washed with aqueous sodium hydrogen carbonate solution. water, brine, dried (MgSO$_4$) and evaporated to yield the crude solid product. This solid was purified by flash chromatography on ICN Alumina (N 32–63) using and increasing concentrations of ethyl acetate in isohexane (50–100% ethyl acetate) and up to 10% methanol in ethyl acetate as the eluent to give 1-(4-pyridyl)-4-(4-cyanophenylsulphonamidophenyl) piperazine (0.12 g) as a solid, m.p. 237–238° C.; microanalysis found: C, 61.4; H, 4.9; N, 15.5%; C$_{22}$H$_{21}$N$_5$O$_2$S.0.5 H$_2$O requires: C, 61.7; H, 4.9; N, 16.3%; NMR: 3.17(t,4H), 3.42(t,4H), 6.81–6.97(m,6H), 7.82(d,2H), 8.02(d,2H), 8.18(d,2H,: MS: m/z 420 (MH)$^+$.

The 1-(4-pyridyl)-4-(4-aminophenyl)piperazine used as starting material was prepared as follows:

Sodium hydride (0.5 g) (45–55% dispersion in oil was added to a solution of 1-(4-pyridyl)piperazine (0.9 g) in dry dimethylformamide (10 ml) at ambient temperature and stirred for 30 minutes. After this time, 4-fluoronitrobenzene (0.65 ml) was added slowly and the temperature raised to 70° C. The mixture was maintained at this temperature for 2 hours. The reaction mixture was then quenched by pouring into water and acidifying with aq 2N HCl solution to pH 1. The acidic layer was washed with diethyl ether and then basified with aq 2N.NaOH solution. The resulting precipitate was filtered, washed with water, dissolved in methanol, filtered through phase separator paper and evaporated to dryness. The resulting crude material was recrystallised from methanol/ether to give 1-(4-pyridyl)-4-(4nitrophenyl) piperazine (0.64 g) as an oil, NMR: (CDCl$_3$) 3.61(q,8H), 6.58(d,2H), 6.81(d,2H), 8.16(d,2H), 8.33(bs,2H); MS: m/z 285 (MH)$^+$.

A solution of sodium dithionite (2.5 g) in water (10 ml) was added to a warmed solution of 1-(4-pyridyl)-4-(4-nitrophenyl)piperazine (0.551 g) in methanol (50 ml) and the mixture was allowed to reflux for 2 hours. The methanol was removed by evaporation and the resulting concentrated solution was basified with solid Na$_2$SO$_4$. The organic material was extracted into ethyl acetate, washed with water, brine, dried (Na$_2$SO$_4$) and evaporated to give 1-(4-pyridyl)-4-(4-aminophenyl)piperazine (0.4 g) as an oil. NMR: (CDCl$_3$) 3.14(t,4H), 3.48(t, 4H), 6.68(m,4H), 6.85(d,2H), 8.31(bd,2H): MS: m z 255 (MH)$^-$.

EXAMPLE 28

A solution of 4-chloropyrimidine HCl (450mg) and 4-bromophenyl sulphonyl piperazine (300 mg) in ethanol (20 ml) and water (2 ml) containing triethylamine (0.5 ml) was heated under reflux overnight. The solution was evaporated and water (50 ml) added and the solution basified to pH 8 by addition of solid potassium carbonate to give a precipitate which was filtered and washed with water and air dried. The crude solid was dissolved in acetonitrile and chromatographed on an alumina column (ICN Alumina N 32-63) eluting with 30% tetrahydrofuran/ethyl acetate and then acetonitrile to give pure product which was recrystallised from a mixture of ethyl acetate/isohexane to give 1-(4-pyrimidyl)-4-(4-bromophensulphonyl)piperazine (44 mg) as a solid, m.p. 196–197° C.; microanalysis found: C, 43.9; H, 3.9; N, 14.4%; C$_{14}$H$_{15}$BrN$_4$O$_2$S requires: C, 43.9; H, 3.9; N, 14.6%; NMR: 2.9–3.1(m,4H), 3.6–3.8(m,4H), 6.8(dd,1H), 7.6–7.7(d,2H), 7.8–7.9(d,2H), 8.1–8.2(d,1H), 8.5(s,1H); MS: m/z 383 (MH)$^+$.

The 1-(4-bromophenylsulphonyl)piperazine used as starting material was prepared as follows:

To a stirred solution of piperazine (10.8 g) in dry dichloromethane (160 ml) and triethylamine (20 ml) at 0° C. was added slowly a solution of 4-bromobenzenesulphonyl chloride (16 g) in dichloromethane (80 ml) and stirred for 24 hours. The reaction was then quenched by removal of the dichloromethane solvent by evaporation, taken up in water and extracted with ethyl acetate. The organic extracts were washed with aqueous sodium hydrogen carbonate solution, water, brine, dried (MgSO$_4$) and then evaporated to give a white crystalline solid which was recrystallised from ethyl acetate/isohexane to afford 1-(4-bromophenylsulphonyl) piperazine (14.1 g) as a solid, m.p. 102–104° C.; microanalysis found: C, 39.5; H, 4.4; N, 9.1%: C$_{10}$H$_{13}$BrN$_2$O$_2$S requires: C, 39.4; H, 4.3; N, 9.2%; NMR (CDCl$_3$): 1.52(s,1H), 2.97(dt,8H), 7.61(d,2H), 7.69(d,2H): MS m/z 305 (MH)$^+$.

EXAMPLE 29

Carbonyl diimidazole (324 mg) was added to a solution of 6-bromonaphthalene-2-sulphinic acid (658 mg) in dimethylformamide (10 ml). After stirring at ambient temperature for one hour N-4-(4-pyridyl)piperazine (326 mg) was added as a solid in one portion and stirring continued at ambient temperature overnight. The reaction mixture was poured into ethyl acetate (100 ml), washed with water (3×25 ml), brine (25 ml), dried (MgSO$_4$) and evaporated to give a yellow oil which was purified by chromatography on silica gel (Mega Bond Elut column) using an increasing concentration of methanol in dichloromethane (up to 5% methanol) as eluant to give an oil which on trituration with diethyl ether gave a white solid 1-(4-pyridyl)-4-(6-bromonaphtalene-2-sulphenyl)piperazine (170 mg), m.p. 200–202° C.; microanalysis, found: C, 54.9; H, 4.4; N, 10.1; C$_{19}$H$_{18}$BrN$_3$OS requires: C, 54.9; H, 4.3; N, 10.1; NMR: 2.9–3.0(m,2H); 3.1–3.3(m,2H); 3.35–3.5(m,4H); 6.8(dd, 2H); 7.7–7.8(m,2H); 8.1–8.2(m,4H); 8.3(s,1H); 8.35(d,1H); MS: m/z 416 (MH)$^+$.

EXAMPLE 30

Triethylamine (3.48 ml) was added to a stirred suspension of 1-(4-pyridyl)piperazine (4.08 g) in DMF (50 ml). The mixture was cooled to 4° C., and 4-nitrobenzoylchloride (4.64 g) added. The mixture was stirred for 1 hour at 4° C. and then for 16 hours at ambient temperature. Dichloromethane (250 ml) was then added and the mixture washed with water (3×30 ml), saturated brine (1×30 ml), then dried (MgSO$_4$) and the solvents evaporated. The residual oil was purified by flash chromatography on silica gel using 5% v/v methanol/dichloromethane and then with 10% v/v methanol/dichloromethane as eluant to give 1-(4pyridyl)-4-(4-nitrobenzoyl)piperazine (5.09 g) as a yellow solid. m.p. 158–160° C.; microanalysis. found: C, 61.3; H, 5.3; N, 17.6%; $C_{16}H_{16}N_4O_3$ requires: C, 61.5; H, 5.2; N, 17.9%; NMR: 3.42(6H+$H_2$O,m), 3.87(2H,bs), 6.93(2H,d), 7.84(2H, d), 8.30(2H,d), 8.41(2H,d): MS: m/z 313 (MH)$^+$.

EXAMPLE 31

Azodicarbonyldipiperidine (20.03 g), tributylphosphine (16.06 g) and 1-(4-pyridyl)-4-piperidin-1-ol (9.43 g) were added to a stirred solution of N-t-butyloxycarbonyl-4-aminophenol (11.08 g) in dry THF (300 ml), cooled under a blanket of nitrogen to 10° C. A thick precipitate formed and the mixture was stirred at ambient temperature for 20 hours during which time the mixture slowly thinned. The precipitated tributylphosphine oxide was removed by filtration and the residue concentrated in vacuo. The residue was purified by flash chromatography on silica gel using ethyl acetate followed by dichloromethane containing an increasing amount of methanol (up to 5% methanol) as eluent to give a solid (7.38 g). mp 192–195° C.

A solution of this solid (4.22 g) in dichloromethane (400 ml) was treated with a saturated solution of hydrogen chloride in ether (50 ml) and the mixture was stirred for 64 hours. The mixture concentrated in vacuo and the residue crystallised from methanol/ether to give 1-(4-pyridyl)-4-(4-aminophenyloxy)piperidine hydrochloride (2.85 g), mp. 289–291° C. NMR: 1.73 (m,2H), 2.06 (m,2H), 3.64 (m,2H), 3.94(m,2H), 4.76 (m,1H), 7.12(d,2H), 7.24(d,2H), 7.34(d, 2H), 8.23(d,2H), 10.32 (broad, 2H); MS: m/z 270 (MH)$^+$. This solid (1.5 g) was dissolved in water (10 ml) and 2M sodium hydroxide added until precipitation was complete. There was thus obtained 1-(4-pyridyl)-4-(4-aminophenoxy) piperidine free base as a brown solid (1.03 g) mp 214–215° C. NMR: 1.57 (m,2H), 1.86 (m,2H), 3.24 (m,2H), 3.67(m, 2H), 4.31 (m,1H), 6.47(d,2H), 6.66(d,2H), 6.87(d,2H), 8.13 (d, 2H); MS: m/z 270 (MH)$^+$.

EXAMPLE 32

A solution of N-(4-pyridyl)piperazine (815 mg), 4-fluorobenzophenone (1.2 g) and powdered potassium carbonate (912 mg) was stirred at 95° C. in DMSO (10 ml) overnight. The solution was poured into water (150 ml) and extracted with dichloromethane (3×50 ml). The dichloromethane extracts were combined, washed with water, dried ($Na_2SO_4$) and evaporated. The residue was purified by chromatography on alumina (ICN Alumina N 32–63) using 1% methanol in dichloromethane as eluant to give a solid. The solid was recrystallised from a mixture of ethyl acetate/ isohexane to give 1-(4-benzoylphenyl)-4-(4-pyridyl) piperazine (450 mg) as a solid. m.p.136–137° C.

EXAMPLE 33

A solution of N-(4-pyridyl)piperazine (8.15 g), 4,4'-difluorobenzophenone (13.1 g) and powdered potassium carbonate (9.12 g) was stirred at 95° C. in DMSO (100 ml) overnight. The solution was poured into water (1500 ml) to give a precipitate which was filtered, washed with water and dried. The solid (7.82 g) was stirred in trifluoroacetic acid (25 ml) under argon with triethylsilane (10 ml) for 18 hours. The solution was poured into water (315 ml), taken to pH 12 with sodium hydroxide solution and extracted with dichloromethane (2×300 ml). The combined dichloromethane extracts were washed with water, dried ($Na_2SO_4$) and evaporated to give a residue which was purified by chromatography on alumina (ICN Alumina N 32–63) using 0.5% methanol in dichloromethane as eluant. The solid obtained was recrystallised from a mixture of ethyl acetate/isohexane to give 1-(4-fluorobenzylphenyl)-4-(4-pyridyl)piperazine (350 mg) as a solid, m.p. 110–111° C.

EXAMPLE 34

A solution of 1-(4-hydroxyphenyl)-4-(4-pyridyl) piperazine (670 mg), 4-fluorobenzonitrile (354 mg) and powdered potassium carbonate (445 mg) was stirred at 95° C. in DMSO (12 ml) for 18 hours. The solution was poured into water (180 ml) to give a precipitate which was filtered, washed with water and dried. The solid was purified by chromatography on alumina (ICN Alumina N 32-63) using 1% methanol in dichloromethane as eluant. This gave a solid which was recrystallised from a mixture of ethyl acetate/ isohexane to give 1-(4-cyanophenoxyphenyl)-4-(4-pyridyl) piperazine (126 mg) as a solid. m.p. 180–182° C.

The 1-(4-hydroxyphenyl)-4-(4-pyridyl)piperazine used as starting material was prepared as follows:

A solution of 4-chloropyridine HCl (450 mg) and 1-(4-methoxyphenyl)-piperazine (226 mg) in ethanol (20 ml) and water (2 ml) containing triethylamine (0.5 ml) was heated under reflux for 18 hours. The solution was evaporated, water (50 ml) added and the solution taken to pH 8 by addition of solid potassium carbonate to give a precipitate which was filtered, washed with water and dried. The solid (33 mg) was stirred in concentrated aqueous hydrogen bromide (2 ml) at 140° C. for 8 hours, poured into cold water (2 ml) and taken to pH 7 with aqueous ammonia (1.3 ml) to give a solid which was filtered, washed with water and dried to give 1-(4-hydroxyphenyl)-4-(4-pyridyl)piperazine (28 mg), m.p. 288–290° C.

EXAMPLE 35

Using an analogous procedure to that described in Example 34, but using 2-bromo-5-nitropyridine as starting material in place of 4-fluorobenzonitrile, there was prepared 1-(4-[5-nitro-2-pyridyloxy]phenyl)4-(4-pyridyl)piperazine (50% yield), m.p. 174–175° C.

EXAMPLE 36

Sodium hydride (120 mg) (50% dispersion in oil) was added to a stirred solution of 1-(4-hydroxyphenyl)-4-(4-pyridyl)piperazine (510 mg) in dimethylformamide (5 ml) under argon. The solution was stirred at ambient temperature for 30 minutes and a solution of 4-cyanobenzylbromide (430 mg) in dimethyl formamide (5 ml) was added dropwise. The solution was stirred at ambient temperature overnight, water (150 ml) added to give a precipitate which was washed with water, dried and recrystallised from ethanol to give 1-(4-cyanobenzyloxyphenyl)-4-(4-pyridyl)piperazine (660 mg), m.p.212–214° C.

EXAMPLE 37

Using an analogous procedure to that described in Example 36, but using 4-bromobenzylbromide as starting material in place of 4-cyanobenzylbromide, was prepared 1-(4-bromobenzyloxyphenyl)-4-(4-pyridyl)piperazine (50% yield), m.p.233–235° C.

EXAMPLE 38

A solution of 1-(4-formylphenyl)-4-(4-pyridyl)piperazine (1.0 g), 4-bromoacetophenone (745 mg) and conc. sodium hydroxide (3 drops) in ethanol (25 ml) was stirred at ambient temperature overnight to give a solid which was filtered, washed with ethanol and dried to give 1-(4-[4-bromobenzoylethylenyl]-phenyl)-4-(4-pyridyl)piperazine (900 mg), m.p. 201–203° C.

The 1-(4-formylphenyl)-4-(4-pyridyl)piperazine used as starting material was prepared as in Example 32, using 4-fluorobenzaldehyde as starting material in place of 4-fluorobenzophenone to give 1-(4-formylphenyl)-4-(4-pyridyl)piperazine (43% yield), m.p.116–118° C.

EXAMPLE 39

A solution of 1-(4-formylphenyl)-4-(4-pyridyl)piperazine (1.0 g), 4-methoxyacetophenone (503 mg) and concentrated sodium hydroxide (3 drops) in ethanol (25 ml) was stirred at ambient temperature overnight to give a solid which was dissolved in ethanol (100 ml) and hydrogenated over 10% palladium on charcoal to give a solid which was recrystallised from a mixture of ethyl acetate/isohexane to give 1-(4-[4-methylbenzoylethyl]-phenyl)-4-(4-pyridyl) piperazine (400 mg), m.p. 114–115° C.

EXAMPLE 40

4-Methoxybenzyltriphenylphosphonium bromide (4.47 g) was added to a solution of potassium t-butoxide (1.12 g) in tetrahydrofuran (50 ml) under argon. After 30 minutes at ambient temperature, the solution was treated with a solution of 1-(4-formylphenyl)-4-(4-pyridyl)piperazine (1.34 g) in tetrahydrofuran (25 ml) and the mixture stirred at ambient temperature overnight. The tetrahydrofuran was evaporated, the residue treated with water (100 ml) and extracted with dichloromethane (3×50 ml). The combined dichloromethane extracts were washed with water, dried ($Na_2SO_4$) and evaporated to give a residue which was purified by chromatography on alumina (ICN Alumina N 32–63) using 2% methanol in dichloromethane as eluent. This gave a solid which was recrystallised from a mixture of ethyl acetate/isohexane to give 1-[4-(4-methylphenylethylenyl)phenyl]-4-(4-pyridyl) piperazine (350 mg) as a solid. m.p. 92–94° C.

EXAMPLE 41

Using an analogous procedure to that described in Example 40, but using 4-cyanobenzyltriphenylphosphonium chloride as starting material in place of 4-methoxybenzyltriphenylphosphonium bromide, there was prepared 1-(4-[4-cyanophenylethylenyl]phenyl)-4-(4-pyridyl)piperazine (18% yield), m.p. 105–106° C.

EXAMPLE 42

A solution of 1-(4-acetylphenyl)-4-(4-pyridyl)piperazine (1.0 g), benzaldehyde (177 mg) and concentrated sodium hydroxide (3 drops) in ethanol (25 ml) was stirred at ambient temperature overnight to give a solid which was filtered, washed with ethanol and dried to give 1-(4-cinnamoylphenyl)-4-(4-pyridyl)piperazine (310 mg), m.p. 208–210° C.

The 1-(4-acetylphenyl)-4-(4-pyridyl)piperazine used as starting material was prepared as in Example 32, using 4-fluoroacetophenone as starting material in place of 4-fluorobenzophenone to give 1-(4-acetylphenyl)-4-(4-pyridyl)piperazine (40% yield), m.p. 176–177° C.

EXAMPLE 43

Using an analogous procedure to that described in Example 42, but using 4-tert-butylbenzaldehyde as starting material in place of benzaldehyde, there was prepared 1-[4-(4-t-butylcinnamoyl)phenyl]-4-(4-pyridyl)piperazine (46% yield), m.p. 213–214° C.

EXAMPLE 44

Using an analogous procedure to that described in Example 39, but using as starting material 1-(4-acetylphenyl)-4-(4-pyridyl)piperazine in place of 1-(4-formylphenyl)-4-(4pyridyl)piperazine and 4-tolualdehyde in place of 4-methylacetophenone, was prepared 1-[4-(4-methylphenylpropionyl)-phenyl]-4-(4-pyridyl)piperazine (27% yield), m.p. 130–132° C.

EXAMPLE 45

A solution of 4-(4-pyridyl)piperazine (5.0 g), bis(4-fluorophenyl)sulphone (15.58 g) and powdered potassium carbonate (6.35 g) was stirred at 95° C. in DMF (30 ml) overnight. The solution was poured into water (150 ml) to give a black solid from which the aqueous phase was decanted. The solid was heated in ethanol and a brown solid was collected by filtration. The filtrate was evaporated and the residue was purified by chromatography on alumina (ICN Alumina N 32–63) first using ethyl acetate as eluent followed by 10% methanol in dichloromethane. This gave 1-(4-fluorophenylphenylsulphone)-4-(4pyridyl)piperazine as a yellow solid (521 mg); microanalysis: Found C, 63.3; H, 5.1; N, 10.9%; $C_{21}H_{20}FN_3O_2S$ requires: C, 63.5; H, 5.07; N, 10.6%.

EXAMPLE 46

A mixture of 4-[3-(4-cyanophenoxy)-1-pyrrolidinyl] pyridine (269 mg) and powdered potassium hydroxide (568 mg) in t-butanol (10 ml), under an atmosphere of argon, was heated under reflux for 18 hours. The mixture was filtered hot. The filtercake was washed with water and ethanol to give 4-[3-(4-carbamoylphenoxy)-1-pyrrolidinyl]pyridine (166 mg) as a colourless solid, mp 298–300° C.

The 4-[3-(4-cyanophenoxy)-1-pyrrolidinyl]pyridine used as starting material was prepared as follows:

A solution of 4-chloropyridine hydrochloride (8.86 g), 3-pyrrolidinol (5.14 g) and triethylamine (14.8 ml) in water (65 ml) was stirred and heated under reflux for 65 hours. The solution was evaporated to a semi-solid. This residue was purified by flash column chromatography on silica (Merck 9385) using a 90:10:3 (v/v/v) mixture of ethyl acetate, methanol and aqueous ammonia solution as eluent, to give, after trituration with ethyl acetate, 4-(3-hydroxy-1-pyrrolidino)pyridine (5.95 g) as a cream solid, mp 207–209° C.

A solution of diethyl azodicarboxylate (1.73 ml) in dried tetrahydrofuran (10 ml) was added dropwise to a stirred mixture of triphenylphosphine (3.15 g), 4-cyanophenol (1.31 g) and 4-(3-hydroxy-1-pyrrolidinyl)pyridine (1.64 g) in dried tetrahydrofuran (45 ml), under an atmosphere of argon, at 5–7° C. The resulting solution was stirred at ambient temperature for 16 hours. The solid, which had separated, was filtered off and washed with diethyl ether to give 4-[3-(4-cyanophenoxy)-1-pyrrolidinyl]pyridine (823 mg) as an off-white solid, mp 182–185° C.

EXAMPLE 47

A 2M solution of sodium methoxide in methanol (0.89 ml) was added to a suspension of ethyl 4-[4-(4-pyridyl)-1-piperazinyl]benzoate (500 mg) in a 33% solution of monomethylamine in ethanol (15 ml). The mixture was stirred at 40° C. for 18 hours. The mixture was cooled and the solid was collected by filtration. The solid was washed with ethanol and ether to give 1-(4-methylcarbamoylphenyl)-4-(4-pyridyl) piperazine (374 mg) as a cream solid, mp 239–242° C.

The ethyl 4-[4-(4-pyridyl)-1-piperazinyl]benzoate used as starting material was prepared as follows:

A solution of 4-(4-pyridyl)piperazine (9.78 g), ethyl 4-fluorobenzoate (9.7 ml) and powdered potassium carbonate (9.9 g) in dried dimethylsulphoxide (60 ml) was heated at 95° C. for 18 hours. The mixture was poured into water (1200 ml) and stirred for 30 minutes. The precipitate was filtered off, washed with water and dried. The solid was purified by flash column chromatography on alumina (ICN alumina N32-63) using 1% methanol/dichloromethane as eluent, to give ethyl 4-[4-(4-pyridyl)-1-piperazinyl]benzoate (4.85 g) as a cream solid, mp 162–164° C.

EXAMPLE 48

Oxalyl chloride (0.25 ml) was added dropwise to a stirred suspension of 4-[1-(4-pyridyl)piperazin-4-yl]benzoic acid (530 mg) in dried dichloromethane (20 ml) containing dimethylformamide (1 drop). The mixture was stirred at ambient temperature for 1.5 hours and evaporated to dryness. The residue was suspended in dried dichloromethane (25 ml), t-Butylamine (2 ml) was added slowly to this stirred suspension at 5° C. The mixture was stirred at ambient temperature for 3 hours, then evaporated to dryness. The residue was suspended in aqueous sodium hydrogen carbonate solution (30 ml) and the mixture was extracted with ethyl acetate (3×60 ml). The ethyl acetate extracts were combined, washed successively with aq NaHCO$_3$ solution (30 ml) and saturated brine (30 ml), dried (Na$_2$SO$_4$) and evaporated to dryness. The residue was recrystallised from ethyl acetate (25 ml) to give give 1-(4-t-butylcarbamoylphenyl)-4-(4-pyridyl)piperazine (390 mg) as a colourless solid mp 214–217° C.

The 4-[1-(4-pyridyl)piperazin-4-yl]benzoic acid used as starting material was prepared as follows:

1M sodium hydroxide solution (103 ml) was added to a suspension of ethyl 4-[4-(4pyridyl)-1-piperazinyl]benzoate (10.3 g) in ethanol (200 ml) and the mixture was stirred at ambient temperature for 16 hours. The solution was evaporated to dryness. The residue was stirred in water (515 ml) for 15 minutes and any insoluble material was filtered off. The filtrate was treated with ice-cooled 1 M hydrochloric acid (103 ml). The precipitate was filtered off, slurry washed with water, sucked dry and dried over phosphorus pentoxide, at 50° C. for 2 days to give 4-[1-(4-pyridyl)piperazin-4-yl]-benzoic acid (5.24 g) as an off-white solid, mp>300° C.

EXAMPLE 49

Using an analogous procedure to that described in Example 48, but using n-butylamine as starting material in place of t-butylamine, was prepared 1-(4-n-butylcarbamoylphenyl)-4-(4-pyridyl)piperazine (67% yield) as a colourless solid, mp 172–174° C.

EXAMPLE 50

1(4-Methoxycarbonylphenylmethyl)-4-(4-pyridyl) piperazine (933 mg;3.0 mmol) was dissolved in methanol (8 ml) and treated at ambient temperature under an argon atmosphere with an excess of piperidine (~20 equivalents) and 2M sodium methoxide in methanol (3 ml). The resulting solid suspension was heated at 65° C. under reflux for 20 hours and then allowed to cool to room temperature. The reaction mixture was treated with a saturated aqueous solution of sodium hydrogen carbonate and extracted with CH$_2$Cl$_2$. The organic extracts were washed with water and brine, dried over MgSO$_4$, filtered and evaporated to yield an impure solid. The solid was chromatographed on silica gel (Varian bond elut-trademark) prepacked silica column, eluting with a mixture of methanol (1%), ammonium hydroxide (1%) and dichloromethane (98%) to give 1-(4-N-piperidinocarbonylphenylmethyl)-4-(4-pyridyl)piperazine (386% yield), NMR (CDCl$_3$): 1.51–1.73 (m,6H), 2.58 (t,4H), 3.28 (t, 4H), 3.49 (s,4H), 3.57 (s,2H), 6.64 (dd,2H), 7.30 (s,4H), 8.25 (dd,2H).

The 1-(4-methoxycarbonylphenylmethyl)-4-(4-pyridyl) piperazine used as starting material was prepared as follows:

4-Pyridyl piperazine (3.26 g) was dissolved in 20 ml of 10% water in iso-propanol and treated at ambient temperature, with agitation, with methyl 4-bromomethyl benzoate (4.58 g) and triethylamine (10 ml). The resulting yellow suspension was stirred vigourously for 30 minutes at room temperature and then heated at 100° C. under reflux for 20 hours. The suspension cleared to become a yellow solution when the reaction temperature had reached 60° C. After this period of heating the reaction mixture was allowed to cool to room temperature and the solvent removed by rotary evaporation under reduced pressure to yield an amber slurry. The slurry was treated with 2N aqueous sodium hydroxide and extracted with dichloromethane. The organic extracts were washed with saturated brine. dried over MgSO$_4$, filtered and evaporated down to an amber oil, which, after drying over 60 hours on a high vacuum pump yielded a pale yellow solid, 4.63 g (74%).

EXAMPLE 51

Using a similar method as described in Example 50 but using methylamine in place of piperidine there was obtained 1-(4-N-methylaminocarbonylphenylmethyl)-4-(4-pyridyl) piperazine (76% yield), m.p. 188–190° C.

EXAMPLE 52

1-(4-Carboxyphenylmethyl)-4-(4-pyridyl)piperazine (594 mg) was suspended in dichloromethane (25 ml) and treated at ambient temperature with thionyl chloride (5 ml) and heated at 40° C. over 18 hours. After this period the reaction mixture was allowed to cool to room temperature, evaporated to dryness, azeotroped with toluene and dried under high vacuum for 2 hours. The yellow solid obtained was suspended in dichloromethane (20 ml), stirred in an ice bath and treated at 0–5° C. with 5 equivalents of morpholine. The suspension was allowed to warm to ambient temperature and stirred for 18 hours. After this period the reaction mixture was treated with saturated aqueous sodium hydrogen carbonate and extracted with dichloromethane. The organic extracts were then washed with water and saturated brine, dried over MgSO$_4$, filtered and evaporated down to yield an impure solid. The solid was purified by chromatography on silica gel (Varian bond elut-trademark) prepacked silica column with a mixture of methanol (1–4%), ammonium hydroxide (1%) in dichloromethane to give 1-(4-N-morpholinocarbonylphenylmethyl)-4-(4-pyridyl) piperazine (33% yield) m.p. 121–125° C.

The 1-(4-carboxyphenylmethyl)-4-(4-pyridyl)piperazine used as starting material was prepared as follows:

1-(4-Methoxycarbonylphenylmethyl)-4-(4-pyridyl) piperazine (4.5 g) was dissolved in methanol (50 ml) and treated at ambient temperature with 2M aqueous sodium hydroxide (36 ml). The resulting solution was stirred at room temperature for 3 hours and concentrated by evaporation to an aqueous solution of the sodium salt of the acid. This solution was just acidified with glacial acetic acid (4.3 ml) to give a white precipitate which was collected by filtration, washed with water and dried to give 1-(4-carboxyphenylmethyl)-4-(4-pyridyl)piperazine in 90% yield.

EXAMPLE 53

Using a similar method to that described in Example 52 but using ethylamine in place of morpholine there was obtained 1-(4-ethylaminocarbonylphenylmethyl)-4-(4pyridyl)piperazine (51% yield), m.p. 213–215° C.

EXAMPLE 54

Using a similar method to that described in Example 50 there was obtained the following compounds.

| X | $R_1$ | mp (° C.) |
|---|---|---|
| $CH_2$ | (benzoyl) | 144–147 |
| $CH_2$ | (phenylsulfonyl) | 145–147 |

EXAMPLE 55

Ethyl magnesium chloride (3M) in anhydrous THF (10 ml) was treated at room temperature under argon with a solution of 1-(4-acetylphenyl)-4-(4-pyridyl)piperazine (281 mg) in anhydrous THF (15 ml). The resulting solid suspension was heated at 70° C. under reflux for 3 hours. The mixture was cooled in ice at 0–5° C. and treated with diethyl ether and a saturated solution of aqueous ammonium chloride. The reaction mixture was stirred for 10 minutes with ice cooling and at room temperature for 10 minutes. The aqueous phase was then extracted with dichloromethane and the ether phase was evaporated. The residue was dissolved in dichloromethane and combined with the other organic extracts. The combined extracts were then washed with saturated brine, dried over $MgSO_4$, filtered and evaporated to give an impure orange solid. The solid was purified by chromatography on a prepacked silica column ("Varian bond elut-trademark), eluting with a mixture of methanol (1–2%) and ammonium hydroxide (1%) in dichloromethane to obtain a pale yellow solid which was triturated with diethyl ether to give 1-(4-(1-hydroxy-1-methylethyl)phenyl)4-(4-pyridyl)piperazine (21% yield) as a pale yellow solid, m.p. 234–235° C.

EXAMPLE 56

4-(5-Cyano,2-pyridinoxy)piperidine (337 mg) and 4-chloropyridine hydrochloride (284 mg) were dissolved in water (10 mL) and treated with triethylamine (0.47 mL) in isopropanol (1 mL) and refluxed for 24 hours. The reaction was quenched by evaporation of the solvent. The residue was dissolved in dichloromethane and washed with aqueous sodium hydrogen carbonate solution, water, brine, dried ($MgSO_4$) and evaporated. The residue was triturated with diethyl ether to give 1-(4-pyridyl),4-(5-cyano,2-pyridinyloxy)piperidine (50 mg) as a pale cream crystalline solid; microanalysis, found: C, 66.4; H, 5.6; N, 19.0%; $C_{16}H_{16}N_3O0.5.H_2O$ requires: C, 66.4; H, 5.9; N, 19.4%; NMR: ($CDCl_3$) 1.90 (m,2H), 2.10 (m,2H), 3.32 (m,2H), 3.67 (m,2H), 5.37 (m,1H), 6.68 (d,2H), 6.80 (d,1H), 7.78 (dd,1H), 8.28 (d,2H), 8.47 (d,1H): MS: m/z 281 (MH)$^+$.

The 4-(5-cyano,2-pyridinoxy)piperidine starting material was prepared as follows:

To a solution of 1-(t-butyloxycarbonyl)-4-piperidinol (600 mg) in dry DMF (20 mL) was added sodium hydride (0.24 g, 50% dispersion in oil) and stirred under argon for 1 hour. 2-Chloro,5-cyanopyridine (0.44 g) was added and the mixture was heated at 70° C. overnight. The reaction was quenched by pouring into water and extracted with diethyl ether. The extract was washed with water, brine, dried ($MgSO_4$) and evaporated. The residue was then chromatographed on silica gel eluting with a mixture of dichloromethane (25%) in isohexane increasing to dichloromethane. The residue was recrystallised from isohexane to afford 1-(t-butyloxycarbonyl),4-(5-cyano,2-pyridyloxy) piperidine (400 mg) as a colourless crystalline solid; NMR: ($CDCl_3$) 1.46 (s,9H), 164–182 (m,2H), 1.92–2.09 (m,2H), 3.21–3.36 (m,2H), 3.70–3.84 (m,2H), 5.28 (m,1H), 6.78 (d,1H), 7.77 (dd,1H): MS: m/z 304 (MH)$^+$.

To 1-(t-butyloxycarbonyl),4-(5-cyano,2-pyridinyloxy) piperidine (1.6 g) in dichloromethane (20 mL) was added trifluoroacetic acid (1.2 mL) and the reaction stirred at room temperature for 1 hour. The reaction was quenched by evaporation of trifluoroacetic acid dissolving the residue in water, basifying with sodium hydrogen carbonate and extracting the dichloromethane. The organic layer was then washed with water, brine, dried ($MgSO_4$) and evaporated to yield 4-(5-cyano,2-pyridyloxy)piperidine as a white crystalline solid (337 mg), MS: m/z 279 (MH$^+$).

EXAMPLE 57

Using the procedure described in Example 1, the following compounds were prepared.

| Compound No | Ring A | X R | m.p. (° C.) |
|---|---|---|---|
| 1 | 1-piperazin-4-yl | — 4-$CH_2NH_2$ | 167–168 |
| 2 | 1-piperazin-4-yl | — 4-fluorophenyl-sulphonamidomethyl | 169–170 |
| 3 | 1-piperazin-4-yl | — 3-nitrophenyl-sulphonamidomethyl | 10.66 minutes* |
| 4 | 1-piperazin-4-yl | — 3.4-dimethoxy-phenylsulphonamido | 11.43 minutes* |

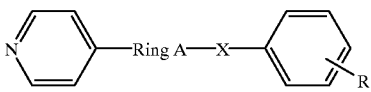

| Compound No | Ring A | X | R | m.p. (° C.) |
|---|---|---|---|---|
| 5 | 1-piperazin-4-yl | — | 2,4,5-trichloro-phenylsulphinamidomethyl | 13.03 minutes* |
| 6 | 1-piperazin-4-yl | — | 2-chloro-4-cyanosulphonamido-methyl | 10.64 minutes* |
| 7 | 1-piperazin-4-yl | — | 3,4-dimethyl-sulphonamidomethyl | 12.53 minutes* |
| 8 | 1-piperazin-4-yl | — | 4-t-butyl-sulphonamido methyl | 13.68 minutes* |
| 9 | 1-piperazin-4-yl | — | 2-nitro sulphonamino-methyl | 10.56 minutes* |
| 10[b] | 1-pyrolidin-3-yl | 0 | 4-cyano | 174–175 |

| Time | % Solvent C | % Solvent D |
|---|---|---|
| 0 | 95 | 5 |
| 3 | 95 | 5 |
| 17 | 5 | 95 |
| 18 | 95 | 5 |
| 20 | 95 | 5 |

EXAMPLE 58

A solution of 4-pyridyl piperazine (9.78 g), 4-fluorobenzonitrile(7.26 g) and powdered potassium carbonate(10 g) was stirred and heated in DMSO(100 ml) at 100° C. for 18 hours. The solution was poured into water (500 ml) to give a precipitate which was filtered and washed with water. The crude solid was dried in a vacuum oven for 18 hours. The residue was dissolved in dichloromethane and purified by flash chromatography on alumina (ICN Alumina N 32-63) using an increasing concentration of ethyl acetate in dichloromethane (up to 100% ethyl acetate) as eluant to give a solid which was recrystallised from ethyl acetate/isohexane to give 1-(4-cyanophenyl)-4-(4-pyridyl) piperazine (7.5 g) as a solid. m.p. 157–158° C.; microanalysis. found: C, 72.7; H, 6.1; N, 21.0%; $C_{16}H_{16}N_4$ requires: C, 72.7; H, 6.1; N, 21.2%. NMR (dmso-d6):3.45–3.55(8H,bs), 6.8–6.9(2H,d);7.0–7.1(2H,d); 7.55–7.65(2H,d);8.1–8.2(2H, d); MS m/Z 265 (M+H).

EXAMPLE 59

A solution of 1-(4-cyanophenyl)-4-(4-pyridyl)piperazine (1.8 g) in ethanol saturated with ammonia gas (150 ml) was hydrogenated at 150 atmospheres and 100° C. over Raney Nickel as catalyst for 18 hours. The solution was filtered through Celite and the filtrate evaporated to dryness. The residue was purified by flash chromatography on alumina (ICN Alumina N 32-63) using a mixture of 95:5 dichloromethane:methanol as eluant to give a solid which was recrystallised from tetrahydrofuran/isohexane to give 1-(4-(aminomethyl)phenyl)-4-(4-pyridyl)[piperazine (1.3 g) m.p. 168–170° C.; microanalysis, found: C,71.5;H,7.6;N, 20.5%;$C_{16}H_{20}N_4$ requires: C,71.6;H,7.5;N,20.9%; NMR (dmso-d6):3.2–3.4(4H,m);3.4–3.6(4H,m);3.65(2H,s) ;6.8–6.9(2H,d);6.9–7.0(2H,d);7.15–7.25(2H,d);8.15–8.25 (2H,d); MS: m/Z 269 (M+H).

EXAMPLE 60

To a solution of 6-chloronicotinic acid (188 mg.) in tetrahydrofuran (5 ml), was added 1,1-carbonyldiimidazole (178 mg) and the solution stirred for 1 hour. A solution of 1-[4-(2-aminoethyl)phenyl]-4-(4-pyridyl)piperazine (268 mg) in tetrahydrofuran (10 ml) was then added in one portion and the resulting solution stirred at ambient temperature overnight. The solution was evaporated to dryness and tetrahydofuran (2 ml) and aqueous sodium bicarbonate (10 ml, 1 molar) were added to the residue which was stirred vigorously for thirty minutes. The solution was filtered and the residue washed with water and air dried to give 1-(4-pyridyl)-4-[4-(6-chloronicotinamidomethyl)phenyl]) piperazine (230 mg) as a solid, m.p. 208–210° C.; microanalysis found: C,63.5; H,5.3; N,16.8; $C_{22}H_{22}ClN_5O$ $0.5H_2O$ requires: C,63.5; H,5.5; N,16.8; NMR (dmso-d6): 3.2–3.3(m,4H), 3.4–3.5(m,4H), 4.35–4.45(d,2H), 6.8–6.85 (d,2H), 6.9–7.0(d,2H), 7.15–7.25(d,2H), 7.57–7.63(d,2H), 8.1–8.2(d,2H), 8.25–8.35(dd,1H), 8.65–8.7(d,2H), 9.07–9.17(bt,1H): MS m/z 408 (M+H)

EXAMPLE 61

A solution of 2,4 dichloropyrimidine (1.5 g), sodium bicarbonate (1.0 g) and 1,4 piperazinyl 4 benzonitrile (1.8 g) in ethanol (50 ml) was stirred and heated under reflux for 18 hours. Water (200 ml) was added to give a precipitate which was filtered washed with water and recrystallised twice from a mixture of tetrahydrofuran and hexane to give 1-(4-cyanophenyl)-4-(2-chloropyrimidin-4-yl)piperazine (1.73 g) m.p. 216–218° C.

EXAMPLE 62

To a solution of benzoic acid (22 mg) in dimethylformamide (2 ml), was added 1,1-carbonyldiimidazole (188 mg) in dimethylformamide (2 ml) and the solution stirred at ambient temperature for 1 hour. A solution of 1-[4-(2-aminoethyl)phenyl]-4-(4-pyridyl)piperazine (268 mg) in dimethylformamide (4 ml) was then added in one portion and the resulting solution stirred at ambient temperature for twelve hours. The solution was evaporated to dryness and aqueous sodium bicarbonate (8 ml, 1M) added. The mixture was d stirred vigorously at ambient temperature for thirty minutes. The solid was collected by filtration, washed with water to give 1-(4-pyridyl)-4-(benzoyl-aminomethyl-phenyl)piperazine (389 mg), retention time 11.49 mins (same HPLC conditions as in Example 57).

EXAMPLE 63

In a similar manner to Example 62, 1-(4-pyridyl)-4-(4-(3-thienylcarbonylaminomethyl)phenyl was prepared (386 mg), retention time 14.59 minutes.

EXAMPLES 64–96

The following compounds are conveniently prepared according to the following general synthetic methods:

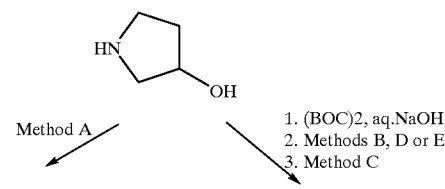

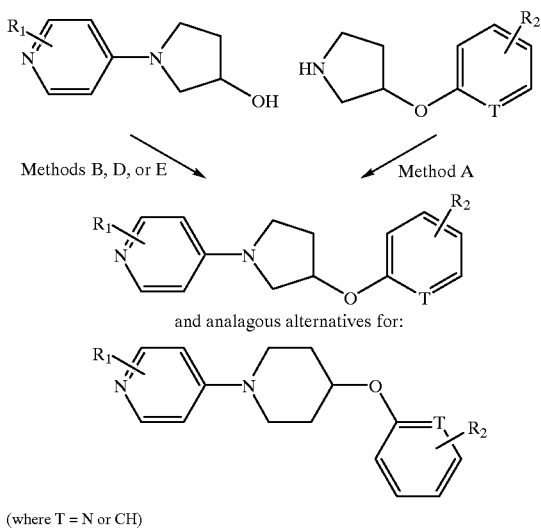

(where T = N or CH)

In a typical procedure for Method A the neutral amine (or salt thereof) is mixed with a pyridine substituted in the 4-position with a suitable leaving group such as Cl, Br, or methanesulphonyloxy (or salt thereof) in the presence of a suitable base such as a tertiary amine, a metal alkoxide or a metal carbonate salt. The reaction is typically carried out at from room temperature to 150° C., preferably at about 100° C., in a suitable solvent such as water, an alcohol or xylenes.

The starting amines are conveniently prepared by removal of a standard protecting group such as t-butyloxycarbonyl. The reaction is performed in the presence of a strong acid such as trifluoroacetic acid or a mineral acid, optionally in a solvent such as water or dichloromethane, typically according to Method C. The reaction is typically carried out at from −20° C. to 100° C., preferably at about room temperature.

In a typical procedure for Methods B and D the alcohol is mixed with a pyridine substituted in the 2-position with a suitable leaving group such as Cl, Br, or methanesulphonyloxy (or salt thereof), or a benzene substituted with a similarly appropriate leaving group, in the presence of a suitable base such as a metal hydride, a metal alkoxide or a metal amide and optionally a phase transfer catalyst such as a tetralkylammonium salt. The reaction is typically carried out at from −20° C. to 100° C., preferably at about room temperature, and may optionally be performed in the presence of a solvent such as tetrahydrofuran, toluene, dichloromethane or N,N-dimethylformamide.

In a typical procedure for Method E the alcohol is mixed with a phenol or 2-pyridone derivative in the presence of a suitable azodicarboxylate derivative such as diisopropylazodicarboxylate and a phosphine derivative such as triphenylphosphine or tri-n-butylphosphine, or any other such variant on the general method originally defined by O. Mitsunobu et al. (*Bull. Chem. Soc. Jpn.*, 1971, 44, 3427). The reaction is typically carried out at from −20° C. to 100° C., preferably at about room temperature, in a solvent such as tetrahydrofuran, toluene or dichloromethane under an inert atmosphere such as nitrogen or argon.

Alternatively the alcohol may be derivatised as a sulphonyl ester (such as methanesulphonyl) or halide. and the typical leaving group so generated may be displaced by a suitable salt of the phenol or 2-pyridone derivative (such as the lithium, sodium or potassium salt), optionally in the presence of a phase transfer catalyst such as a tetralkylammonium salt (as in Method G). The reaction is typically carried out at from −20° C. to 100° C., preferably at about room temperature, and may optionally be performed in the presence of a solvent such as tetrahydrofuran, toluene, dichloromethane or N,N-dimethylformamide.

In a typical procedure for Method F the piperazine is mixed with a heterocycle substituted with a suitable leaving group such as Cl, Br, or methanesulphonyloxy (or salt thereof), or a benzene derivative substituted with a similarly appropriate leaving group. The reaction is typically carried out at from 0° C. to 150° C., preferably at about 70° C., in a solvent such as water, a suitable alcohol, toluene or other substituted benzene derivatives, under an inert atmosphere such as nitrogen or argon.

The starting materials for the above methods are either known compounds or may be prepared by conventional procedures in accordance with literature precedents.

General Synthetic Methods

Method A

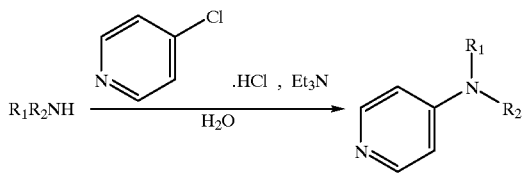

The amine (1.0 equivalent) and 4-chloropyridine hydrochloride (1.0 equivalent) were dissolved in $H_2O$ (0.88M in each reagent) and $Et_3N$ (1.8 equivalent) was added at ambient temperature. The mixture was heated at reflux until reaction was complete.

Method B

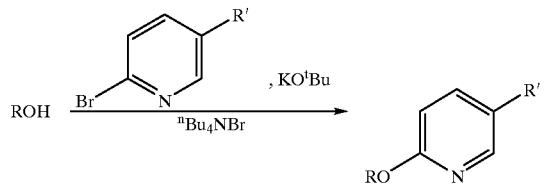

Under argon, potassium t-butoxide (2.0 equivalent) and alcohol (1.0 equivalent) were stirred together for 5 minutes. Tetra-n-butylammonium bromide (0.06 equivalent) was added followed by the 2-halopyridine (1.53 equivalent). If necessary, the mixture was heated at 80° C. until reaction was complete.

Method C

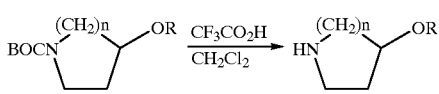

The carbamate (1.0 equivalent) in $CH_2Cl_2$ (0.88M) was cooled to 5° C. and trifluoroacetic acid (0.33×volume of $CH_2Cl_2$) was added dropwise. The mixture was warmed to ambient temperature and stirred until reaction was complete.

Method D

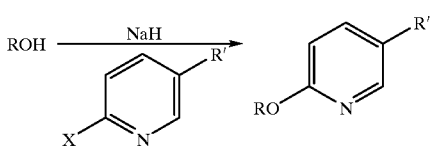

Sodium hydride (60% dispersion in paraffin oil, 146 mg, 1.2 equivalent) was added to an oven-dried round-bottomed flask and washed under an argon atmosphere with pentane. DMF (5 ml) was then added. followed by the alcohol (1.0 equivalent, 3.05 mmol) and tetra-n-butylammonium bromide (59 mg, 0.18 mmol). The mixture was added as a slurry to the 2-halo-pyridine (1.5 equivalent) in a second dry flask under argon, with stirring. After the reaction was complete the solvent was evaporated under vacuum.

Method E

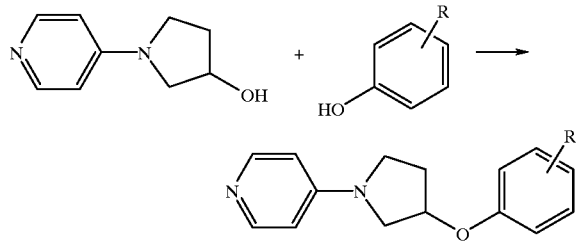

Under argon. the alcohol (1 equivalent), phenol (1 equivalent) and triphenylphosphine (1.44 equivalents) were mixed together in THF (0.3M solution) and cooled in an ice-bath. Diisopropylazodicarboxylate (1.53 equivalents) was added dropwise. The mixture was allowed to warm to room temperature and stirred overnight. All volatiles were removed under reduced pressure, and the residue was purified by column chromatography, eluting sequentially with $CH_2Cl_2$; 7% $MeOH/CH_2Cl_2$; 7%MeOH/1%$NH_4OH$/$CH_2Cl_2$; 10%MeOH/1%$NH_4OH$/$CH_2Cl_2$.

Method F

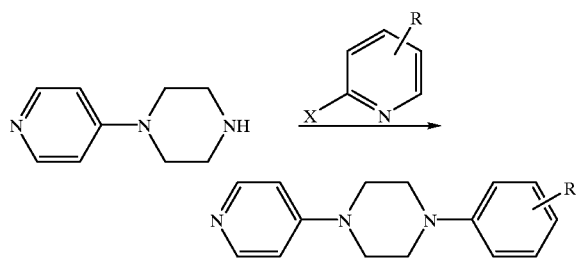

1-(4-pyridyl)-piperazine (1.0 equivalent) was heated with the appropriate 2-halopyridine (1.0 equivalent) and triethylamine (1.0 equivalent) in aqueous t-butanol (1:10; 0.41M) at reflux until reaction was complete.

Method G

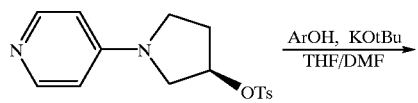

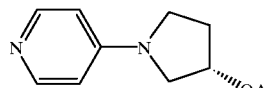

The phenol (0.94 mmol) was suspended in THF (1M) under argon. 1 ml potassium t-butoxide solution (1M in THF) was then added, followed by the relevant tosylate (0.94 mmol. in 2 ml DMF). The reaction was heated at reflux overnight, whereupon the solvents were removed under vacuum.

Intermediates 1-(4-Pyridyl)-3-hydroxypyrrolidine

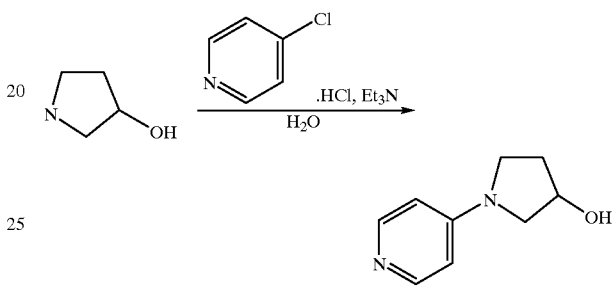

Scale: 5 g, 57.4 mmol

Method A. Work-up: the reaction mixture was cooled in an ice bath for 1 hour. The resultant white solid was filtered off and washed with ice water (30 ml) and dried overnight in vacuo in the presence of silica gel. The product was given as fine white powder.

Yield 5.78 g (61%).

$R_f$=0.1 (10%MeOH/1%$NH_4OH$/$CH_2Cl_2$)

$^1$H-NMR (200 MHz, DMSO-$d_6$): δ=2.0 (m, 2H), 3.22 (m, 1H), 3.7 (m, 3H), 4.4 (m, 1H), 5.0 (s, OH), 6.32 (m, 2H), 8.15 (m, 2H).

MS (ESP+): m/e 165 (M+H)$^+$.

(R)-1-(4-Pyridyl)-3-hydroxypyrrolidine

Made by the method used for racemic material. The NMR spectrum, mass spectrum and $R_f$ were as for the racemic material, and the R enantiomer gave an optical rotation ($α_D$) of −22.5 (c=10 mg/ml, MeOH).

(S)1-(4-Pyridyl)-3-hydroxypyrrolidine

Made by the method used for racemic material. The NMR spectrum, mass spectrum and $R_f$ were as for the racemic material, and the S enantiomer gave an optical rotation ($α_D$) of +22.7 (c=10 mg/ml, MeOH).

1-(4-Pyridyl)-4-hydroxypiperidine

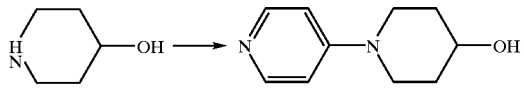

Scale: 26.9 g, 0.266 mol

Method A, using 4-hydroxypiperidine. Work-up: pH adjusted to 14 with aq. NaOH. Solid product filtered. Taken up with $H_2O$ & pH adjusted to 8.5. The solid product was filtered, dissolved in MeOH & preadsorbed onto silica. Column chromatography, eluting with 10%MeOH/$CH_2Cl_2$, increasing to 20%MeOH/5%$^i$PrNH$_2$/CH$_2$Cl$_2$ gave the product as a sticky solid.

Yield 22.25 g (47%).

R$_f$=0.25 (20%MeOH/1%NH$_4$OH/CH$_2$Cl$_2$)

$^1$H-NMR (DMSO-d$_6$): δ=1.4 (m, 2H), 1.6 (m, 2H), 3.05 (m, 2H), 3.5 (m, 3H), 6.6 (m, 2H), 8.1 (m, 2H).

MS (ESP+): m/e 179.5 (M+H)$^+$.

1-(t-butoxycarbonyl)-3-(5-trifluoromethyl-2-pyridyloxy)pyrrolidine

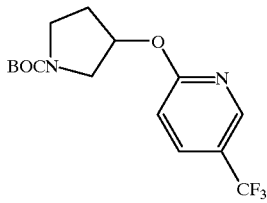

Scale: 4.99 g, 24.9 mmol

Method B, using 1-(t-butoxycarbonyl)-3-hydroxypyrrolidine. The crude product was partially purified by column chromatography on silica, eluting with 10%MeOH/CH$_2$Cl$_2$. Further purification by column chromatography on silica, eluting with 10%Et$_2$O/CH$_2$Cl$_2$, gave the product as an oily solid.

Yield 7.44 g (83%).

R$_f$=0.81 (10% Et$_2$O/CH$_2$Cl$_2$)

$^1$H-NMR (200 MHz, CDCl$_3$): δ=1.48 (s, 9H), 2.2 (m, 2H), 3.6 (m, 4H), 5.6 (m, 1H), 6.6 (d, 1H), 7.77 (dd, 1H), 8.42 (s, 1H).

MS (ESP+): m/e 333 (M+H)$^+$.

3-(5-trifluoromethyl-2-pyridyloxy)pyrrolidine

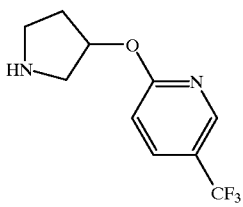

Scale: 7.34 g, 22 mmol

Method C. The solvents were evaporated and the residue partitioned between Et$_2$O and aq. HCl. The aqueous layer based basified with K$_2$CO$_3$ and extracted with CH$_2$Cl$_2$. The organic phase was dried over anhydrous Na$_2$SO$_4$ and evaporated to give an orange gum.

Yield=3.3 g (64%)

R$_f$=0.83 (10%MeOH/1%NH$_4$OH/CH$_2$Cl$_2$)

$^1$H-NMR (200 MHz, CDCl$_3$): δ=1.95 (m, 1H), 2.15 (m, 1H), 2.95 (m, 1H), 3.16 (m, 3H), 5.53 (m, 1H), 6.78 (d, 1H), 7.74 (dd, 1H), 8.42 (m, 1H).

MS (ESP+): m/e 233 (M+H)$^+$.

1-(t-butoxycarbonyl)-4-(5-trifluoromethyl-2-pyridyloxy)piperidine

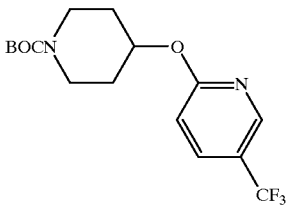

Scale: 4.99 g, 24.9 mmol

Method B. The crude product was partially purified by column chromatography on silica, eluting with EtOAc/hexane (0% to 25% in increments of 5%).

R$_f$=0.42 (20%EtOAc/hexane)

$^1$H-NMR (200 MHz, CDCl$_3$); δ=1.48 (s, 9H), 1.75 (m, 2H), 2.0 (m, 2H), 3.3 (m, 2H), 3.78 (m, 2H), 5.3 (m, 1H), 6.78 (d, 1H), 7.77 (dd, 1H), 8.4 (s, 1H).

MS (ESP+): m/e 347 (M+H)$^+$.

4-(5-trifluoromethyl-2-pyridyloxy)piperidine

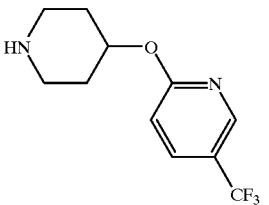

Scale: 9.2 g (impure), ca. 25 mmol

Method C. The solvents were evaporated and the residue partitioned between CH$_2$Cl$_2$ and aq. K$_2$CO$_3$. The organic phase was dried over anhydrous Na$_2$SO$_4$ and evaporated to give an orange gum. After trituration with Et$_2$O the product was isolated as an off-white solid.

Yield=3.58 g (55%)

R$_f$=0.19 (10%MeOH/1%NH$_4$OH/CH$_2$Cl$_2$)

$^1$H-NMR (250 MHz, CDCl$_3$): δ=1.7 (m, 2H), 2.1 (m, 2H), 2.85 (m, 2H), 3.15 (m, 2H), 5.25 (m, 1H), 6.75 (d, 1H), 7.75 (dd, 1H), 8.4 (d, 1H).

MS (ESP+): m/e 247 (M+H)$^+$.

1-(t-butoxycarbonyl)4-(5-bromo-2-pyridyloxy)piperidine

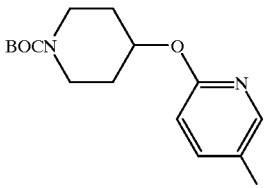

Scale: 0.79 g, 3.93 mmol

Method: under argon, 1-(t-butyloxycarbonyl)-4-hydroxypiperidine (0.79 g, 3.93 mmol), 5-bromo-2-pyridone (0.49 g, 3.02 mmol) and triphenylphosphine (1.14 g, 4.35 mmol) were dissolved in THF (20 ml). To the mixture was added diisopropylazodicarboxylate (0.91 ml, 4.62 mmol) dropwise at ambient temperature followed by stirring for 18 hours. The mixture was concentrated in vacuo and applied to the top of a silica column. Elution with solvent of increasing concentration of EtOAc in $CH_2Cl_2$ and evaporation in vacuo of the relevant fractions gave the product.

Yield=640 mg (61%)
$R_f$=0.63 (EtOAc)
$^1$H-NMR (200 MHz, CDCl$_3$): δ=1.46 (s, 9H), 1.7 (m, 2H), 1.92 (m, 2H), 3.25 (m, 2H), 3.75 (m, 2H), 5.15 (m, 1H), 6.61 (d, 1H), 7.61 (dd, 1H), 8.13 (d, 1H).
MS (ESP+): m/e 357/9 (M+H)$^+$.

4-(5-bromo-2-pyridyloxy)piperidine

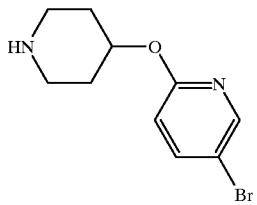

Scale: 4.99 g, 24.9 mmol
Method C. The solvents were evaporated and the residue partitioned between Et$_2$O and aq. HCl. The aqueous layer based basified with K$_2$CO$_3$ and extracted with CH$_2$Cl$_2$. The organic phase was dried over anhydrous Na$_2$SO$_4$ and evaporated to give an orange gum.

Yield=380 mg (90%)
$R_f$=0.43 (20%MeOH/1%NH$_4$OH/CH$_2$Cl$_2$)
$^1$H-NMR (250 MHz, CDCl$_3$): δ=1.7 (m, 2H), 2.05 (m, 2H), 2.77 (m, 2H), 3.14 (m, 2H), 5.08 (m, 1H), 6.61 (d, 1H), 7.66 (dd, 1H), 8.15 (d, 1H).
MS (ESP+): m/e 257/9 (M+H)$^+$.

(R)-1-(4-pyridyl)-3-(p-toluenesolphonyloxy) pyrrolidine

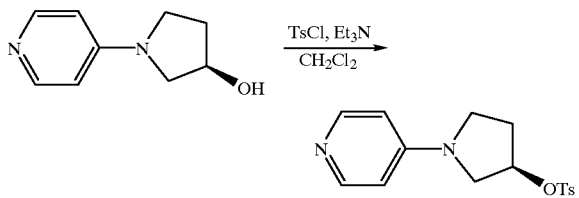

Scale: 1.0 g, 6.1 mmol
Tosyl chloride (1.28 g, 1.1 equivalents was added to a suspension of the alcohol and triethylamine (0.92 g, 1.1 equivalents) in dichloromethane (10 ml). A solution gradually formed. After stirring overnight, the solution was washed with saturated aqueous sodium bicarbonate solution, dried over sodium sulphate, filtered and evaporated. The residue was purified by column chromatography, eluting sequentially with CH$_2$Cl$_2$; 5%MeOH/CH$_2$Cl$_2$;10%MeOH/1%NH$_4$OH/CH$_2$Cl$_2$ giving a light brown solid.

Yield=1.14 g (58%)
$R_f$=0.32 (10%MeOH/1%NH$_4$OH/CH$_2$Cl$_2$)
$^1$H-NMR (300 MHz, CDCl$_3$): d=2.20 (m, 1H), 2.33 (m, 1H), 2.45 (s, 3H), 3.45 (m, 4H), 5.21 (m, 1H), 6.32 (d, 2H), 7.38 (d, 2H), 7.79 (d, 2H), 8.20 (d, 2H).
MS (ESP+): m/e 319 (M+H)$^+$.

The (S) enantiomer was made by an identical protocol starting from the (S) alcohol.

EXAMPLE 64

1-(4-pyridyl)-4-(5-methyl-2-pyridyloxy)piperidine

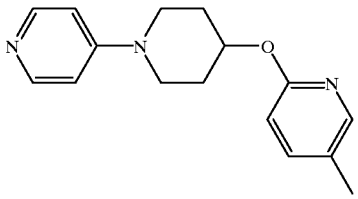

Scale: 500 mg, 2.8 mmol
Method B, using 1-(4-pyridyl)-4-hydroxypiperidine and 2-bromo-5-methylpyridine. The crude product was purified by column chromatography on silica, eluting with CH$_2$Cl$_2$, then Et$_2$O, then 10%MeOH/1%NH$_4$OH/CH$_2$Cl$_2$. The product was isolated as an orange solid.

Yield=349 mg (46%)
$R_f$=0.58 (10%MeOH/1%NH$_4$OH/CH$_2$Cl$_2$)
$^1$H-NMR (200 MHz, CDCl$_3$): δ=1.83 (m, 2H), 2.06 (m, 2H), 2.22 (s, 3H), 3.3 (m, 2H), 3.65 (m, 2H), 5.25 (m, 1H), 6.65 (m, 3H), 7.38 (dd, 1H), 7.92 (m, 1H), 8.25 (dd, 2H).
MS (CI): m/e 270 (M+H)$^+$.
Found: C,70.9; H,7.1; N,15.3; C$_{16}$H$_{19}$N$_3$O requires: C,71.3; H,7.11; N,15.6%.

The 1-(4-pyridyl)-4-hydroxypiperidine was prepared as follows:

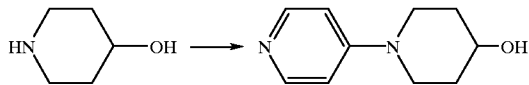

Scale: 26.9 g, 0.266 mol
Method A, using 4-hydroxypiperidine. Work-up: the pH was adjusted to 14 with aq. NaOH. The solid product was filtered, taken up with H$_2$O & pH adjusted to 8.5. The solid product was filtered, dissolved in MeOH & preadsorbed onto silica. Column chromatography, eluting with 10%MeOH/CH$_2$Cl$_2$ and increasing to 20%MeOH/5%$^i$PrNH$_2$/CH$_2$Cl$_2$ gave the product as a sticky solid.

Yield 22.25 g (47%).
$R_f$=0.25 (20%MeOH/1%NH$_4$OH/CH$_2$Cl$_2$)
$^1$H-NMR (DMSO-d$_6$): δ=1.4 (m, 2H), 1.6 (m, 2H), 3.05 (m, 2H), 3.5 (m, 3H), 6.6 (m, 2H), 8.1 (m, 2H).
MS (ESP+): m/e 179.5 (M+H)$^+$.

EXAMPLE 65

1-(4-pyridyl)-4-(5-cyano-2-pyridyloxy)piperidine

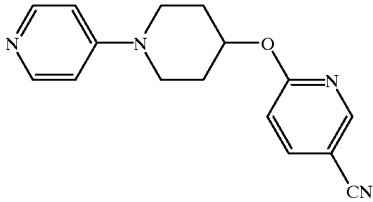

Scale: 500 mg, 2.8 mmol
Method B, using 1-(4-pyridyl)-4-hydroxypiperidine and 2-chloro-5-cyanopyridine. The crude product was dissolved in CH$_2$Cl$_2$ adsorbed onto silica and purified by column chromatography, eluting with 10%MeOH/1%NH₄OH/ CH₂Cl₂. The residue was further purified by column chromatography, eluting with 5%MeOH/1%NH₄OH/ CH₂Cl₂. The residue was suspended in ethyl acetate and a solution of dry HCl in ether added. The hydrochloride salt was filtered off and suspended in water. The pH was adjusted to 14 with aq NaOH and the product extracted into ethyl acetate/methanol (ca. 10:1). The organic phase was washed with brine. After evaporation, the product was triturated with ether, giving an orange solid.

Yield=48 mg (6%)

$R_f$=0.58 (10%MeOH/1%NH₄OH/CH₂Cl₂)

¹H-NMR (200 MHz, CDCl₃): δ=1.9 (m, 2H), 2.12 (m, 2H), 3.3 (m, 2H), 3.7 (m, 2H), 5.38 (m, 1H), 6.7 (m, 2H), 6.8 (d, 1H), 7.8 (dd, 1H), 8.3 (m, 2H), 8.48 (m, 1H).

MS (ESP+): m/e 281 (M+H)⁺.

EXAMPLE 66

1-(4-pyridyl)-4-(5-chloro-2-pyridyloxy)piperidine

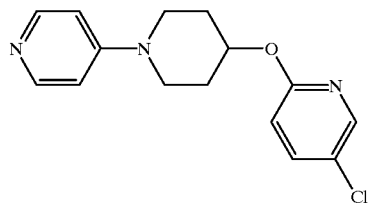

Scale: 500 mg, 2.8 mmol

Method B, using 1-(4-pyridyl)-4-hydroxypiperidine and 2,5-dichloropyridine. The reaction mixture was partitioned between aq. HCl and CH₂Cl₂. The aqueous phase was adjusted to pH 14 with aq. NaOH and extracted with CH₂Cl₂. The organic phase was washed with brine, dried over anhydrous Na₂SO₄ and evaporated. The residue was purified by column chromatography on silica eluting with CH₂Cl₂, then Et₂O, then 5%MeOH/1%NH₄OH/CH₂Cl₂ to give the product as a white solid.

Yield=303 mg (38%)

$R_f$=0.5 (10%MeOH/1%NH₄OH/CH₂Cl₂)

¹H-NMR (200 MHz, CDCl₃): δ=1.9 (m, 2H), 2.1 (m, 2H), 3.3 (m, 2H), 3.68 (m, 2H), 5.25 (m, 1H), 6.7 (m, 3H), 7.53 (dd, 1H), 8.07 (m, 1H), 8.28 (m, 2H).

MS (CI): m/e 290 (M+H)⁺.

EXAMPLE 67

1-(2,6-dimethyl-4-pyridyl)-4-(5-trifluoromethyl-2-pyridyloxy)piperidine

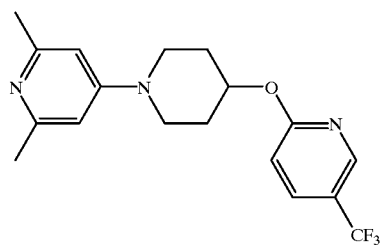

Scale: 300 mg, 1.22 mmol

Method A, using 2,6-dimethyl-4-chloropyridine (see T. Kato, H. Hayashi & T. Anzai; *Chem. Pharm. Bull.;* 15, 1967, 1343–1348) and 4-(5-trifluoromethyl-2-pyridyloxy) piperidine in a water/n-propanol (1:10) solvent mixture. The solvents were evaporated and the residue purified by column chromatography on silica, eluting with CH₂Cl₂, then 5%MeOH/1%NH₄OH/CH₂Cl₂, then 10%MeOH/ 1%NH₄OH/CH₂Cl₂, giving the product as a yellow glass.

Yield=171 mg (40%)

$R_f$=0.36 (10%MeOH/1%NH₄OH/CH₂Cl₂)

¹H-NMR (200 MHz, CDCl₃): δ=2.0 (m, 2H), 2.1 (m, 2H), 2.6 (s, 6H), 3.6 (m, 2H), 3.8 (m, 2H), 5.48 (m, 1H), 6.46 (s, 2H), 6.84 (d, 1H), 7.8 (dd, 1H), 8.07 (m, 1H), 8.42 (m, 1H).

MS(ESP+): m/e 352 (M+H)⁺.

The precursor 4-(5-trifluoromethyl-2-pyridyloxy) piperidine was made in three steps from 4-hydroxypiperidine as follows:

1) 1-(t-butoxycarbonyl)-4-hydroxypiperidine

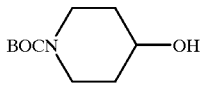

Scale: 44.14 g, 0.44 mol

4-Hydroxypiperidine (44.14 g, 0.44 mol) was suspended in CH₂Cl₂ (150 ml) and coiled in an ice-bath. A solution of di-t-butyl dicarbonate (100 g, 0.46 mol) in CH₂Cl₂ (110 ml) was added slowly. After stirring overnight the product was partitioned between water and CH₂Cl₂. The organic layer was washed with brine and dried over anhydrous magnesium sulphate. Filtration and evaporation gave the product as a white solid.

Yield 95 g (quantitative, crude).

$R_f$=0.18 (20% EtOAc/CH₂Cl₂)

¹H-NMR (200 MHz, CDCl₃): δ=1.45 (s, 9H), 1.43 (m, 2H), 1.85 (m, 2H), 3.04 (m, 2H), 4.85 (m, 1H).

MS (CI+): m/e 201 (M+H)⁺.

2) 1-(t-butoxycarbonyl)-4-(5-trifluoromethyl-2-pyridyloxy)piperidine

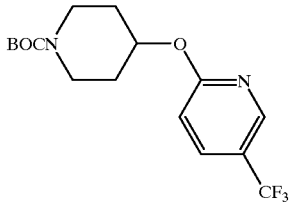

Scale: 4.99 g, 24.9 mmol

Method B, using 1-(t-butyloxycarbonyl)-4-hydroxypiperidine and 2-bromo-5-trifluoromethylpyridine. The crude product was partially purified by column chromatography on silica. eluting with EtOAc/hexane (0% to 25% in increments of 5%).

$R_f$=0.42 (20%EtOAc/hexane)

¹H-NMR (200 MHz, CDCl₃): δ=1.48 (s, 9H), 1.75 (m, 2H), 2.0 (m, 2H), 3.3 (m, 2H), 3.78 (m, 2H), 5.3 (m, 1H), 6.78 (d, 1H), 7.77 (dd, 1H), 8.4 (s, 1H).

MS (ESP+): m/e 347 (M+H)⁺.

3) 4-(5-trifluoromethyl-2-pyridyloxy)piperidine

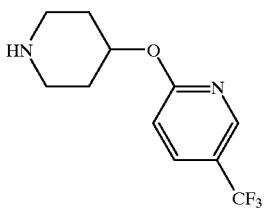

Scale: 9.2 g (impure), ca. 25 mmol

Method C. The solvents were evaporated and the residue partitioned between $CH_2Cl_2$ and aq. $K_2CO_3$. The organic phase was dried over anhydrous $Na_2SO_4$ and evaporated to give an orange gum. After trituration with $Et_2O$ the product was isolated as an off-white solid.

Yield=3.58 g (55%)

$R_f$=0.19 (10%MeOH/1%$NH_4OH$/$CH_2Cl_2$)

$^1$H-NMR (250 MHz, $CDCl_3$): δ=1.7 (m, 2H), 2.1 (m, 2H), 2.85 (m, 2H), 3.15 (m, 2H), 5.25 (m, 1H), 6.75 (d, 1H), 7.75 (dd, 1H), 8.4 (d, 1H).

MS (ESP+): m/e 247 (M+H)+.

EXAMPLE 68

1-(2-methyl-4-pyridyl)-3-(5-trifluoromethyl-2-pyridyloxy)pyrrolidine

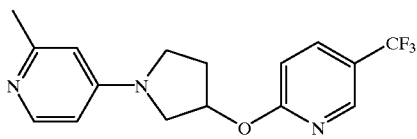

Scale: 500 mg, 2.16 mmol

Method A, using 2-methyl-4-chloropyridine (see T. Kato, H. Hayashi & T. Anzai; *Chem. Pharm. Bull.*: 15. 1967, 1343–1348) and 3-(5-trifluoromethyl-2-pyridyloxy) pyrrolidine. The solvents were evaporated and the residue was purified by column chromatography on silica. eluting with $Et_2O$, then EtOAc, then 5%MeOH/1%$NH_4OH$/$CH_2Cl_2$, then 10%MeOH/1%$NH_4OH$/$CH_2Cl_2$, giving the product as a white foam.

Yield=175 mg (25%)

$R_f$=0.35 (10%MeOH/1%$NH_4OH$/$CH_2Cl_2$)

$^1$H-NMR (200 MHz, $CDCl_3$): δ=2.45 (m, 2H), 2.65 (s, 3H), 3.68 (m, 3H), 3.75 (dd, 1H), 5.83 (m, 1H), 6.35 (m, 1H), 6.47 (dd, 1H), 6.84 (d, 1H), 7.82 (dd, 1H), 8.07 (d, 1H), 8.45 (m, 1H).

MS (ESP+): m/e 324 (M+H)+.

The precursor 3-(5-trifluoromethyl-2-pyridyloxy) pyrrolidine was made in three steps from 3-hydroxypyrrolidine as follows:

1) 1-(t-butoxycarbonyl)-3-hydroxypyrrolidine

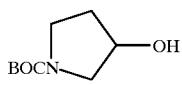

Scale: 5.0 g, 57.0 mmol

A solution of 3-hydroxypyrrolidine (5.0 g, 57.0 mmol) in $CH_2Cl_2$ (125 ml) was added to an ice-cold solution of di-t-butyl dicarbonate (13.15 g, 60 mmol) in $CH_2Cl_2$ (125 ml). After stirring overnight the solvents were evaporated and the residue purified by column chromatograph, on silica, eluting with $CH_2Cl_2$, then $Et_2O$, then EtOAc, givina the product as a white solid.

Yield 10.4 g (98%).

$R_f$=0.23 ($Et_2O$)

$^1$H-NMR (250 MHz, $CDCl_3$): δ=1.42 (s, 9H), 2.0 (m, 3H), 3.4 (m, 3H), 4.4 (m, 1H).

MS (CI+): m/e 188 (M+H)+.

2) 1-t-butoxycarbonyl)-3-(5-trifluoromethyl-2-pyridyloxy)pyrrolidine

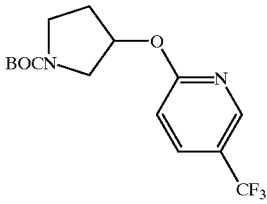

Scale: 4.99 g, 24.9 mmol

Method B, using 1-(t-butoxycarbonyl)-3-hydroxypyrrolidine and 2-bromo-5-trifluoromethylpyridine. The crude product was partially purified by column chromatography on silica, eluting with 10%MeOH/$CH_2Cl_2$. Further purification by column chromatography on silica, eluting with 10%$Et_2O$/$CH_2Cl_2$, gave the product as an oily solid.

Yield 7.44 g (83%).

$R_f$=0.81 (10% $Et_2O$/$CH_2C_2$)

$^1$H-NMR (200 MHz, $CDCl_3$): δ=1.48 (s, 9H), 2.2 (m, 2H), 3.6 (m, 4H), 5.6 (m, 1H), 6.6 (d, 1H), 7.77 (dd, 1H), 8.42 (s, 1H).

MS (ESP+): m/e 333 (M+H)+.

3) 3-(5-trifluoromethyl-2-pyridyloxy)pyrrolidine

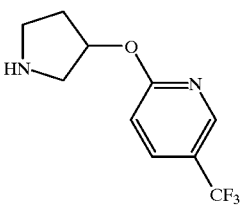

Scale: 7.34 g, 22 mmol

Method C. The solvents were evaporated and the residue partitioned between $Et_2O$ and aq. HCl. The aqueous layer based basified with $K_2CO_3$ and extracted with $CH_2Cl_2$. The organic phase was dried over anhydrous $Na_2SO_4$ and evaporated to give an orange gum.

Yield=3.3 g (64%)

$R_f$=0.83 (10%MeOH/1%$NH_4OH$/$CH_2Cl_2$)

$^1$H-NMR (200 MHz, $CDCl_3$): δ=1.95 (m, 1H), 2.15 (m, 1H), 2.95 (m, 1H), 3.16 (m, 3H), 5.53 (m, 1H), 6.78 (d, 1H), 7.74 (dd, 1H), 8.42 (m, 1H).

MS (ESP+): m/e 233 (M+H)+.

EXAMPLE 69

1-(2-methyl-4-pyridyl)-4-(5-trifluoromethyl-2-pyridyloxy)piperidine

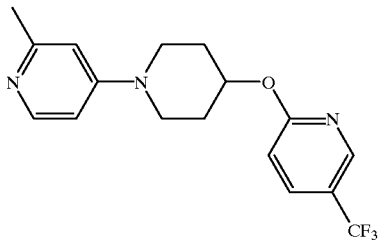

Scale: 300 mg, 1.22 mmol

Method A, using 2-methyl-4-chloropyridine and 4-(5-trifluoromethyl-2-pyridyloxy)piperidine. The solvents were evaporated and the residue was purified by column chromatography on silica, eluting with Et$_2$O, then EtOAc, then 5%MeOH/1%NH$_4$OH/CH$_2$Cl$_2$, then 10%MeOH/1%NH$_4$OH/CH$_2$Cl$_2$, giving the product as a yellow oil.

Yield=76 mg (18%)

R$_f$=0.54 (10%MeOH/1%NH$_4$OH/CH$_2$Cl$_2$)

$^1$H-NMR (200 MHz, CDCl$_3$): δ=2.0 (m, 2H), 2.15 (m, 2H), 2.6 (s, 3H), 3.6 (m, 2H), 3.8 (m, 2H), 5.48 (m, 1H), 6.6 (m, 1H), 6.72 (dd, 1H), 6.82 (d, 1H), 7.8 (dd, 1H), 8.25 (d, 1H), 8.43 (m, 1H).

MS (ESP+): m/e 338 (M+H)$^+$.

EXAMPLE 70

1-(4-pyridyl)-4-(5-bromo-2-pyridyloxy)piperidine

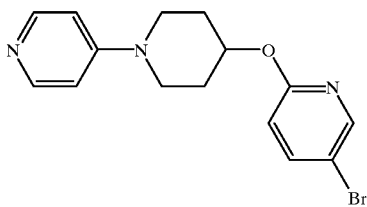

Scale: 360 mg, 1.4 mmol

Method A, using 4-(5-bromo-2-pyridyloxy)piperidine. The solvents were evaporated and the residue partitioned between CH$_2$Cl$_2$ and aq. K$_2$CO$_3$. The organic phase was dried over anhydrous Na$_2$SO$_4$ and evaporated. The residue was purified by column chromatography on silica, eluting from 1%MeOH/1%NH$_4$OH/CH$_2$Cl$_2$ to 10%MeOH/1%NH$_4$OH/CH$_2$Cl$_2$ (in 1% increments), giving the product as a white solid.

Yield=285 mg (61%)

R$_f$=0.61 (20%MeOH/1%NH$_4$OH/CH$_2$Cl$_2$)

$^1$H-NMR (200 MHz, CDCl$_3$): δ=1.85 (m, 2H), 2.08 (m, 2H), 3.32 (m, 2H), 3.65 (m, 2H), 5.25 (m, 1H), 6.65 (m, 3H), 7.65 (dd, 1H), 8.17 (d, 1H), 8.25 (m, 2H).

MS (Cl+): m/e 334 (M+H)$^+$.

Found: C,53.0; H,4.7; N,12.2; C$_{15}$H$_{16}$BrN$_3$O.(0.25H$_2$O) requires: C,53.1; H,5.06; N,12.4%.

The precursor 4-(5-bromo-2-pyridyloxy)piperidine was prepared in two steps from 1-(t-butoxycarbonyl)-4-hydroxypiperidine as follows:

1) 1-(t-butoxycarbonyl)-4-(5-bromo-2-pyridyloxy)piperidine

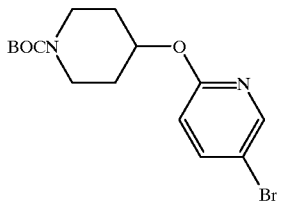

Scale: 0.79 g, 3.93 mmol

Method: under argon, 1-(t-butyloxycarbonyl)-4-hydroxypiperidine (0.79 g, 3.93 mmol), 5-bromo-2-pyridone (0.49 g, 3.02 mmol) and triphenylphosphine (1.14 g, 4.35 mmol) were dissolved in THF (20 ml). To the mixture was added diisopropylazodicarboxylate (0.91 ml, 4.62 mmol) dropwise at ambient temperature followed by stirring for 18 hours. The mixture was concentrated in vacuo and applied to the top of a silica column. Elution with solvent of increasing concentration of EtOAc in CH$_2$Cl$_2$ and evaporation in vacuo of the relevant fractions gave the product.

Yield=640 mg (61%)

R$_f$=0.63 (EtOAc)

$^1$H-NMR (200 MHz, CDCl$_3$): δ=1.46 (s, 9H), 1.7 (m, 2H), 1.92 (m, 2H), 3.25 (m, 2H), 3.75 (m, 2H), 5.15 (m, 1H), 6.61 (d, 1H), 7.61 (dd, 1H), 8.13 (d, 1H).

MS (ESP+): m/e 357/9 (M+H)$^+$.

2) 4-(5-bromo-2-pyridyloxy)piperidine

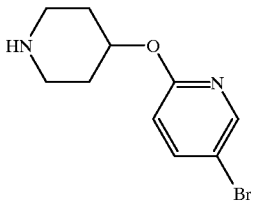

Scale: 4.99 g, 24.9 mmol

Method C. The solvents were evaporated and the residue partitioned between Et$_2$O and aq. HCl. The aqueous layer based basified with K$_2$CO$_3$ and extracted with CH$_2$Cl$_2$. The organic phase was dried over anhydrous Na$_2$SO$_4$ and evaporated to give an orange gum.

Yield=380 mg (90%)

R$_f$=0.43 (20%MeOH/1%NH$_4$OH/CH$_2$Cl$_2$)

$^1$H-NMR (250 MHz, CDCl$_3$): δ=1.7 (m, 2H), 2.05 (m, 2H), 2.77 (m, 2H), 3.14 (m, 2H), 5.08 (m, 1H), 6.61 (d, 1H), 7.66 (dd, 1H), 8.15 (d, 1H).

MS (ESP+): m/e 257/9 (M+H)$^+$.

EXAMPLE 71

1-(4-pyridyl)-4-(5-trifluoromethyl-2-pyridyloxy)piperidine

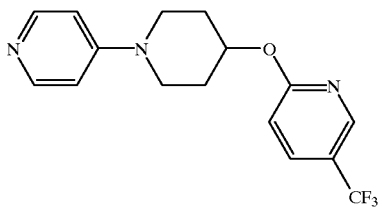

Scale: 714 mg, 4 mmol

Method B, using 1-(4-pyridyl)-4-hydroxypiperidine and 2-bromo-5-trifluoromethylpyridine. The solvents were evaporated and the residue was purified by column chromatography on silica, eluting from 1%MeOH/1%iPrNH$_2$/CH$_2$Cl$_2$ to 5%MeOH/5%iPrNH$_2$/CH$_2$Cl$_2$ (in 1% increments). A second columnm, eluting with 1%MeOH/1%NH$_4$OH/CH$_2$Cl$_2$ to 10%MeOH/1%NH$_4$OH/CH$_2$Cl$_2$ (in 1% increments), gave a dark oil, which was extracted with Et$_2$O/hexane. Evaporation and washing with hexane gave the product as a light brown solid.

Yield=674 mg (52%)

$R_f$=0.52 (10%MeOH/1%NH$_4$OH/CH$_2$Cl$_2$)

$^1$H-NMR (200 MHz, CDCl$_3$): δ=1.9 (m, 2H), 2.1 (m, 2H), 3.32 (m, 2H), 3.68 (m, 2H), 5.38 (m, 1H), 6.70 (d, 2H), 6.62 (d, 2H), 7.77 (dd, 1H), 8.27 (d, 2H), 8.44 (s, 1H).

MS (ESP+): m/e 324 (M+H)$^+$.

Found: C,57.7; H,5.1; N,12.4; C$_{16}$H$_{16}$F$_3$N$_3$O.(0.5H$_2$O) requires: C,57.8; H,5.15; N,12.64%.

EXAMPLE 72

1-(4-pyridyl)-4-(5-nitro-2-pyridyloxy)piperidine

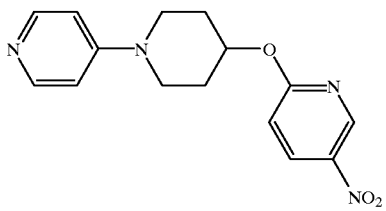

Scale: 433 mg, 2.43 mmol

Method B, using 1-(4-pyridyl)-4-hydroxypiperidine and 2-bromo-5-nitropyridine. The solvents were evaporated and the residue was columned on silica, eluting from 1%MeOH/1%NH$_4$OH/CH$_2$Cl$_2$ to 10%MeOH/1%NH$_4$OH/CH$_2$Cl$_2$ (in 1% increments), giving a brown solid. After recrystallisation from methyl t-butyl ether, the product was isolated as an orange solid.

Yield=70 mg (10%)

$R_f$=0.39 (10%MeOH/1%NH$_4$OH/CH$_2$Cl$_2$)

$^1$H-NMR (200 MHz, CDCl$_3$): δ=1.9 (m, 2H), 2.15 (m, 2H), 3.33 (m, 2H), 3.68 (m, 2H), 5.45 (m, 1H), 6.70 (dd, 2H), 6.82 (d, 1H), 8.28 (dd, 2H), 8.35 (dd, 1H), 9.06 (d, 1H).

MS (ESP+): m/e 301 (M+H)$^-$.

EXAMPLE 73

1-(4-pyridyl)-3-(5-bromo-2-pyridyloxy)pyrrolidine

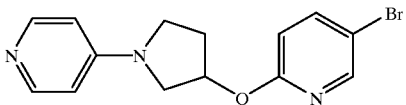

Scale: 492 mg, 3 mmol

Method B, using 1-(4-pyridyl)-3-hydroxypyrrolidine and 2,5-dibromopyridine. The crude residue was recrystallised from methyl t-butyl ether.

Yield=620 mg (65%)

$R_f$=0.41 (10%MeOH/1%NH$_4$OH/CH$_2$Cl$_2$)

$^1$H-NMR (300 MHz, CDCl$_3$): δ=2.35 (m, 2H), 3.5 (m, 3H), 3.72 (dd, 1H), 5.65 (m, 1H), 6.38 (m, 2H), 6.62 (d, 1H), 7.64 (dd, 1H), 8.2 (m, 3H).

MS (ESP+): m/e 320/2 (M+H)$^+$.

Found: C,52.9; H,4.6; N,12.8; C$_{14}$H$_{14}$BrN$_3$O requires: C,52.5; H,4.41; N,13.1%.

The precursor 1-(4-pyridyl)-3-hydroxypyrrolidine was prepared as follows:

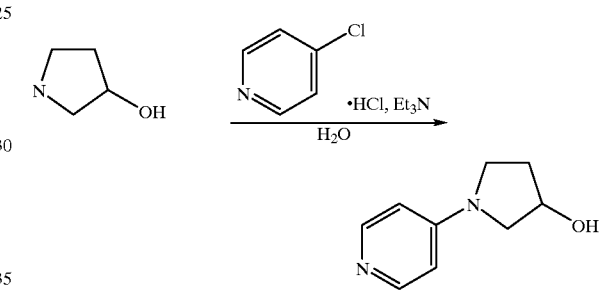

Scale: 5 g, 57.4 mmol

Method A. Work-up: the reaction mixture was cooled in an ice bath for 1 hour. The resultant white solid was filtered off and washed with ice water (30 ml) and dried overnight in vacuo in the presence of silica gel. The product was given as fine white powder.

Yield 5.78 g (61%).

$R_f$=0.1 (10%MeOH/1%NH$_4$OH/CH$_2$Cl$_2$)

$^1$H-NMR(200 MHz, DMSO-d$_6$): δ=2.0 (m, 2H), 3.22 (m, 1H), 3.7 (m,3H), 4.4 (m, 1H), 5.0 (s, OH), 6.32 (m, 2H), 8.15 (m, 2H).

MS (ESP+): m/e 165 (M+H)$^+$.

EXAMPLE 74

1-(4-pyridyl)-3-(5-trifluoromethyl-2-pyridyloxy)pyrrolidine

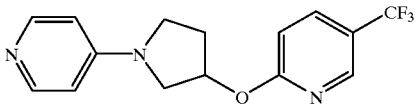

Scale: 648 mg, 3.95 mmol

Method B, using 1-(4-pyridyl)-3-hydroxypyrrolidine and 2-bromo-5-trifluoromethylpyridine. The crude residue was recrystallised from methyl t-butyl ether.

Yield=710 mg (58%)

$R_f$=0.28 (10%MeOH/1%NH$_4$OH/CH$_2$Cl$_2$)

$^1$H-NMR (300 MHz, CDCl$_3$): δ=2.38 (m, 2H), 3.55 (m, 3H), 3.75 (dd, 1H), 5.78 (m, 1H), 6.4 (d, 2H), 6.8 (d, 1H), 7.8 (dd. 1H), 8.22 (d, 2H), 8.45 (m, 1H).

MS (ESP+): m/e 310 (M+H)$^+$.

Found: C,58.5; H,4.7; N,13.3; C$_{15}$H$_{14}$F$_3$N$_3$O requires: C,58.3; H,4.56; N,13.6%.

EXAMPLE 75

1-(4-pyridyl)-3-(5-nitro-2-pyridyloxy)pyrrolidine

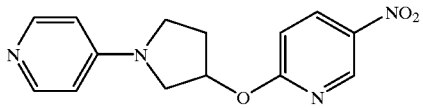

Scale: 500 mg. 3.05 mmol

Method D, using 1-(4-pyridyl)-3-hydroxypyrrolidine and 2-bromo-5-nitropyridine. The residue was purified by chromatography on silica, eluting from 1%MeOH/1%NH$_4$OH/CH$_2$Cl$_2$ to 10%MeOH/1%NH$_4$OH/CH$_2$Cl$_2$ (in 1% increments). The crude product was recrystallised from EtOAc to give a pale brown solid.

Yield=460 mg (53%)

R$_f$=0.41 (10%MeOH/1%NH$_4$OH/CH$_2$Cl$_2$)

$^1$H-NMR (300 MHz, CDCl$_3$): δ=2.4 (m, 2H), 3.58 (m, 3H), 3.8 (dd, 1H), 5.85 (m, 1H), 6.4 (d, 2H), 6.82 (d, 1H), 8.22 (m, 2H), 8.38 (dd, 1H), 9.08 (s, 1H).

MS (ESP+): m/e 287 (M+H)$^+$.

EXAMPLE 76

1-(4-pyridyl)-3-(5-chloro-2-pyridyloxy)pyrrolidine

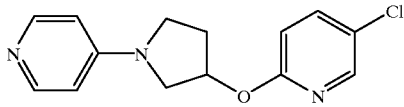

Scale: 500 mg, 3.05 mmol

Method B, using 1-(4-pyridyl)-3-hydroxypyrrolidine and 2,5-dichloropyridine. The crude residue was recrystallised from methyl t-butyl ether.

Yield=570 mg (68%)

R$_f$=0.50 (10%MeOH/1%NH$_4$OH/CH$_2$Cl$_2$)

$^1$H-NMR (300 MHz, CDCl$_3$): δ=2.35 (m, 2H), 3.5 (m, 3H), 3.7 (dd, 1H), 5.65 (m, 1H), 6.38 (m, 2H), 6.65 (d, 1H), 7.55 (dd, 1H), 8.1 (m, 1H), 8.2 (m, 2H).

MS (ESP+): m/e 276 (M+H)$^+$.

EXAMPLE 77

(3R)-1-(4-pyridyl)-3-(5-nitro-2-pyridyloxy)pyrrolidine

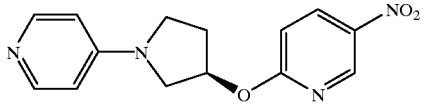

Scale: 500 mg, 3.05 mmol

Method D, using (R)-1-(4-pyridyl)-3-hydroxypyrrolidine and 2-bromo-5-nitropyridine, with 1 hr reaction time. The crude product was recrystallised from EtOAc/hexane.

Yield=480 mg (55%)

R$_f$=0.41 (10%MeOH/1%NH$_4$OH/CH$_2$Cl$_2$)

$^1$H-NMR (300 MHz, CDCl$_3$): δ=2.4 (m, 2H), 3.58 (m, 3H), 3.8 (dd, 1H), 5.85 (m, 1H), 6.4 (d, 2H), 6.82 (d, 1H), 8.22 (m, 2H), 8.38 (dd, 1H), 9.08 (s, 1H).

MS (ESP+): m/e 287 (M+H)$^+$.

The precursor (R)-1-(4-pyridyl)-3-hydroxypyrrolidine was prepared in analogous manner to the racemic material. The NMR spectrum, mass spectrum and R$_f$ were as for the racemate, and the R enantiomer gave an optical rotation (α$_D$) of −22.5 (c=10 mg/ml, MeOH).

EXAMPLE 78

(3R)-1-(4-pyridyl)-3-(5-bromo-2-pyridyloxy)pyrrolidine

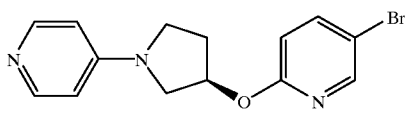

Scale: 500 mg. 3.05 mmol

Method B, using (R)-1-(4-pyridyl)-3-hydroxypyrrolidine and 2,5-dibromopyridine. The crude product was recrystallised from EtOAc/hexane.

Yield=550 mg (57%)

R$_f$=0.41 (10%MeOH/1%NH$_4$OH/CH$_2$Cl$_1$)

$^1$H-NMR (300 MHz, CDCl$_3$): δ=2.35 (m, 2H), 3.5 (m, 3H), 3.72 (dd, 1H), 5.65 (m, 1H), 6.38 (m, 2H), 6.62 (d, 1H), 7.64 (dd, 1H), 8.2 (m, 3H).

MS (ESP+): m/e 320/2 (M+H)$^+$.

Found: C,52.9; H,4.5; N,13.1; C$_{14}$H$_{14}$BrN$_3$O requires: C,52.5; H,4.41; N,13.1%.

EXAMPLE 79

(3R)-1-(4-pyridyl)-3-(5-trifluoromethyl-2-pyridyloxy)pyrrolidine

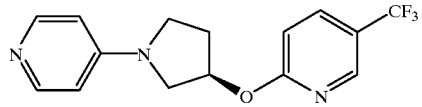

Scale: 500 mg, 3.05 mmol

Method B, using (R)-1-(4-pyridyl)-3-hydroxypyrrolidine and 2-bromo-5-trifluoromethylpyridine. The crude product was recrystallised from EtOAc/hexane.

Yield=230 mg (24%)

R$_f$=0.39 (10%MeOH/1%NH$_4$OH/CH$_2$Cl$_2$)

$^1$H-NMR (300 MHz, CDCl$_3$): δ2.38 (m, 2H), 3.55 (m, 3H), 3.75 (dd, 1H), 5.78 (m, 1H), 6.4 (d, 2H), 6.8 (d, 1H), 7.8 (dd, 1H), 8.22 (d, 2H), 8.45 (m, 1H).

MS (ESP+): m/e 310 (M+H)$^+$.

Found: C,58.6; H,4.8; N,13.4; C$_{15}$H$_{14}$F$_3$N$_3$O requires: C,58.3; H,4.56; N,13.6%.

EXAMPLE 80

(3S)-1-(4-pyridyl)-3-(5-trifluoromethyl-2-pyridylox) pyrrolidine

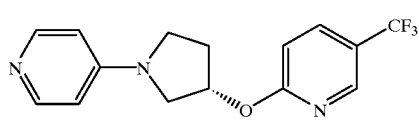

Scale: 500 mg, 3.05 mmol

Method B, using (S)-1-(4-pyridyl)-3-hydroxypyrrolidine and 2-bromo-5-trifluoromethylpyridine. The crude product was recrystallised from EtOAc/hexane.

Yield=300 mg (32%)

$R_f$=0.39 (10%MeOH/1%NH$_4$OH/CH$_2$Cl$_2$)

$^1$H-NMR (200 MHz, CDCl$_3$): δ=2.38 (m, 2H), 3.53 (m, 3H), 3.76 (dd, 1H), 5.78 (m, 1H), 6.4 (d, 2H), 6.8 (d, 1H), 7.8 (dd, 1H), 8.2 (d, 2H), 8.45 (m, 1H).

MS (ESP+): m/e 310 (M+H)$^+$.

Found: C,57.7; H,4.6; N,13.2; C$_{15}$H$_{14}$F$_3$N$_3$O .(0.16H$_2$O) requires: C,57.7; H,4.62; N,13.46%.

The precursor (S)-1-(4-Pyridyl)-3-hydroxypyrrolidine was made by the method used for racemic material. The NMR spectrum, mass spectrum and $R_f$ were as for the racemate, and the S enantiomer gave an optical rotation ($α_D$) of +22.7 (c=10 mg/ml, MeOH). The starting (S)-3-hydroxypyrrolidine was made from (S)-1-benzyl-3-hydroxypyrrolidine (Fluorochem) by hydrogenolysis of the benzyl group (M. M. Bowers Nemia, J. Lee and M. M. Joullie: *Synth. Comm.*, 1983, 13, 117–1123)

EXAMPLE 81

(3S)-1-(4-pyridyl)-3-(5-bromo-2-pyridyloxy) pyrrolidine

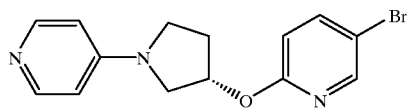

Scale: 500 mg, 3.05 mmol

Method B, using (S)-1-(4-pyridyl)-3-hydroxypyrrolidine and 2.5-dibromopyridine. The crude product was recrystallised from EtOAc/hexane.

Yield=476 mg (49%)

$R_f$=0.41 (10%MeOH/1%NH$_4$OH/CH$_2$Cl$_2$)

$^1$H-NMR (300 MHz, CDCl$_3$): δ=2.35 (m, 2H), 3.5 (m, 3H), 3.72 (dd, 1H), 5.65 (m, 1H), 6.38 (m, 2H), 6.62 (d, 1H), 7.64 (dd, 1H), 8.2 (m, 3H).

MS (ESP+): m/e 320/2 (M+H)$^+$.

Found: C,52.5; H,4.5; N,12.9; C$_{14}$H$_{14}$BrN$_3$O requires: C,52.5; H,4.41; N,13.1%.

EXAMPLE 82

(3S)-1-(4-pyridyl)-3-(5-nitro-2-pyridyloxy) pyrrolidine

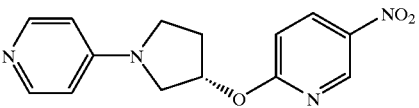

Scale: 500 mg, 3.05 mmol

Method D, using (S)-1-(4-pyridyl)-3-hydroxypyrrolidine and 2-bromo-5-nitropyridine, with 1 hr reaction time. The crude product was recrystallised from methyl t-butyl ether, giving a pale yellow powder.

Yield 150 mg (17%)

$R_f$=0.41 (10%MeOH/1 %NH$_4$OH/CH$_2$Cl$_2$)

$^1$H-NMR (200 MHz, CDCl$_3$): δ=2.4 (m, 2H), 3.55 (m, 3H), 3.8 (dd, 1H), 5.85 (m, 1H), 6.42 (m, 2H), 6.82 (d, 1H), 8.22 (m, 2H), 8.38 (dd, 1H), 9.08 (d, 1H).

MS (ESP+): m/e 287 (M+H)$^+$.

EXAMPLE 83

1-(4-pyridyl)-3-(5-methyoxycarbonyl-2-pyridyloxy) pyrrolidine

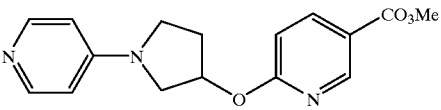

Scale: 2.0 g, 12.2 mmol

Method D, using 1-(4-pyridyl)-3-hydroxypyrrolidine and methyl 6-chloronicotinate. The crude product was recrystallised from aqueous ethanol.

Yield=2.43 g (67%)

$R_f$=0.31 (10%MeOH/1%NH$_4$OH/CH$_2$Cl$_2$)

$^1$H-NMR (200 MHz, CDCl$_3$): δ=2.38 (m, 2H), 3.53 (m, 3H), 3.75 (dd, 1H), 3.92 (s, 3H), 5.81 (m, 1H), 6.4 (d, 2H), 6.72 (d, 1H), 8.16 (m, 3H), 8.82 (m, 1H).

MS (ESP+): m/e 300 (M+H)$^+$.

Found: C,60.7; H,5.6; N,13.0; C$_{16}$H$_{17}$N$_3$O$_3$.(H$_2$O) requires: C,60.5; H,6.0; N,13.2%.

EXAMPLE 84

1-(4-pyridyl)-3-(4-bromophenyloxy)pyrrolidine

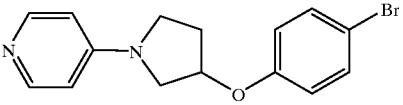

Scale: 2.44 mmol

Method E, using 1-(4-pyridyl)-3-hydroxypyrrolidine and 4-bromophenol. The product was further purified by recrystallisation from MTBE, giving a white solid.

Yield=187 mg (24%)

$R_f$=0.49 (10%MeOH/1%NH$_4$OH/CH$_2$Cl$_2$)

$^1$H-NMR (200 MHz CDCl$_3$): d=2.3 (m, 2H), 3.5 (m, 3H), 3.65 (m, 1H), 5.05 (m, 1H), 6.4 (d, 2H), 6.78 (dd, 2H), 7.42 (dd, 2H), 8.25 (dd, 2H).

MS (CI): m/e 319 (M+H)$^+$.

Found: C,56.5; H,4.7; N,8.7; Cl5H15BrN20 requires: C,56.4; H,4.74; N,8.78%.

EXAMPLE 85

1-(4-pyridyl)-3-(4-trifluoromethylphenyloxy) pyrrolidine

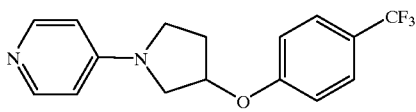

Scale: 2.44 mmol

Method E, using 1-(4-pyridyl)-3-hydroxypyrrolidine and 4-trifluoromethylphenol. The product was further purified by trituration with hexane, giving a white solid.

Yield=278 mg (37%)

$R_f$=0.44 (10%MeOH/1%NH$_4$OH/CH$_2$Cl$_2$)

$^1$H-NMR (200 MHz, CDCl$_3$): d=2.35 (m, 2H), 3.55 (m, 3H), 3.72 (dd, 1H), 5.14 (m, 1H), 6.4 (dd, 2H), 6.96 (dd, 2H), 7.60 (dd, 2H), 8.25 (dd, 2H).

MS (CI): m/e 309 (M+H)$^+$.

Found: C,62.0; H,5.0; N,9.1; C$_{16}$H$_{15}$F$_3$N$_2$O requires: C,62.3; H,4.90; N,9.09%.

EXAMPLE 86

1-(4-pyridyl)-3-(4-(trifluoromethylthio)phenyloxy) pyrrolidine

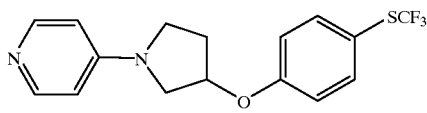

Scale: 2.44 mmol

Method E, using 1-(4-pyridyl)-3-hydroxypyrrolidine and 4-(trifluoromethylthio)phenol. The product was further purified by trituration with diethyl ether, giving a white solid.

Yield=50 mg (6%)

$R_f$=0.42 (10%MeOH/1%NH$_4$OH/CH$_2$Cl$_2$)

$^1$H-NMR (200 MHz, CDCl$_3$): d=2.48 (m, 2H), 3.77 (m, 3H), 3.92 (dd, 1H), 5.22 (m, 1H), 6.68 (d, 2H), 6.92 (d, 2H), 7.61 (d, 2H), 8.16 (d, 2H).

MS (CI): m/e 341 (M+H)$^+$.

EXAMPLE 87

1-(4-pyridyl)-3-(4-(methylthio)phenyloxy) pyrrolidine

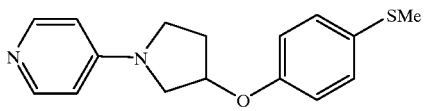

Scale: 3.21 mmol

Method E, using 1-(4-pyridyl)-3-hydroxypyrrolidine and 4-(methylthio)phenol. The product was further purified by recrystallisation from MTBE, giving a white powder.

Yield=183 mg (37%)

$R_f$=0.32 (10%MeOH/1%NH$_4$OH/CH$_2$Cl$_2$)

$^1$H-NMR (300 MHz, CDCl$_3$): d=2.25 (m,1H), 2.36 (m, 1H), 2.44 (s, 3H), 3.52 (m, 3H), 3.64 (dd, 1H), 5.04 (m, 1H), 6.4 (d, 2H), 6.82 (d, 2H), 7.24 (d, 2H), 8.22 (d, 2H).

MS (CI): m/e 287 (M+H)$^+$.

Found: C,67.3; H,6.4; N,9.7; C$_{16}$H$_{18}$N$_2$OS requires: C,67.1; H,6.34; N,9.78%.

EXAMPLE 88

1-(4-pyridyl)-3-(4-(trifluoromethyloxy)phenyloxy) pyrrolidine

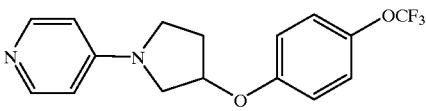

Scale: 2.44 mmol

Method E, using 1-(4-pyridyl)-3-hydroxypyrrolidine and 4-(trifluoromethyloxy)phenol. The product was further purified by trituration with hexane, giving a white powder.

Yield=325 mg (41%)

$R_f$=0.32 (10%MeOH/1%NH$_4$OH/CH$_2$Cl$_2$)

$^1$H-NMR (300 MHz, CDCl$_3$): d=2.28 (m,1H), 2.38 (m, 1H), 3.52 (m, 3H), 3.64 (dd, 1H), 5.04 (m, 1H), 6.4 (d, 2H), 6.85 (d, 2H), 7.18 (d, 2H), 8.22 (d, 2H).

MS (CI): m/e 325 (M+H)$^+$.

Found: C,59.1; H,4.8; N,8.9; C$_{16}$H$_{15}$F$_3$N$_2$O requires: C,59.3, H,4.66; N,8.64%.

EXAMPLE 89

1-(4-pyridyl)-3-(4-chlorophenyloxy)pyrrolidine

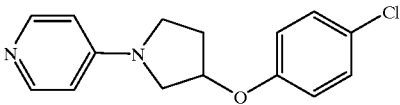

Scale: 2.44 mmol

Method E, using 1-(4-pyridyl)-3-hydroxypyrrolidine and 4-chlorophenol. The product was further purified by recrystallisation from MTBE, giving a white solid.

Yield=302 mg (45%)

$R_f$0.33 (10%MeOH/1%NH$_4$OH/CH$_2$Cl$_2$)

$^1$H-NMR (300 MHz, CDCl$_3$): d=2.25 (m,1H), 2.38 (m, 1H), 3.5 (m, 3H), 3.64 (dd, 1H), 5.02 (m, 1H), 6.38 (d, 2H), 6.82 (d, 2H), 7.24 (d, 2H), 8.22 (d, 2H).

MS (CI): m/e 275 (M+H)$^+$.

Found: C,65.4; H,5.6; N,10.1; C$_{15}$H$_{15}$ClN$_2$O requires: C,65.6; H,5.50; N,10.2%.

EXAMPLE 90

1-(4-pyridyl)-3-(4-nitrophenyloxy)pyrrolidine

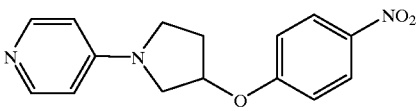

Scale: 1.83 mmol

Method D, using 1-(4-pyridyl)-3-hydroxypyrrolidine and 4-bromonitrobenzene. The product was purified by column chromatography, eluting sequentially with CH$_2$Cl$_2$; 7% MeOH/CH$_2$Cl$_2$; 7%MeOH/1%NH$_4$OH/CH$_2$Cl$_2$; 10%MeOH/1%NH$_4$OH/CH$_2$Cl$_2$, giving a brown foam.

Yield=71 mg (14%)

$R_f$=0.41 (10%MeOH/1%NH$_4$OH/CH$_2$Cl$_2$)

$^1$H-NMR (300 MHz, CDCl$_3$): d=2.4 (m, 2H), 3.6 (m, 3H), 3.78 (dd, 1H), 5.0 (m, 1H), 6.42 (d, 2H), 6.98 (d, 2H), 8.22 (d, 4H).

MS (CI): m/e 285 (M+H)$^+$.

EXAMPLE 91

(3R)-1-(4-pyridyl)-3-(3,5-dichloro-2-pyridyloxy) pyrrolidine

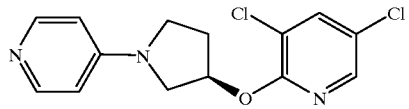

Scale: 1.83 mmol

Method B,. using (3R)-1-(4-pyridyl)-3-hydroxypyrrolidine and 2,3,5-trichloropyridine. The product was purified by column chromatography, eluting sequentially with $CH_2-Cl_2$; 7% $MeOH/CH_2Cl_2$; 7%MeOH/1%$NH_4OH/CH_2Cl_2$; 10%MeOH/1%$NH_4OH/CH_2Cl_2$, giving a brown foam.

Yield=494 mg (87%)
$R_f$=0.31 (10%MeOH/1%$NH_4OH/CH_2Cl_2$)
$^1$H-NMR (300 MHz, $CDCl_3$): d=2.4 (m, 2H), 3.55 (m, 3H), 3.78 (dd, 1H), 5.68 (m, 1H), 6.42 (d, 2H), 7.63 (d, 1H), 8.02 (s, 1H), 8.22 (d, 2H).
MS (CI): m/e 310/312/314 (M+H)$^+$.
Found: C,52.8; H,4.2; N,13.2; $C_{14}H_{13}Cl_2N_3O \cdot (0.4H_2O)$ requires: C,52.9; H,4.38; N,13.24%.

EXAMPLE 92

(3R)-1-(4-pyridyl)-3-(3,5-dichloro-2-pyridyloxy) pyrolidine

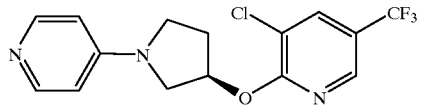

Scale: 1.83 mmol

Method B, using (3R)-1-(4-pyridyl)-3-hydroxypyrrolidine and 2,3-dichloro-5-trifluoromethylpyridine. The product was purified by column chromatography, eluting sequentially with $CH_2Cl_2$; 7%$MeOH/CH_2Cl_2$; 7%$MeOH/1$%$NH_4OH/CH_2Cl_2$; 10%$MeOH/1$%$NH_4OH/CH_2Cl_2$, giving a brown gum which was further purified by trituration with ether.

Yield=69mg (11%)
$R_f$=0.36 (10%MeOH/1%$NH_4OH/CH_2Cl_2$)
$^1$H-NMR (300 MHz, $CDCl_3$): d=2.55 (m, 2H), 3.8 (m, 3H), 3.96 (dd, 1H), 5.86 (m, 1H), 6.65 (d, 2H), 7.9 (s, 1H), 8.18 (d, 2H), 8.36 (s, 1H).
MS (CI): m/e 344/346 (M+H)$^+$.

EXAMPLE 93

(3R)-1-(4-pyridyl)-3-(3chloro-2-pyridyloxy) pyrrolidine

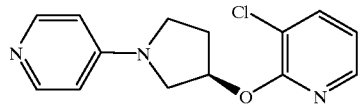

Scale: 1.83 mmol

Method B, using (3R)-1-(4-pyridyl)-3-hydroxypyrrolidine and 2,3-dichloropyridine. The product was purified by column chromatography, eluting sequentially with $CH_2Cl_2$; 7% $MeOH/CH_2Cl_2$; 7%MeOH/1%$NH_4OH/CH_2Cl_2$; 10%MeOH/1%$NH_4OH/CH_2Cl_2$, giving an off-white solid which was further purified by recrystallisation from MTBE.

Yield=303 mg (60%)
$R_f$=0.47 (10%MeOH/1%$NH_4OH/CH_2Cl_2$)
$^1$H-NMR (300 MHz, $CDCl_3$): d=2.4 (m, 2H), 3.55 (m, 3H), 3.78 (dd, 1H), 5.75 (m, 1H), 6.4 (d, 2H), 6.85 (dd, 1H), 7.62 (d, 1H), 8.02 (m, 1H), 8.2 (d, 2H).
MS (CI): m/e 276/278 (M+H)$^+$.
Found: C,61.0; H,5.1; N,15.4; $C_{14}H_{14}ClN_3O$ requires: C,61.0; H,5.12; N,15.2%.

EXAMPLE 94

1-(2-methyl-4-pyridyl)-3-(5-nitro-2-pyridyloxy) pyrrolidine

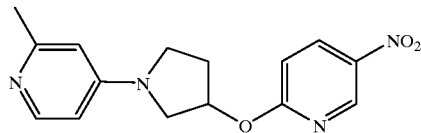

Scale: 318 mg, 1.76 mmol

Method A, using 2-methyl-4-chloropyridine and 3-(5-nitro-2-pyridyloxy)pyrrolidine (made in an analogous manner to 3-(5-trifluoromethyl-2-pyridyloxy)pyrrolidine above). The solvents were evaporated and the residue was purified by column chromatography on silica, eluting with $Et_2O$, then EtOAc, then 5%MeOH/1%$NH_4OH/CH_2Cl_2$, then 10%MeOH/1%$NH_4OH/CH_2Cl_2$, giving the product as a yellow gum which was triturated with ether, giving a hygroscopic solid.

Yield=171 mg (49%)
$R_f$=0.28 (5%MeOH/1%$NH_4OH/CH_2Cl_2$)
$^1$H-NMR (200 MHz, $CDCl_3$): d=2.4 (m, 2H), 2.45 (s, 3H), 3.55 (m, 3H), 3.78 (dd, 1H), 5.84 (m, 1H), 6.25 (m, 2H), 6.8 (d, 1H), 8.12 (d, 1H), 8.36 (dd, 1H), 9.08 (d, 1H).
MS (ESP+): m/e 301 (M+H)$^+$.

EXAMPLE 95

1-(5-bromo-2-pyridyl)-4-(4-pyridyl)piperazine

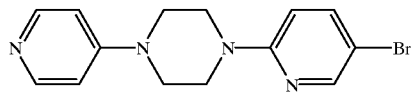

A mixture of 1-(4-pyridyl)piperazine (3.26 g, 20 mmol) and 2,5-dibromopyridine (2.36 g) was heated gradually on an oil bath up to 200° C. At approximately 150° C. a clear, slightly coloured melt was obtained and at approximately 180° C. a vigorous reaction set in which caused the melt to darken markedly. The now-dark melt was heated at 200° C. for 10 minutes then allowed to cool to room temperature. The solid reaction mixture was dissolved in methanol (100 mL) and poured into water (100–150 mL). The resultant precipitate was collected, washed with water, dried, then recrystallised from hot aqueous methanol to give the product (1.6 g, 25% yield) as a buff-coloured solid: m.p. 176–180° C.; NMR (DMSO-$d_6$), 3.32 (4H, m), 3.50 (4H, m), 6.72 (2H, m), 6.75 (1H, d), 7.59 (1H, dd), 8.05 (3H, m); Found: MH$^+$, 319/321; $C_{14}H_{15}BrN_4$ requires MH$^+$, 319/321.

EXAMPLE 96

1-(4-pyridyl)-4-((4-benzyloxy)phenyloxy)piperidine

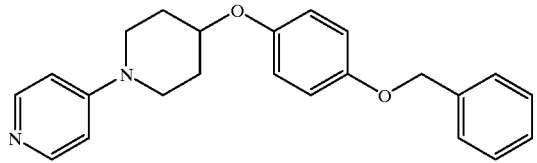

Scale: 5.0 mmol

Method E, using hydroquinone monobenzyl ether and 1-(4-pyridyl)-4-hydroxypiperidine. The residue was purified by column chromatography, eluting sequentially with EtOAc; $CH_2Cl_2$; 5%MeOH/$CH_2Cl_2$; 10%MeOH/$CH_2Cl_2$; 10%MeOH/$CH_2Cl_2$ giving an off-white solid.

Yield=232 mg (13%)

$R_f$32 0.25 (10%MeOH/$CH_2Cl_2$)

$^1$H-NMR (250 MHz, $CDCl_3$): δ=1.95 (m, 4H), 3.30 (m, 2H), 3.65 (m, 2H), 4.43 (m, 1H), 5.02 (s, 2H), 6.68 (m, 2H), 6.90 (m, 4H), 7.38 (m, 5H), 8.27 (d, 2H).

MS (ESP+): m/e 361 (M+H)$^+$.

EXAMPLE 97

1-(5-nitro2-pyridyl)-4-(4-pyridyl)piperazine

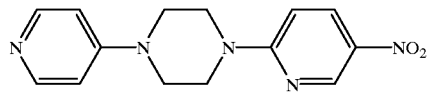

Scale: 350 mg, 2.15 mmol

Method F. using 2-bromo-5-nitropyridine. The product was isolated by filtration of the reaction mixture, washed with water and dried azeotropically with toluene.

Yield=490 mg.(80%) yellow powder $R_f$=0.15 (10%MeOH/$CH_2Cl_2$)

$^1$H-NMR (200 MHz, DMSO-$d_6$): δ=3.52 (m, 4H), 3.92 (m, 4H), 6.82 (m, 2H), 6.98 (d, 1H), 8.23 (m 3H), 9.0 (d, 1H).

MS (CI+): m/e 286.6 (M+H)$^+$.

EXAMPLE 98

1-(5-trifluoromethyl-2-pyridyl)-4-(4-pyridyl) piperazine

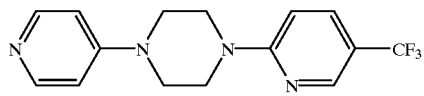

Scale: 325 mg, 2.0 mmol

Method F, using 2-bromo-5-trifluoromethylpyridine. Purification by column chromatography on silica, eluting with $CH_2Cl_2$ and increasing gradually to 10%MeOH/$CH_2Cl_2$ gave the product as an off-white solid.

Yield=150 mg (24%) cream solid $R_f$=0.35 (10%MeOH/$CH_2Cl_2$)

$^1$H-NMR (250 MHz, $CDCl_3$): δ=3.5 (m, 4H), 3.82 (m, 4H), 6.66 (m, 3H), 7.66 (dd, 1H), 8.28 (m, 2H), 8.42 (m 1H).

MS (CI+): m/e 309 (M+H)$^+$.

Found: C, 58.4; H, 4.9; N, 17.9; $C_{15}H_{15}F_3N_4$ requires: C58.4; H, 4.90; N, 18.2%.

EXAMPLE 99

1-(4-pyridyl)-3-(4-benzyloxyphenoxy)pyrrolidine

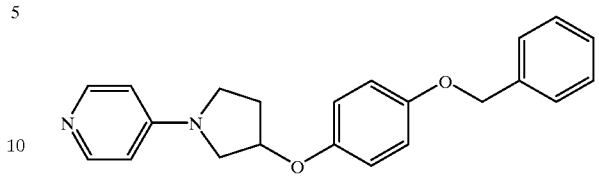

Scale: 2.6 g, 8.52 mmol

Method A using 4-chloropyridine hydrochloride and 3-(4-benzyloxyphenoxy)pyrrolidine hydrochloride. The reaction mixture was taken to pH 8.5 using aqueous NaOH solution and the product was extracted with $CH_2Cl_2$. The combined organic extracts were washed with brine, dried ($Na_2SO_4$) and concentrated in vacuo, and the residue columned on silica, eluting with 10%MeOH/1%$NH_4$OH/$CH_2Cl_2$, giving a yellow gum.

Yield=1.55 g (53%)

$R_f$=0.35 (10%MeOH/1%$NH_4$OH/$CH_2Cl_2$)

$^1$H-NMR (200 MHz, $d^6$-DMSO): d=2.24 (m, 2H), 3.40 (m, 3H), 3.6(dd, 1H), 5.05 (s, 2H), 5.07 (m, 1H), 6.52 (d, 2H), 6.93 (m, 4H), 7.40 (m. 5H), 8.11 (d, 2H).

MS (ESP+): m/e 347 (M+H)$^+$.

Found: C, 74.3; H, 6.4; N, 7.7; $C_{22}H_{22}N_2O_2$.0.5$H_2O$ requires: C, 74.2; H, 6.2; N, 7.9%.

The precursor 3-(4-benzyloxyphenoxy)pyrrolidine hydrochloride was prepared in two steps from hydroquinone monobenzyl ether as follows:

3-(4-benzyloxyphenoxy)pyrrolidine hydrochloride

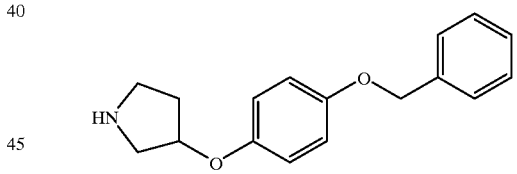

Scale: 3.82 g, 19.1 mmol.

Method E using hydroquinone monobenzyl ether and 1-(tert-butyloxycarbonyl)-3pyrrolidinol. The solvent was evaporated and the residue columned on silica, eluting sequentially with $CH_2Cl_2$;30%EtOAc/hexane giving a yellow oil. This was dissloved in EtOAc (200 ml) under Ar and a saturated solution of hydrogen chloride in $Et_2O$ (100 ml) was added, The mixture was stirred for 4 h. The product was filtered off as a white solid.

Yield: 2.61 g (45%)

$R_f$=0.24 (10%MeOH/1%$NH_4$OH/$CH_2Cl_2$)

$^1$H-NMR (250 MHz, $d^6$-DMSO): d=2.12 (m, 2H), 3.27 (m, 3H), 3.41 (dd, 1H), 5.03 (m, 1H), 5.05 (s, 2H), 6.94 (m, 4H), 7.37 (m, 5H), 9.51 (br s, 1H).

MS (ESP+): m/e 270 (M+H)$^+$.

Found: C, 66.5; H, 6.6; N, 4.6; $C_{17}H_{20}ClNO_2$ requires: C, 66.8; H, 6.6; N, 4.6%.

EXAMPLE 100

1-(5-chloro-2-pyridyl)-4-(4-pyridyl)piperazine

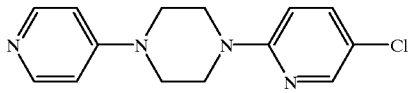

Scale: 312 mg, 1.91 mmol

Method F, using 2,5-dichloropyridine. The residue was purified by column chromatography on silica, eluting with $CH_2Cl_2$, then 5%MeOH/$CH_2Cl_2$.

Yield=30 mg (6%) light brown solid $R_f$=0.3 (10%MeOH/$CH_2Cl_2$)

$^1$H-NMR (300 MHz, CDCl$_3$): δ=3.43 (m, 4H), 3.64 (m, 4H), 6.6 (d, 1H), 6.7 (d, 2H), 7.23 (dd, 1H), 8.15 (m, 1H), 8.32 (d, 2H).

MS (ESP+): m/e 275/7 (M+H)$^+$.

EXAMPLE 101

1-(4-(2-methyl)pyridyl)-4-((4-benzyloxy)phenyloxy)piperidine

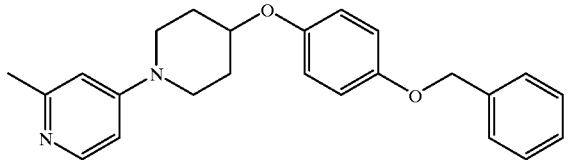

Scaled: 1.3 mmol (4-Benzyloxy)phenyloxy)piperidine (1 eq) (made from 1-t-butyloxycarbonyl-4-hydroxypiperidine by Mitsunobu reaction with hydroquinone monobenzyl ether followed by treatment with trifluoroacetic acid) and 2-methyl-4-chloropyridine (2 eq) were heated in t-butanol (2.5 ml) and aqueous HCl (2M; 0.1 ml) at reflux overnight. The solvents were evaporated and the residue partitioned between $CH_2Cl_2$ and 10% aqueous potassium carbonate solution. The organic layer was washed with water and brine. dried over sodium sulphate and concentrated. The residue was purified by column chromatography, elutin, sequentially with $CH_2Cl_2$; 5%MeOH/$CH_2Cl_2$; 10%MeOH/$CH_2Cl_2$; 10%MeOH/1%NH$_4$OH/$CH_2Cl_2$ giving an off-white powder.

Yield=70 mg (14%)

$R_f$=0.44 (10%MeOH/$CH_2Cl_2$)

$^1$H-NMR (250 MHz, CDCl$_3$): δ=2.0 (m, 4H), 2.62 (s, 3H), 3.58 (m, 2H), 3.70 (m, 2H), 4.52 (m, 1H), 5.02 (s, 2H), 6.58 (m, 1H), 6.68 (dd, 1H), 6.88 (m, 4H), 7.38 (m, 5H), 8.08 (d, 2H).

MS (ESP+): m/e 375 (M+H)$^+$.

EXAMPLE 102

1-(4-pyridyl)-3-(5-benzyloxy-2-pyridyloxy)pyrrolidine

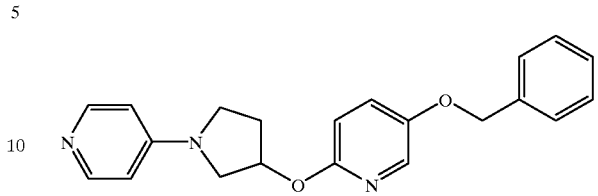

Scale: 6.02 g, 27.4 mmol

Method B, using using 1-(4-pyridyl)-3-hydroxypyrrolidine and 2-chloro-5-benzyloxypyridine, heating to 120° C. for 3 h. After cooling the t-butanol was removed on a rotary evaporator. The dark residue was dissolved in $CH_2Cl_2$ and the solution washed with 10% aqueous NaOH solution before concentration in vacuo. The residue was purified by column chromatography, eluting sequentially with $CH_2Cl_2$;Et$_2$O;10%MeOH/1%NH$_4$OH/$CH_2Cl_2$ giving a brown oil.

Yield=5.70 g (66%)

$R_f$=0.38 (10%MeOH/1%NH$_4$OH/$CH_2Cl_2$)

$^1$H-NMR (300 MHz, CDCl$_3$): d=2.33 (m, 2H), 3.5 (m, 3H), 3.71 (dd, 1H), 5.04 (s, 2H), 5.63 (m, 1H), 6.40 (d, 2H), 6.64 (d, 1H), 7.26 (dd, 1H), 7.3 (m, 5H), 7.88 (d, 1H), 8.21 (d, 2H).

MS (ESP+): m/e 348 (M+H)$^+$.

The precursor 2-chloro-5-benzyloxypyridine was prepared in three steps from 5-amino-2-chloropyridine as follows:

2-chloro-5-acetoxypyridine

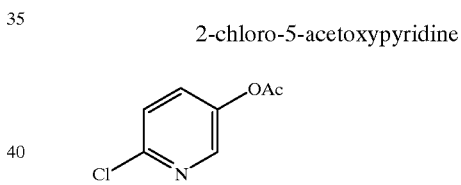

Scale: 25.9 g, 201 mmol

Method: a solution of 5-amino-2-chloropyridine (25.9 g, 201 mmol) in ethanol (185 ml) was cooled in an ice-methanol bath. 50% aqueous tetrafluoroboric acid (78 ml, 442 mmol) was added. When the internal temperature reached −5° C. isoamyl nitrite (28.4 ml, 211 mmol) was added dropwise keeping the temperature below 0° C. After addition the reaction mixture was stirred at 0° C. for 30 minutes. An orange solid appeared which was collected on a Buchner funnel, washed with Et$_2$O and dried on the Buchner funnel for 15 minutes, The solid was dissolved in acetic anhydride (240 ml) and the resulting solution warmed slowly to 70° C. Heating was continued for 4 hours during which time N$_2$ gas was evolved. The mixture was allowed to cool then concentrated in vacuo. The residue was dissolved in Et$_2$O (300 ml) and washed three times with water, then with brine, dried (Na$_2$SO$_4$) and concentrated in vacuo giving a red-brown oil. The product was purified by Kügelrohr distillation (oven temperature 110° C., 1.6 mbar) giving a white solid.

Yield=16.5 g (48%)

$R_f$=0.74 (10% Et$_2$O/$CH_2Cl_2$)

$^1$H-NMR (300 MHz, CDCl$_3$): d=2.33 (s, 3H), 7.34 (d, 1H), 7.47 (dd, 1H), 8.21 (d, 1H).

2-chloro-5-hydroxypyridine

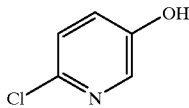

Scale: 16.5 g, 96.2 mmol
Method: 2-chloro-5-acetoxypyridine (16.5 g, 96.2 mmol) was dissolved in 2M aqueous KOH solution (125 ml) with ice-bath cooling. The resulting solution was stirred at 4° C. for 3 hours after which time the reaction was judged complete by tlc. The reaction mixture was neutralised by the addition of acetic acid (approx. 10 ml) whereupon a white solid appeared. The product was collected on a Buchner funnel and dried under high vacuum at 40° C.
Yield=11.9 g (96%)
$R_f$=0.21 (10% $Et_2O/CH_2Cl_2$)
$^1$H-NMR (300 MHz, $d^6$-DMSO): d=7.2 (m, 2H), 7.87 (d, 1H).
MS (ESP+): m/e 130/2 (M+H)$^+$.
Found: C, 46.3; H, 3.1; N, 10.7; $C_5H_4ClNO$ requires: C, 46.4; H, 3.11; N, 10.8%.

2-chloro-5-benzyloxypyridine

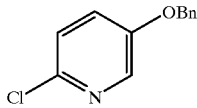

Scale: 6.05 g, 46.7 mmol
Method: under argon, 2-chloro-5-hydroxypyridine (6.05 g, 46.7 mmol) was dissolved in anhydrous DMF (50 ml) and the resulting solution cooled in an ice-water bath. Sodium methoxide (2.78 g, 51.4 mmol) was added and the mixture stirred for 10 minutes. Benzyl bromide (8.79 g, 51.4 mmol) was added and the resulting mixture stirred for 90 minutes with gradual warming to room temperature. The mixture was poured into ice-water (600 ml), The mixture was extracted thrice with $Et_2O$ and the combined extracts washed with water and brine. dried ($MgSO_4$) and concentrated in vacuo giving a clear yellow oil. The product was purified by column chromatography, eluting sequentially with 10% $Et_2O$/isohexane;25% $Et_2O$/isohexane yielding a white solid.
Yield=8.18 g (80%)
$R_f$=0.36 ($CH_2Cl_2$)
$^1$H-NMR (300 MHz, $CDCl_3$): d=5.09 (s, 2H), 7.27 (d, 1H), 7.35 (m, 6H), 8.14 (d, 1H).
MS (ESP+): m/e 220/2 (M+H)$^-$.

EXAMPLE 103

1-(4-pyrimidyl)-3-(5-trifluoromethyl-2-pyridyloxy) pyrrolidine

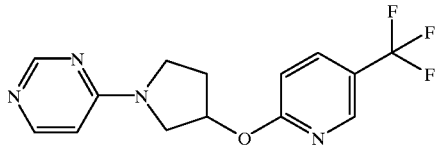

Scale: 1.7 mmol
Method A in 10% aqueous isopropanol, using 4-chloropyrimidine and 3-(5-trifluoromethyl-2-pyridyloxy) pyrrolidine. After evaporation of the solvents, the residue was purified by column chromatography, eluting sequentially with $CH_2Cl_2$; 5%MeOH/$CH_2Cl_2$; 10%MeOH/$CH_2Cl_2$; 10%MeOH/1%$NH_4OH$/$CH_2Cl_2$ giving an off-white solid.
Yield=379 mg (72%)
$R_f$=0.53 (10%MeOH/1%$NH_4OH$/$CH_2Cl_2$)
$^1$H-NMR (200 MHz, $CDCl_3$): δ=2.38 (m, 2H), 3.75 (m, 4H), 5.78 (m, 1H), 6.30 (d, 1H), 6.80 (d, 1H), 7.80 (d, 1H) 8.18 (d, 1H), 8.42 (s, 1H), 8.60 (s, 1H).
MS (ESP+): m/e 311 (M+H)$^+$.
Found: C, 53.8; H, 4.2; N, 17.6; $C_{14}H_{13}F_3N_4O$ requires: C, 54.2; H, 4.22; N, 18.1%.

EXAMPLE 104

1-(4-pyridyl)-3-(5-benzylthio-2-pyridyloxy) pyrrolidine

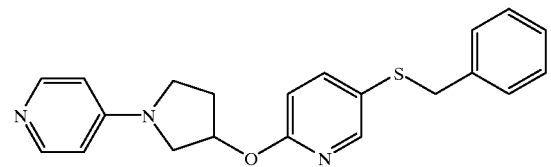

Scale: 524 mg, 3.19 mmol
Method B, 0.5 M in anhydrous THF and without tetra-n-butylammonium bromide. using 1-(4-pyridyl)-3-hydroxypyrrolidine and 2-chloro-5-benzylthio-pyridine. The product was purified by column chromatography, eluting sequentially with $Et_2O$; 5%MeOH/$CH_2Cl_2$; 10%MeOH/1%$NH_4OH$/$CH_2Cl_2$ giving a pale yellow gum.
Yield=517 mg (45%)
$R_f$=0.33 (10%MeOH/1%$NH_4OH$/$CH_2Cl_2$)
$^1$H-NMR (300 MHz, $CDCl_3$): d=2.35 (m, 2H), 3.5 (m, 3H), 3.72 (dd, 1H), 3.96 (s, 2H), 5.66 (m, 1H), 6.41 (d, 2H), 6.59 (d, 1H), 7.17 (m, 2H), 7.24 (m, 3H), 7.45 (dd, 1H, 8.07 (d, 1H), 8.10 (d, 2H).
MS (ESP+): m/e 364 (M+H)$^+$.
The precursor 2-chloro-5-benzylthiopyridine was prepared in two steps from 5-amino-2-chloropyridine as follows:

2-chloro-5-benzylthiopyridine

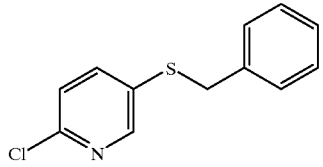

Scale: 628 mg, 3.68 mmol
Method: 2-chloro-5-thiocyanopyridine (628 mg, 3.68 mmol) and benzyl bromide (692 mg, 4.05 mmol) were dissolved in THF (6 ml) and a solution of potassium hydroxide (512 mg, 9.13 mmol) in water (5 ml) was added. The resulting mixture was heated to 100° C. for 2 hours. The mixture was allowed to cool then extracted with $Et_2O$ (3×10 ml), The combined extracts were dried ($MgSO_4$) and concentrated in vacuo, yielding a yellow oil.
Yield=828 mg (95%)
$R_f$=0.45 ($CH_2Cl_2$)
$^1$H-NMR (250 MHz, $CDCl_3$): d=4.06 (s, 2H), 7.18 (d, 1H), 7.25 (m, 5H), 7.48 (dd, 1H), 8.26 (d, 1H).

MS (ESP+): m/e 236/8 (M+H)+.

2-chloro-5-thiocyanopyridine

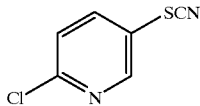

Scale: 5.42 g, 42.1 mmol

Method: 5-amino-2-chloropyridine (5.42 g, 42.1 mmol) was dissolved in concentrated aqueous hydrochloric acid (75 ml) and the resulting solution cooled in an ice-methanol bath. A solution of sodium nitrite (3.58 g, 42.2 mmol) in water (15 ml) was added slowly, keeping the internal reaction temperature below 0° C. After addition the reaction mixture was stirred at 0° C. for 30 minutes then added portionwise to a stirred solution of copper (I) thiocyanate (2.8 g, 23 mmol) and potassium thiocyanate (25 g) in water (525 ml), After addition the mixture stirred for 15 minutes at room temperature. The mixture was filtered through a celite pad, and the pad washed thoroughly with Et$_2$O. The layers were separated and the aqueous layer extracted with Et$_2$O (3×100 ml), The combined organic phases were washed with water, brine and saturated aqueous NaHCO$_3$ solution, dried (MgSO$_4$) and concentrated in vacuo, yielding a yellow oil which solidified on standing. The crude product was purified by Küigelrohr distillation (oven temperature 125° C., 2.4 mbar) yielding a white solid.

Yield=2.55 g (35%)

$^1$H-NMR (300 MHz, CDCl$_3$): d=7.44 (d, 1H), 7.88 (dd, 1H), 8.54 (d, 1H).

MS (CI−): m/e 171/3 (M+H)+.

EXAMPLE 105

1(4-pyridyl)-3-(5-(4-methoxybenzyl)thio-2-pyridyloxy)pyrrolidine

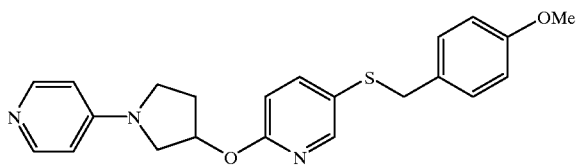

Scale: 88 mg, 0.33 mmol

Method B, 0.5 M in anhydrous THF and without tetra-n-butylammonium bromide, using 1-(4-pyridyl)-3-hydroxypyrrolidine and 2-chloro-5-(4-methoxybenzyl)thiopyridine. The product was purified by column chromatography, eluting sequentially with Et$_2$O; 5%MeOH/CH$_2$Cl$_2$; 10%MeOH/1%NH$_4$OH/CH$_2$Cl$_2$ giving a pale yellow gum.

Yield=102 mg (78%)

R$_f$=0.30 (10%MeOH/1%NH$_4$OH/CH$_2$C$_2$)

$^1$H-NMR (300 MHz, CDCl$_3$): d=2.36 (m, 2H), 3.52 (m, 3H), 3.74 (dd, 1H), 3.78 (s, 3H), 3.90 (s, 2H), 5.67 (m, 1H), 6.44 (d, 2H), 6.58 (d, 1H), 6.79 (d, 2H), 7.07 (d, 2H), 7.45 (dd, 1H), 8.06 (d, 1H), 8.20 (d, 2H).

MS (ESP+): m/e 394 (M+H)+.

The precursor 2-chloro-5-(4-methoxybenzyl)thiopyridine was prepared in two steps from 5-amino-2-chloropyridine as follows:

2-chloro-5-(4-methoxybenzyl)thiopyridine

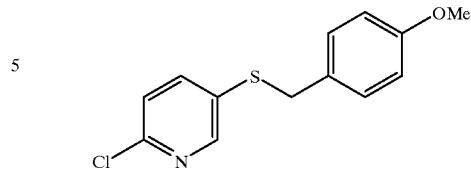

Scale: 98 mg, 0.574 mmol

Method: 2-chloro-5-thiocyanopyridine (98 mg, 0.574 mmol) and benzyl bromide (90 mg, 0.574 mmol) were dissolved in THF (2.5 ml) and a solution of potassium hydroxide (80 mg. 1.44 mmol) in water (2.5 ml) was added. The resulting mixture was heated to 85° C. for 1.5 hours. The mixture was allowed to cool then extracted with Et$_2$O (3×10 ml), The combined extracts were dried (MgSO$_4$) and concentrated in vacuo, yielding a yellow oil.

Yield=92.5 mg (63%)

R$_f$=0.45 (CH$_2$Cl$_2$)

$^1$H-NMR (300 MHz, CDCl$_3$): d=3.78 (s, 3H), 4.03 (s, 2H), 6.81 (d, 2H), 7.15 (d, 2H), 7.19 (d, 1H), 7.48 (dd, 1H), 8.26 (d, 1H).

1-(4-pyridyl)-3-(5-(4-thiazolyl)methylthio-2-pyridyloxy)pyrrolidine

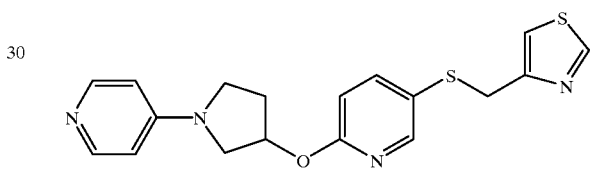

Scale: 125 mg, 0.515 mmol

Method B, 0.5 M in anhydrous THF and without tetra-n-butylammonium bromide, using 1-(4-pyridyl)-3-hydroxypyrrolidine and 2-chloro-5-(4-thiazolyl)methylthiopyridine. The product was purified by column chromatography, eluting sequentially with Et$_2$O;10%MeOH/1%NH$_4$OH/CH$_2$Cl$_2$ giving a pale yellow gum.

Yield=125 mg (66%)

R$_f$=0.30 (10%MeOH/1%NH$_4$OH/CH$_2$Cl$_2$)

$^1$H-NMR (300 MHz, CDCl$_3$): d=2.35 (m, 2H), 3.5 (m, 3H), 3.63 (dd, 1H), 4.16 (s, 2H), 5.68 (m, 1H), 6.42 (d, 2H), 6.61 (d, 1H), 6.97 (s, 1H), 7.53 (dd, 1H), 8.11 (d, 1H), 8.20 (d, 2H), 8.78 (s, 1H).

MS (ESP+): m/e 371 (M+H)+.

The precursor 2-chloro-5-(4-thiazolyl)methylthiopyridine was prepared in one step from 2-chloro-5-thiocyanopyridine as follows:

2-chloro-5-(4-thiazolyl)methylthiopyridine

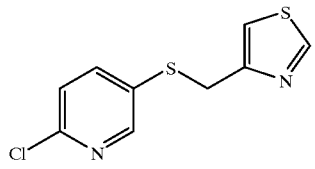

Scale: 96.5 mg, 0.566 mmol

Method: 2-chloro-5-thiocyanopyridine (96.5 mg, 0.566 mmol), 4-chloromethyithiazole hydrochloride (96.2 mg, 0.566 mmol) and potassium hydroxide (79.3 mg, 1.41 mmol) were suspended in 1:1 THF/water (5 ml), The resulting mixture was heated to 85° C. for 90 minutes and allowed to cool. The mixture was extracted with Et$_2$O (3×10 ml) and the combined extracts were dried (MgSO$_4$) and concentrated in vacuo giving a colourless oil which was used directly in the next step.

Yield=125 mg (91%)

EXAMPLES 106/107

(3R)-1-(4-pyridyl)-3-(5-cyano-2-pyridyloxy) pyrrolidine

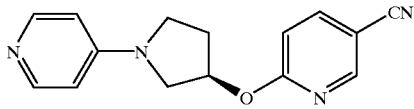

Scale: 492 mg, 3.0 mmol

Method B (without tetrabutylammonium bromide) in THF (0.6M), using (R)-1-(4-pyridyl)-3-hydroxypyrrolidine and 2-chloro-5-cyanopyridine, with 5 hr reaction time. After evaporation of the solvent, the residue was purified by column chromatography, eluting sequentially with CH$_2$Cl$_2$; 5%MeOH/CH$_2$Cl$_2$; 10%MeOH/CH$_2$Cl$_2$: 10%MeOH/1%NH$_4$OH/CH$_2$Cl$_2$ giving an off-white solid.

Yield=255 mg (32%)

R$_f$=0.36 (10%MeOH/1%NH$_4$OH/CH$_2$Cl$_2$)

$^1$H-NMR (300 MHz, CDCl$_3$): δ=2.4 (m, 2H), 3.58 (m, 3H), 3.78 (dd, 1H), 5.80 (m, 1H), 6.42 (d, 2H), 6.80 (d, 1H), 7.80 (dd, 1H), 8.22 (d, 2H), 8.50 (s, 1H).

MS (ESP+): m/e 267 (M+H)$^+$.

The (S) enantiomer was also prepared by the same method in 30% yield from the (S) alcohol, and gave identical analytical data.

EXAMPLES 108/109

(3S)-1-(4-pyridyl)-3-(5-isobutyloxycarbonyl-2-pyridyloxy)pyrrolidine

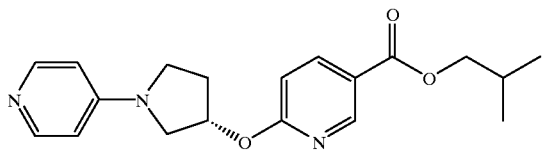

Scale: 0.78 mmol

Method D, using (S)-1-(4-pyridyl)-3-hydroxypyrrolidine and isobutyl 2-chloronicotinate. The residue was purified by column chromatography, eluting sequentially with CH$_2$Cl$_2$; 5%MeOH/CH$_2$Cl$_2$; 10%MeOH/CH$_2$Cl$_2$; 10MeOH/1%NH$_4$OH/CH$_2$Cl$_2$giving a brown oil.

Yield=178 mg (67%)

R$_f$=0.36 (10%MeOH/1%NH$_4$OH/CH$_2$Cl$_2$)

$^1$H-NMR (300 MHz, CDCl$_3$): δ=1.02 (d, 6H) 2.05 (m, 1H), 2.38 (m, 2H), 3.55 (m, 3H), 3.76 (dd, 1H), 4.10 (d, 2H), 5.80 (m, 1H), 6.41 (m, 2H), 6.75 (d, 1H), 8.20 (m, 3H), 8.83 (d, 1H).

MS (ESP+): m/e 342 (M+H)$^+$.

The (R) enantiomer was also prepared by the same method in 30% yield from the (S) alcohol, and gave identical analytical data.

EXAMPLE 110

1-(4-pyridyl-3-(5-trifluoromethyl-2-pyridylthio) pyrrolidine

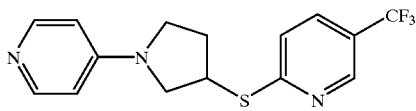

Scale: 250 mg, 1.52 mmol

Method E, using 1-(4-pyridyl)-3-hydroxypyrrolidine and 2-mercapto-5-trifluoromethylpyridine. The solvent was evaporated and the residue columned on silica, eluting sequentially with CH$_2$Cl$_2$;Et$_2$O;10%MeOH/1%NH$_4$OH/CH$_2$Cl$_2$, giving a brown oil.

Yield=201 mg (40%)

R$_f$=0.30 (10%MeOH/1%NH$_4$OH/CH$_2$Cl$_2$)

$^1$H-NMR (300 MHz, CDCl$_3$): d=2.20 (m, 1H), 2.60 (m, 1H), 3.39 (dd, 1H), 3.52 (m, 2H), 3.98 (dd, 1H), 4.59 (m, 1H), 6.40 (d, 2H), 7.27 (d, 1H), 7.66 (d, 1H), 8.22 (d, 2H), 8.69 (s, 1H).

$^{13}$C-NMR (400 MHz, CDCl$_3$): d=31.2. 41.3, 46.1, 53.4, 107.0, 121.8, 132.7, 146.3, 148.6, 151.7, 163.2. 3 quarternaries missing.

MS (ESP+): m/e 326 (M+H)$^+$.

EXAMPLE 111

(3S)-1-(4-pyridyl)-3-(3.5-dichloro-2-pyridyloxy) pyrrolidine

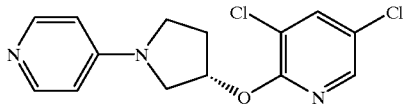

Scale: 0.91 mmol

Method D in THF without n-butylammonium bromide, using (S)-1-(4-pyridyl)-3-hydroxypyrrolidine and 2,3,5-trichloropyridine. The residue was purified by column chromatography, eluting sequentially with CH$_2$Cl$_2$; 5%MeOH/CH$_2$Cl$_2$; 10%MeOH/CH$_,2$Cl$_2$; 10%MeOH/1%NH$_4$OH/CH$_2$Cl$_2$ giving a brown oil.

Yield=283 mg (quantitative)

R$_f$=0.22 (10%MeOH/1%NH$_4$OH/CH$_2$Cl$_2$)

$^1$H-NMR (300 MHz, CDCl$_3$): δ=2.38 (m, 2H), 3.55 (m, 3H), 3.78 (dd, 1H), 5.68 (m, 1H), 6.41 (d, 2H), 7.63 (m, 1H), 8.02 (s, 1H), 8.22 (d, 2H).

MS (ESP+): m/e 310 (M+H)$^+$.

EXAMPLE 112

1-(4-pyridyl)-3-(4-(bromo)phenylthio)pyrrolidine

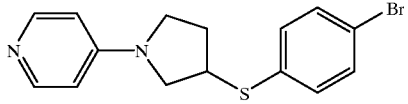

Scale: 0.84 mmol

Method G, using 4-bromothiophenol. The residue was purified by column chromatography, eluting sequentially with CH$_2$Cl$_2$; 5%MeOH/CH$_2$C$_2$; 10%MeOH/CH$_2$Cl$_2$ giving a colourless solid.

Yield=175 mg (62%)

R$_f$ 0.32 (10%MeOH/CH$_2$Cl$_2$)
$^1$H-NMR (300 MHz CDCl$_3$): δ=2.08 (m, 1H), 2.40 (m, 1H), 3.30 (m, 1H), 3.39 (m, 1H), 3.52 (m, 1H), 3.68 (m, 1H), 3.90 (m, 1H), 6.36 (d, 2H), 7.28 (d, 2H) 7.28 (d, 2H), 7.44 (d, 2H), 8.22 (d, 2H).
MS (ESP+): m/e 335/337 (M+H)$^+$.

EXAMPLE 113

1-(4-pyridyl)-3-(4-(trifluoromethyloxy)phenylthio)pyrrolidine

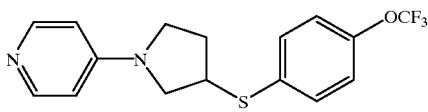

Scale: 0.84 mmol
Method G, using 4-(trifluoromethyloxy)thiophenol, The residue was purified by column chromatography, eluting sequentially with CH$_2$Cl$_2$; 5%MeOH/CH$_2$Cl$_2$; 10%MeOH/CH$_2$Cl$_2$ giving an off-white solid.
Yield=165 mg (58%)
R$_f$=0.32 (10%MeOH/CH$_2$Cl$_2$)
$^1$H-NMR (300 MHz, CDCl$_3$): δ=2.10 (m, 1H), 2.42 (m, 1H), 3.32 (m, 1H), 3.41 (m, 1H), 3.54 (m, 1H), 3.72 (m, 1H), 3.92 (m, 1H), 6.35 (d, 2H), 7.18 (d, 7.45 (d, 2H) 8.22 (d, 2H).
MS (ESP+): m/e 341 (M+H)$^+$.

EXAMPLE 114

1-(4-pyridyl)-3-((4-phenyl)phenyloxy)pyrrolidine

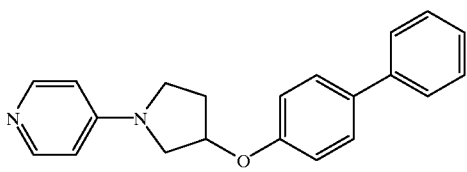

Scale: 1.83 mmol
Method E. using 4-phenylphenol. The residue was purified by column chromatography, eluting sequentially with CH$_2$Cl$_2$; 5%MeOH/CH$_2$Cl$_2$; 10%MeOH/CH$_2$Cl$_2$; 10%MeOH/1%NH$_4$OH/CH$_2$Cl$_2$ giving a white solid.
Yield=169 mg (29%)
R$_f$=0.40 (10%MeOH/1%NH$_4$OH/CH$_2$Cl$_2$)
$^1$H-NMR (300 MHz, CDCl$_3$): δ=2.35 (m, 1H), 2.55 (m, 3H), 3.58 (m, 3H), 3.76 (dd, 1H), 5.15 (m, 1H), 6.43 (m, 2H), 6.98 (d, 2H), 7.32 (dd, 1H), 7.42 (t, 2H), 7.55 (m, 4H), 8.21 (d, 2H).
MS (ESP+): m/e 317 (M+H)$^-$.

EXAMPLE 115

(R)-1-4-pyridyl-3-(5-trifluoromethyl-2-pyridylthio)pyrrolidine

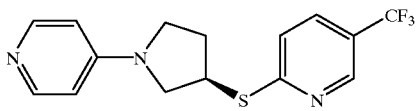

Scale: 400 mg, 2.43 mmol
Method E, using (S)-1-(4-pyridyl)-3-hydroxypyrrolidine and 2-mercapto-5-trifluoromethylpyridine. The solvent was evaporated and the residue columned on silica, eluting sequentially with CH$_2$Cl$_2$;Et$_2$O;10%MeOH/1%NH$_4$OH/CH$_2$Cl$_2$, giving a brown oil.
Yield=681 mg (86%)
R$_f$=0.30 (10%MeOH/1%NH$_4$OH/CH$_2$Cl$_2$)
$^1$H-NMR (300 MHz, CDCl$_3$): d=2.20 (m, 1H), 2.60 (m, 1H), 3.39 (dd, 1H), 3.52 (m, 2H), 3.98 (dd, 1H), 4.59 (m, 1H), 6.40 (d, 2H), 7.27 (d, 1H), 7.66 (d, 1H), 8.22 (d, 2H), 8.69 (s, 1H).
MS (ESP+): m/e 326 (M+H)$^+$.

EXAMPLE 116

(S)-(-1-(4-pyridyl)-3-(5-trifluoromethyl-2-pyridylthio)pyrrolidine

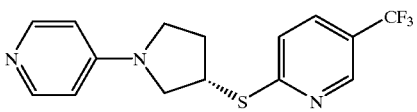

Scale: 400 mg, 2.43 mmol
Method E, using (R)-1-(4-pyridyl)-3-hydroxypyrrolidine and 2-mercapto-5-trifluoromethylpyridine. The solvent was evaporated and the residue columned on silica, eluting sequentially with CH$_2$Cl$_2$;Et$_2$O;10%MeOH/1%NH$_4$OH/CH$_2$Cl$_2$, giving a brown oil.
Yield=663 mg (83%)
R$_f$=0.30 (10%MeOH/1%NH$_4$OH/CH$_2$Cl$_2$)
$^1$H-NMR (300 MHz, CDCl$_3$): d=2.20 (m, 1H), 2.60 (m, 1H), 3.39 (dd, 1H), 3.52 (m, 2H), 3.98 (dd, 1H), 4.59 (m, 1H), 6.40 (d, 2H), 7.27 (d, 1H), 7.66 (d, 1H), 8.22 (d, 2H), 8.69 (s, 1H).
MS (ESP+): m/e 326 (M+H)$^+$.

EXAMPLE 117

1-(3-fluoro-4-pyridyl)-3-(5-trifluoromethyl-2-pyridyloxy)pyrrolidine

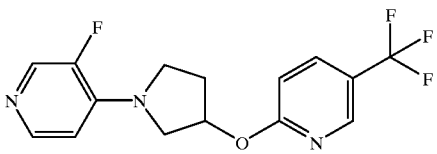

Scale: 1.5 mmol
Method E, using 1-(3-fluoro-4-pyridyl)-3-hydroxypyrrolidine and 2-hydroxy-5-trifluoromethylpyridine. The product was isolated as a pale yellow gum.
Yield=105 mg (22%)
R$_f$=0.20 (EtOAc)
$^1$H-NMR (200 MHz, CDCl$_3$): δ=2.30 (m, 2H), 3.70 (m, 3H), 3.95 (m, 1H), 5.76 (m, 1H), 6.22 (m 1H), 6.80 (d, 1H), 7.78 (dd, 1H), 8.04 (d, 1H), 8.12 (d, 1H), 8.42 (s, 1H).
MS (ESP+): m/e 328 (M+H)$^+$.

1-(3-Fluoro-4-pyridyl)-3-hydroxypyrrolidine was generated in four steps from 1-(4-pyridyl) 3-hydroxypyrrolidine as follows:

1-(4-Pyridyl)-3-(t-butyldimethylsilyloxy)pyrrolidine 1-(4-Pyridyl)-3-hydroxypyrrolidine (5.02 g, 30.6 mmol) was dissolved in DMF (40 ml) and imidazole (9.18 g, 135 mmol) was added. followed by a solution of t-butylchlorodimethylsilane (10.20 g. 67.7 mmol) in DMF (25 ml), After stirring overnight the mixture was partitioned between water and dichloromethane. The organic layer was dried over sodium sulphate. After evaporation of the solvents, the residue was purified by column chromatography on alumina, eluting sequentially with CH$_2$Cl$_2$;EtOAc; 10%MeOH/EtOAc; 50%MeOH/EtOAc giving a clear yellow oil.

Yield=quantitative

R$_f$=0.38 (10%MeOH/1%NH$_4$OH/CH$_2$Cl$_2$)

$^1$H-NMR (200 MHz, CDCl$_3$): δ=0.01 (d, 6H), 0.80 (s, 9H), 1.95 (m, 2H), 3.07 (dd, 1H), 3.25 (m, 1H), 3.38 (m, 2H), 4.44 (m, 1H), 6.24 (d, 2H), 8.11 (d, 2H).

1-(3-Bromo-4-pyridyl)-3-(t-butyldimethylsilyloxy) pyrrolidine 1-(4-Pyridyl)-3-(t-butyldimethylsilyloxy)pyrrolidine (8.92 g, 32.1 mmol) was dissolved in acetonitrile (140 ml) and N-bromosuccinimide (6.00 g, 33.7 mmol) was added portionwise. After stirring overnight the solvent was removed under reduced pressure and the residue partitioned between dichloromethane and water. The organic layer was dried over sodium sulphate. After evaporation of the solvent, the residue was purified by column chromatography on silica gel, eluting sequentially with CH$_2$Cl$_2$; 5%MeOH CH$_2$Cl$_2$; 10%MeOH/CH$_2$Cl$_2$. Further purification by column chromatography on alumina, eluting sequentially with isohexane; 25%EtOAc/isohexane gave the product as a colourless oil.

Yield=3.44 g (30%)

R$_f$=0.70 (10%MeOH/1%NH$_4$OH/CH$_2$Cl$_2$)

$^1$H-NMR (200 MHz, CDCl$_3$): δ=0.0 (d, 6H), 0.80 (s, 9H), 1.90 (m, 2H), 3.38 (dd, 1H), 3.48 (m, 1H), 3.62 (m, 1H), 3.80 (dd, 1H), 4.40 (m, 1H), 6.40 (d, 1H), 8.02 (d, 1H), 8.30 (s, 1H).

MS (ESP+): m/e 357/359 (M+H)$^+$.

1-(3-Fluoro-4-pyridyl)-3-(t-butyldimethylsilyloxy) pyrrolidine

A solution of 1-(3-bromo-4-pyridyl)-3-(t-butyldimethylsilyloxy)pyrrolidine (1.07 g, 3.0 mmol) in THF (10 ml) was added to a solution of t-butyl lithium (1.5M in hexanes, 4.2 ml) in THF (10 ml) at −78° C. After ten minutes a solution of N-fluorobisbenzenesulphonide (1.42 g, 4.5 mmol) in THF (10 ml) was added dropwise. After a further hour at −78° C. the mixture was allowed to *vark to room temperature. After stirring overnight the mixture was partitioned between dichloromethane and water. The organic layer was dried over sodium sulphate.

After evaporation of the solvent, the residue was purified by column chromatography on alumina, eluting sequentially with isohexane; 25%EtOAc/isohexane; 60%EtOAc/isohexane giving a pale yellow solid.

Yield=0.47 g (53%)

R$_f$=0.39 (7%MeOH/CH$_2$Cl$_2$)

$^1$H-NMR (200 MHz, CDCl$_3$): δ=0.0 (d, 6H), 0.80 (s, 9H), 1.90 (m, 2H), 3.26 (dm, 1H), 3.55 (m, 3H), 4.41 (m, 1H), 6.34 (m, 1H), 7.92 (d, 1H), 8.02 (d, 1H).

MS (ESP+): m/e 297 (M+H)$^+$.

1-(3-Fluoro-4-pyridyl)-3-hydroxypyrrolidine 1-(3-Fluoro-4-pyridyl)-3-(t-butyldimethylsilyloxy) pyrrolidine (0.45 g, 1.52 mmol) was dissolved in acetonitrile (10 ml) and 1M HCl (aq) (2 ml) was added. After stirring overnight solid potassium carbonate was added to render the solution alkaline. After standing at −15° C. for several days the white solid formed was isolated by filtration through a pad of alumina. The pad was washed well with a mixture of methanol and dichloromethane and product-containing fractions were concentrated under vacuum to give a white solid.

Yield=0.28 g (ca. quantitative)

R$_f$=0.1 (10%MeOH/CH$_2$Cl$_2$)

$^1$H-NMR (200 MHz, d$_6$-DMSO): δ=1.90 (m, 2H), 3.30 (dm, 1H), 3.55 (m, 3H), 4.35 (m, 1H), 6.58 (m, 1H), 7.94 (d, 1H), 8.06 (d, 1H).

MS (ESP+): m/e 183 (M+H)$^+$.

EXAMPLES 118/119

(S)-1-(4-pyridyl)-3-(3,4-dichlorophenyloxy) pyrrolidine

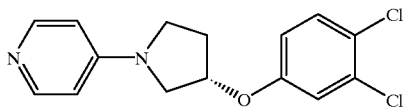

Scale: 0.94 mmol

Method G, using 3-methyl-4-(methylthio)phenol. The residue was purified by column chromatography, eluting sequentially with CH$_2$Cl$_2$; 5%MeOH/CH$_2$Cl$_2$; 10%MeOH/CH$_2$Cl$_2$; 10%MeOH/1%NH$_4$OH/CH$_2$Cl$_2$.

Yield=164 mg (56%)

$^1$H-NMR (300 MHz, CDCl$_3$): δ=2.30 (m, 2H), 3.52 (m, 3H), 3.65 (m, 1H), 5.02 (m, 1H), 6.40 (d, 2H), 6.74 (dd, 1H), 6.98 (m, 1H), 7.35 (d, 1H), 8.22 (d, 2H).

MS (ESP+): m/e 309/311/313 (M+H)$^+$.

The (R) enantiomer was also prepared by the same method, and gave identical analytical data.

EXAMPLES 120/121

1-(4-pyridyl )-3-(4-(methylthio)phenyloxy)pyrrolidine

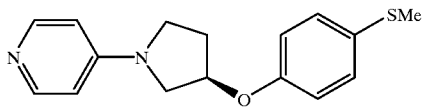

Scale: 0.94 mmol

Method G, using 4-(methylthio)phenol. The residue was purified by column chromatography, eluting sequentially with CH$_2$Cl$_2$; 5%MeOH/CH$_2$Cl$_2$; 10%MeOH/CH$_2$Cl$_2$; 10%MeOH/1%NH$_4$OH/CH$_2$Cl$_2$.

Yield=131 mg(49%)

$^1$H-NMR (300 MHz, CDCl$_3$): δ=2.15 (m, 1H), 2.38 (m, 1H), 3.52 (m, 3H), 3.65 (m, 1H), 5.05 (m, 1H), 6.42 (d, 2H), 6.82 (d, 2H), 7.28 (d, 2H), 8.22 (d, 2H).

MS (ESP+): m/e 287 (M+H)$^+$.

The (S) enantiomer was also prepared by the same method, and gave identical analytical data.

EXAMPLES 122/123

1-(4-pyridyl)-3-(4-(trifluoromethyl)phenyloxy)pyrrolidine

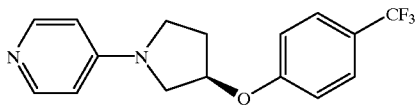

Scale: 0.94 mmol

Method G, using 4-trifluoromethylphenol. The residue was purified by column chromatography, eluting sequentially with $CH_2Cl_2$; 5%MeOH/$CH_2Cl_2$; 10%MeOH/$CH_2Cl_2$; 10%MeOH/1%$NH_4OH$/$CH_2Cl_2$.

Yield=124 mg (43%)

$^1$H-NMR (300 MHz, $CDCl_3$): δ=2.35 (m, 2H), 3.54 (m, 2H), 3.72 (m, 1H), 5.12 (m, 1H), 6.40 (d, 2H), 6.95 (d, 2H), 7.66 (d, 2H), 8.22 (d, 2H).

MS (ESP+): m/e 309 (M+H)$^+$.

The (S) enantiomer was also prepared by the same method, and gave identical analytical data.

EXAMPLES 124/125

(R)-1-(4-pyridyl)-3-(3-methyl-4-(methylthio)phenyloxy)pyrrolidine

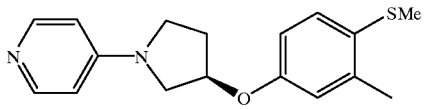

Scale: 0.94 mmol

Method G, using 3-methyl-4-(methylthio)phenol. The residue was purified by column chromatography, eluting sequentially with $CH_2Cl_2$; 5%MeOH/$CH_2Cl_2$; 10%MeOH/$CH_2Cl_2$; 10%MeOH/1%$NH_4OH$/$CH_2Cl_2$.

Yield=77 mg (27%)

$^1$H-NMR (300 MHz, $CDCl_3$): δ=2.25 (m, 2H), 2.36 (s, 3H), 2.42 (s, 3H), 3.54 (m, 3H), 3.72 (m, 1H), 5.04 (m, 1H), 6.40 (d, 2H), 6.70 (m, 2H), 7.18 (m, 1H), 8.22 (d, 2H).

MS (ESP+): m/e 301 (M+H)$^+$.

The (S) enantiomer was also prepared by the same method, and gave identical analytical data.

EXAMPLE 126

(3R)-1-(4-pyridyl)-3-(4-ethylphenoxy)pyrrolidine

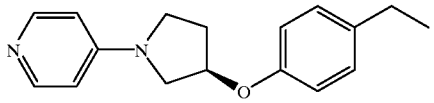

Scale: 0.94 mmol

Method G, using (S)-1-(4-pyridyl)-3-(p-toluenesolphonyloxy)pyrrolidine and 4-ethylphenol. The residue was purified by column chromatography, eluting sequentially with $CH_2Cl_2$; 5%MeOH/$CH_2Cl_2$; 10%MeOH/$CH_2Cl_2$; 10%MeOH/1%$NH_4OH$/$CH_2Cl_2$ giving a light brown solid.

Yield=132 mg (53%)

$R_f$=0.4 (10%MeOH/1%$NH_4OH$/$CH_2Cl_2$)

$^1$H-NMR (200 MHz, $CDCl_3$): δ=1.22 (t, 3H), 2.25 (m, 1H), 2.38 (m, 1H), 2.60 (q, 2H), 3.55 (m, 3H), 3.65 (dd, 1H), 5.04 (m, 1H), 6.40 (m, 2H), 6.80 (d, 2H), 7.14 (d, 2H), 8.21 (d, 2H).

MS (ESP+): m/e 269 (M+H)$^+$.

EXAMPLE 127

1-(6-methyl-4-pyrimidyl)-3-(5-trifluoromethyl-2-pyridyloxy)pyrrolidine

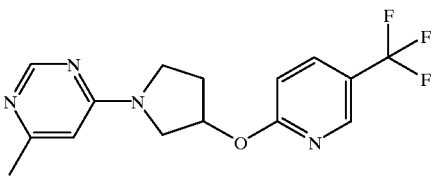

Scale: 1.5 mmol

6-Methyl-4-chloropyrimidine (0.46 mmol) (for preparation, see Chem. Pharm. Bull., (1976), 24, 303) and 3-(5-trifluoromethyl-2-pyridyloxy)pyrrolidine (348 mg, 1.5 mmol) were heated with sodium bicarbonate (330 mg, 3.9 mmol) in ethanol (8 ml) at reflux overnight. The mixture was partitioned between diethyl ether and dilute aqueous Hcl. The aqueous phase was made strongly alkaline with sodium hydroxide and reextracted with dichloromethane. The latter extracts were dried over sodium sulphate. After evaporation of the solvents, the residue was purified by column chromatography, eluting sequentially with $CH_2Cl_2$; 5%MeOH/$CH_2Cl_2$; 5%MeOH/1%$NH_4OH$/$CH_2Cl_2$ giving a light brown gum.

Yield=150 mg (ca quantitative)

$R_f$=0.28 (5%MeOH/$CH_2Cl_2$)

$^1$H-NMR (200 MHz, $CDCl_3$): δ=2.38 (m, 5H), 3.75 (m, 4H), 5.78 (m, 1H), 6.18 (s, 1H), 6.80 (d, 1H), 7.78 (dd, 1H), 8.42 (s, 1H), 8.50 (s, 1H).

MS (ESP+): m/e 325 (M+H)$^+$.

EXAMPLE 128

(3R)-1-(4-pyridyl)-3-(3-bromo-5-trifluoromethyl-2-pyridyloxy)pyrrolidine

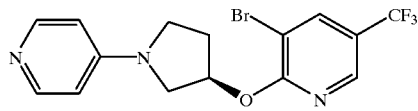

Scale: 11.5 mmol

Method E, using (R)-1-(4-pyridyl)-3-hydroxypyrrolidine and 3-bromo-5-trifluoromethyl-(2H)-pyridone. The residue was purified by column chromatography, eluting sequentially with $CH_2Cl_2$; 5%MeOH/$CH_2Cl_2$; 10%MeOH/$CH_2Cl_2$ giving an off-white solid.

Yield=80 mg (13%)

$R_f$=0.28 (10%MeOH/1%$NH_4OH$/$CH_2Cl_2$)

$^1$H-NMR (300 MHz, $CDCl_3$): δ=2.40 (m, 2H), 3.55 (m, 3H), 3.80 (dd, 1H), 5.78 (m, 1H), 6.40 (d, 2H), 8.02 (m, 1H), 8.22 (d, 2H), 8.38 (m, 1H).

MS (ESP+): m/e 388/390 (M+H)$^+$.

EXAMPLE 129

1-(4-pyridyl)-3-(4-(5-bromo-2-thiophenylmethylamino)phenoxy)pyrrolidine

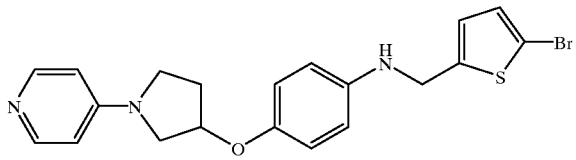

Scale: 1.57 mmol 1-(4-pyridyl)-3-(4-aminophenoxy)pyrrolidine (made from 1-(4-pyridyl)-3-hydroxypyrrolidine by alkylation with 4-fluoronitrobenzene followed by hydrogenation) (400 mg, 1 eq) and 5-bromothiophenecarboxaldehyde (330 mg, 1.1 eq) were dissolved in methanol (8ml) and cooled in ice-water. The mixture was acidified to pH4 with glacial acetic acid. Sodium cyanoborohydride (103 mg, 1.05 eq) was added portionwise. The reaction mixture was allowed to warm to room temperature and stirred for 2 hours before partitioning between $CH_2Cl_2$ and 10% aqueous sodium carbonate solution.

The organic layer was washed with water and brine, dried over magnesium sulphate and concentrated. The residue was purified by column chromatography, eluting sequentially with $CH_2Cl_2$; 2%MeOH/$CH_2Cl_2$; 4%MeOH/$CH_2Cl_2$; 5%MeOH/0.5%$NH_4OH$/$CH_2Cl_2$ giving a light brown solid.

Yield=341 mg (50%)
$R_f$=0.45 (10%MeOH/1%$NH_4OH$/$CH_2Cl_2$)
$^1$H-NMR (300 MHz, $CDCl_3$): δ=2.22 (m, 1H), 2.38 (m, 1H), 3.5 (m, 4H), 4.40 (s, 2H), 4.98 (m, 1H), 6.41 (m, 2H), 6.62 (m, 2H), 6.78 (m, 3H), 6.90 (s, 1H), 8.21 (d, 2H).
MS (ESP+): m/e 430/432 (M+H)$^+$.

EXAMPLE 130

1-(4-pyridyl)-4-(3-chloro-5-trifluoromethyl-2-pyridyl)piperazine

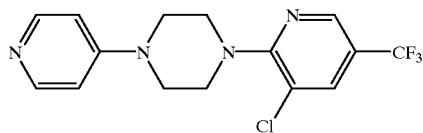

Scale: 3.07 mmol

Method: 1-Pyridyl piperazine (500 mg) was heated at reflux in THF (10 ml) with 2,3-dichloro-5-trifluoromethylpyridine (662 mg, 1 eq) and triethylamine (0.470 ml, 1.1 eq) for 18 hours. The mixture was partitioned between dichloromethane and water. The organic layer was dried over sodium sulphate. After evaporation of the solvent, the residue was purified by column chromatography on silica gel, eluting sequentially with $CH_2Cl_2$; 3%MeOH/$CH_2Cl_2$; 6%MeOH/$CH_2Cl_2$, giving the product as a yellow solid.

Yield=602 mg (57%)
$R_f$=0.45 (10%MeOH/1%$NH_4OH$/$CH_2Cl_2$)
$^1$H-NMR (250 MHz, $CDCl_3$): δ=3.5 (m, 4H), 3.68 (m, 4H), 6.72 (dm, 2H), 7.80 (d, 1H), 8.32 (dm, 2H), 8.42 (m, 1H).
MS (CI): m/e 343 (M+H)$^+$.

EXAMPLES 131/132

(3R)-1-(4-pyridyl)-3-(6-chlorobenzthiazol-2-yloxyy)pyrrolidine

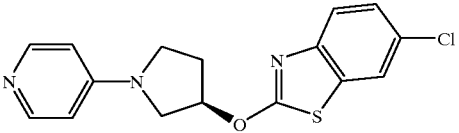

Scale: 1.82 mmol

Method A, using (R)-1-(4-pyridyl)-3-hydroxypyrrolidine and 2,6-dichlorobenzthiazole. The residue was purified by column chromatography, eluting sequentially with $CH_2Cl_2$; EtOAc; 5%MeOH/$CH_2Cl_2$; 10%MeOH/$CH_2Cl_2$: 10%MeOH/1%$NH_4OH$/$CH_2Cl_2$ giving a brown solid which was triturated with ether.

Yield=215 mg (36%)
$R_f$=0.38 (10%MeOH/1%$NH_4OH$/$CH_2Cl_2$)
$^1$H-NMR (200 MHz, $CDCl_3$): δ=2.40 (m, 1H), 2.54 (m, 1H), 3.58 (m, 2H), 3.78 (m, 2H), 5.87 (m, 1H), 6.44 (d, 2H), 7.36 (dd, 1H), 7.62 (m, 2H), 8.23 (d, 2H).
MS (ESP+): m/e 332 (M+H)$^+$.

The (R) enantiomer was also prepared by the same method, and gave identical analytical data.

EXAMPLE 133

(3R)-1-(4-pyridyl)-3-(2-quinolyloxy)pyrrolidine

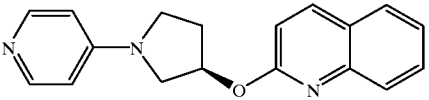

Scale: 1.83 mmol

Method A, using (R)-1-(4-pyridyl)-3-hydroxypyrrolidine and 2-chloroquinoline in 1 ml THF. The residue was purified by column chromatography, eluting sequentially with $CH_2Cl_2$; 5%MeOH/$CH_2Cl_2$; 10%MeOH/$CH_2Cl_2$; 10%MeOH/1%$NH_4OH$/$CH_2Cl_2$ giving an off-white solid.

Yield=500 mg (94%)
$R_f$=0.37 (10%MeOH/1%$NH_4OH$/$CH_2Cl_2$)
$^1$H-NMR (300 MHz, $CDCl_3$): δ=2.42 (m, 2H), 3.58 (m, 3H), 3.82 (dd, 1H), 5.96 (m, 1H), 6.42 (d, 2H), 6.84 (d, 1H), 7.40 (t, 1H), 7.63 (t, 1H), 7.72 (d, 1H), 7.98 (d, 11H), 8.20 (d, 2H).
MS (ESP+): m/e 292 (M+H)$^+$.

EXAMPLES 134/135

(3R)-1-(4-pyridyl-3-(5-chlorobenzoxazol-2-yloxy)pyrrolidine

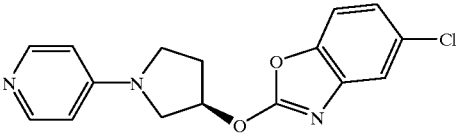

Scale: 175 mg, 1.07 mmol

Method A (without tetrabutylammonium bromide) in THF (0.5M), using (R)-1-(4-pyridyl)-3-hydroxypyrrolidine and 2,6-dichlorobenzoxazole, with 1 hr reaction time. After evaporation of the solvent, the residue was purified by column chromatography, eluting sequentially with CH₂Cl₂; 5%MeOH/CH₂Cl₂; 10%MeOH/CH₂Cl₂; 10%MeOH/1%NH₄OH/CH₂Cl₂ giving an off-white powder.

Yield=79 mg (23%)

R$_f$=0.54 (10%MeOH/1%NH₄OH/CH₂Cl₂)

¹H-NMR (300 MHz, CDCl₃): δ=2.42 (m, 1H), 2.58 (m, 1H), 3.61 (m, 2H), 3.78 (m, 2H), 5.75 (m, 1H), 6.42 (d, 2H), 7.18 (dd, 1H), 7.25 (m, 1H), 7.47 (s, 1H), 8.22 (d, 2H).

MS (ESP+): m/e 316/318 (M+H)⁺.

The (S) enantiomer was also prepared by the same method in 46% yield from the (S) alcohol, and gave identical analytical data.

EXAMPLE 136

(3R)-1-(4-pyridyl)-3-(6-chlorobenzoxazol-2-yloxy)pyrrolidine

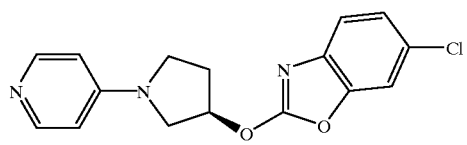

Scale: 1.27 mmol

Method A, using (R)-1-(4-pyridyl)-3-hydroxypyrrolidine and 2,6-dichlorobenzoxazole in 1 ml THF. The residue was purified by column chromatography, eluting sequentially with CH₂Cl₂; 5%MeOH/CH₂Cl₂; 10%MeOH/CH₂Cl₂; 10%MeOH/1%NH₄OH/CH₂Cl₂ giving an off-white solid.

Yield=25 mg (6%)

R$_f$=0.46 (10%MeOH/1%NH₄OH/CH₂Cl₂)

¹H-NMR (300 MHz, CDCl₃): δ=2.42 (m, 1H), 2.60 (m, 1H), 3.60 (m, 2H), 3.80 (m, 2H), 5.75 (m, 1H), 6.42 (d, 2H), 7.25 (m, 1H+CHCl₃), 7.40 (m, 2H), 8.22 (m, 2H).

MS (ESP+): m/e 316/318 (M+H)⁺.

EXAMPLE 137

(3R)-1-(4-pyridyl)-3-(5-trifluoromethylbenzthiazol-2-yloxy)pyrrolidine

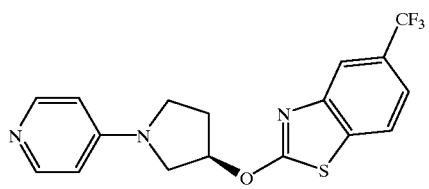

Scale: 2.44 mmol

Method A, using (R)-1-(4-pyridyl)-3-hydroxypyrrolidine and 2-(methanesulphinyl)-5-trifluoromethylbenzthiazole. The residue was purified by column chromatography, eluting sequentially with CH₂Cl₂; EtOAc; 5%MeOH/CH₂Cl₂; 10%MeOH/CH₂Cl₂; 10%MeOH/1%NH₄OH/CH₂Cl₂ giving a pale yellow solid.

Yield=185 mg (21%)

R$_f$=0.37 (10%MeOH/1%NH₄OH/CH₂Cl₂)

¹H-NMR (300 MHz, CDCl₃): δ=2.41 (m, 1H), 2.58 (m, 1H), 3.58 (m, 2H), 3.78 (m, 2H), 5.88 (m, 1H), 6.42 (d, 2H), 7.48 (d, 1H), 7.77 (d, 1H), 7.88 (s, 1H), 8.22 (d, 2H).

MS (ESP+): m/e 366 (M+H)⁺.

EXAMPLE 138

(3R)-1-(4-pyridyl)-3-(6-bromothiazolo[4,5-b]pyridin-2-yloxy)pyrrolidine

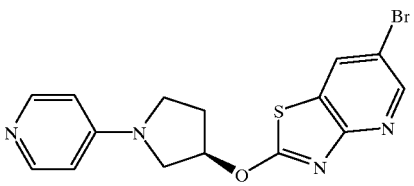

Scale: 355 mg, 2.17 mmol

Method B, using (R)-1-(4-pyridyl)-3-hydroxypyrrolidine and 2-methanesulphonyl-4-aza-6-bromobenzthiazole, with 1 hr reaction time. After evaporation of the solvent, the residue was purified by column chromatography, eluting sequentially with CH₂Cl₂; 5%MeOH/CH₂Cl₂; 10%MeOH/CH₂Cl₂; 10%MeOH/1%NH₄OH/CH₂Cl₂ giving a pale yellow solid.

Yield=128 mg (16%)

R$_f$=0.47 (10%MeOH/1%NH₄OH/CH₂Cl₂)

¹H-NMR (300 MHz, CDCl₃): δ=2.42 (m, 1H), 2.60 (m, 1H), 3.60 (m, 2H), 3.80 (m, 2H), 5.98 (m, 1H), 6.42 (d, 2H), 8.11 (s, 1H), 8.22 (d, 2H), 8.58 (s, 1H).

MS (ESP+): m/e 377/379 (M+H)⁺.

2-Methanesulphonyl-4-aza-6-bromobenzthiazole was made in three steps from 2-amino-3,5-dibromopyridine as follows:

2-Thio-4-aza-6-bromobenzthiazole

2-Amino-3,5-dibromopyridine (5.21 g, 20.7 mmol) and ethyl potassium xanthate (6.28 g, 41.3 mmol) were heated together in N-methylpyrrolidine (42 ml) at 170° C. for three hours. The mixture was dissolved in hot water (ca. 150 ml) and filtered whilst hot. Upon cooling, the filtrate was acidified with acetic acid. The resulting precipitate was filtered, washed with water and dried to gice the product.

Yield=4.48 g (87%)

¹H-NMR (300 MHz, d6-DMSO): δ=8.38 (s, 1H), 8.45 (s 1H).

MS (Cl+): m/e 247/249 (M+H)⁺.

2-Methylthio-4-aza-6-bromobenzthiazole

2-Thio-4-aza-6-bromobenzthiazole (4.45 g, 18.02 mmol) and potassium carbonate (2.99 g, 1.2 equivalents) were mixed in DMF (40 ml). Iodomethane (1.13 ml, 1.0 equivalents) was added dropwise. After stirring for three hours the mixture was partitioned between diethyl ether and water. The organic layer was dried over sodium sulphate, filtered and evaporated to give a dark oil. This was purified by column chromatography, eluting sequentially with CH₂Cl₂ and then diethyl ether.

Yield=1.3 g (28%)

R$_f$=0.66 (50% EtOAc/CH₂Cl₂)

¹H-NMR (300 MHz, CDCl₃): δ=2.79 (s, 3H), 8.15 (s, 1H), 8.55 (s, 1H).

MS (Cl+): m/e 261/263 (M+H)⁺.

2-Methanesulphonyl-4-aza-6-bromobenzthiazole

2-Methylthio-4-aza-6-bromobenzthiazole (1.02 g, 3.9 mmol) was dissolved in acetic acid (10 ml) and a solution of potassium permanganate (1.36 g, 2.2 equivalents) in water (10 ml) was added with sufficient cooling in ice as to keep the reaction temperature at 25–30° C. After stirring for an hour at room temperature the black reaction mixture was treated with sodium metabisulphite, giving a white suspension. The pH was adjusted to ca 8–9 with 20% aqueous ammonia. The mixture was extracted with ethyl acetate, and the combined organic phases were dried over sodium sulphate, filtered and evaporated to give an orange-cream solid.

Yield=0.71 g (62%)

$R_f$=0.58 (50%EtOAc/CH$_2$Cl$_2$)

$^1$H-NMR (300 MHz, CDCl$_3$): δ=3.42 (s, 3H), 8.55 (s, 1H), 8.85 (s, 1H).

MS (Cl+): m/e 293/295 (M+H)$^+$.

EXAMPLES 139/140

(3R)-1-(4-pyridyl)-3-(6-bromo-2-quinoxalinyloxy) pyrrolidine

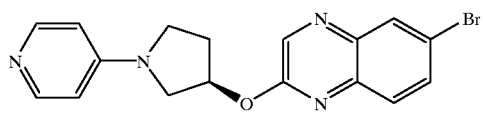

Scale: 0.63 mmol

Method B, using (R)-1-(4-pyridyl)-3-hydroxypyrrolidine and 2-chloro-6-bromoquinoxaline. The residue was purified by column chromatography, eluting sequentially with CH$_2$Cl$_2$; 5%MeOH/CH$_2$Cl$_2$; 10%MeOH/CH$_2$Cl$_2$; 10%MeOH/1%NH$_4$OH/CH$_2$Cl$_2$ giving a yellow solid.

Yield=200 mg (85%)

$R_f$=0.34 (10%MeOH/1%NH$_4$OH/CH$_2$Cl$_2$)

$^1$H-NMR (200 MHz, CDCl$_3$): δ=2.42 (m, 2H), 3.60 (m, 3H), 3.84 (dd, 1H), 5.94 (m, 1H), 6.44 (d, 2H), 7.77 (m, 2H), 8.21 (m, 3H), 8.43 (s, 1H).

MS (ESP+): m/e 371/373 (M+H)$^+$.

The (S) enantiomer was also prepared by the same method in 30% yield from the (S) alcohol, and gave identical analytical data.

EXAMPLE 141

(3R)-1-(4-pyridyl)-3-(6-fluorobenzthiazol-2-yloxy) pyrrolidine

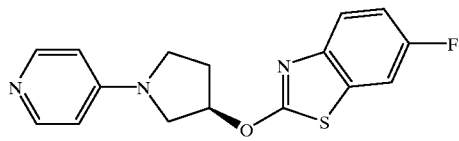

Scale: 2.44 mmol

Method B, using (R)-1-(4-pyridyl)-3-hydroxypyrrolidine and 2-(isopropylsulphonyl)-6-trifluoromethylbenzthiazole. The residue was purified by column chromatography, eluting sequentially with CH$_2$Cl$_2$: EtOAc; 5%MeOH/CH$_2$Cl$_2$; 10%MeOH/CH$_2$Cl$_2$; 10%MeOH/1%NH$_4$OH/CH$_2$Cl$_2$ giving an off-white solid.

Yield=498 mg (65%)

$R_f$=0.42 (10%MeOH/1%NH$_4$OH/CH$_2$Cl$_2$)

$^1$H-NMR (300 MHz, CDCl$_3$): δ=2.35 (m, 1H), 2.45 (m, 1H), 3.48 (m, 2H), 3.66 (m, 2H), 5.78 (m, 1H), 6.38 (d, 2H), 7.03 (m, 1H), 7.25 (m, 1H) 7.55 (m, 1H), 8.18 (d, 2H).

MS (ESP+): m/e 316 (M+H)$^+$.

EXAMPLE 142

The following compounds were also prepared using the methods described below.

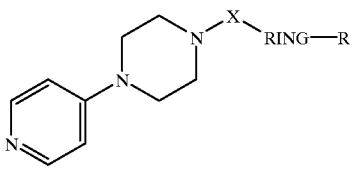

| Compound | X | Ring | R | m.p. ° C. | Method |
|---|---|---|---|---|---|
| 1 | CH$_2$ | phenyl | 4-cyanoQ | 95–98 | B |
| 2 | CH$_2$ | 2-furanyl | H | OIL* | A |
| 3 | CH$_2$ | 4-pyrimidinyl | 2,6-dichloro | >300 | B |
| 4 | CH$_2$ | 4-thiazolyl | 2-(4)-chloro-phenyl | 151–152 | B |
| 5 | CH$_2$ | 4-oxazolyl | 2-(4)-bromo-phenyl | 192–193 | B |
| 6 | CH$_2$ | phenyl | 4-methane-sulphone | 200–202 | B |
| 7 | — | phenyl | 3-nitro | 145–147 | C |
| 8 | — | phenyl | 3-methyl-4-nitro | 158–160 | C |
| 9 | — | phenyl | 3-trifluoro-methyl-4-nitro | 168–170 | C |

Method A 490 mg 4-pyridylpiperazine, 498 mg sodium acetate, and 0.38 ml 2-furaldehyde was stirred in 12 ml methanol containing 3 g 3 A$^0$ molecular sieve powder. 377 mg sodium cyanoborohydride was added and stirring continued overnight. The sieve was filtered and the filtrate concentrated and stirred with 25 ml 2 M sodium hydroxide solution. Extraction with dichloromethane and drying over MgSO$_4$, followed by evaporation and chromatography (10 g Bond Elute, CH$_2$Cl$_2$ then 1% methanol/CH$_2$Cl$_2$/1%NH$_4$OH) gave compound 2 (214 mg) as a colourless oil.

Method B 490 mg 4-pyridylpiperazine and 614 mg 4-chloromethylphenyl methyl sulphone in 1.8 ml isopropanol and 0.2 ml water with 1.4 ml triethylamine was refluxed for 1.25 hours, then stirred overnight at ambient temperature. The solvent was evaporated, the residue dissolved in dichloromethane and washed with 5% w/v sodium hydroxide solution followed by water and brine, then dried over MgSO$_4$. Evaporated then chromatographed (as in Method A above) to give compound 6 (640 mg). Compounds 1, 3, 4 and 5 were prepared in an analogous manner.

Method C 980 mg pyridylpiperazine and 1.0 g 2-methyl-4-fluoronitrobenzene with 1.8 g anhydrous potassium carbonate in 10 ml DMSO was heated at 125° C. overnight. The mixture was diluted with dichloromethane and washed with water and brine. Dried evaporated and chromatographed as above in Method A to give compound 8 (903 mg). Compounds 7 and 9 were prepared in a similar manner.

EXAMPLE 143

Illustrative pharmaceutical dosage forms suitable for presenting the compounds of the invention for therapeutic or prophylactic use include the following tablet and capsule formulations, which may be obtained by conventional procedures well known in the art of pharmacy and are suitable for therapeutic or prophylactic use in humans:

| (a) Tablet I | mg/tablet |
| --- | --- |
| Compound Z* | 1.0 |
| Lactose Ph. Eur. | 93.25 |
| Croscarmellose sodium | 4.0 |
| Maize starch paste (5% w/v aqueous paste) | 0.75 |
| Magnesium stearate | 1.0 |
| (b) Tablet II | mg/tablet |
| Compound Z* | 50 |
| Lactose Ph. Eur. | 223.75 |
| Croscarmellose sodium | 6.0 |
| Maize starch | 15.0 |
| Polyvinylpyrrolidone (5% w/v aqueous paste) | 2.25 |
| Magnesium stearate | 3.00 |
| (c) Tablet III | mg/tablet |
| Compound Z* | 100 |
| Lactose Ph. Eur. | 182.75 |
| Croscarmellose sodium | 12.0 |
| Maize starch paste (5% w/v aqueous paste) | 2.25 |
| Magnesium stearate | 3.0 |
| (d) Capsule | mg/capsule |
| Compound Z* | 10 |
| Lactose Ph. Eur. | 488.5 |
| Magnesium stearate | 1.5 |

Note
*The active ingredient Compound Z is a compound of formula I, or a salt thereof, for example a compound of formula I described in any of the preceding Examples.

The tablet compositions (a)–(c) may be enteric coated by conventional means, for example, with cellulose acetate phthalate.

What is claimed is:

1. A compound of formula I, or a pharmaceutically acceptable salt thereof,

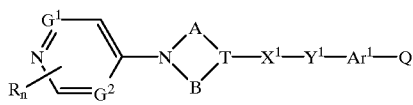

I wherein $G^1$ is CH;

$G^2$ is CH;

n is 1 or 2;

R is hydrogen, halogeno, trifluoromethyl, trifluoromethoxy, cyano, amino, hydroxy, nitro, (1–4C) alkyl, (1–4C)alkoxy, (1–4C)alkylamino, di(1–4C) alkylamino or phenyl(1–4C)alkyl;

A is methylene or ethylene; B is ethylene; and wherein A and B may independently optionally bear a substituent selected from (1–6C)alkyl, (1–6C)alkoxy, phenyl (1–4C)alkyl, halogeno and (1–6C)alkoxycarbonyl;

T is N;

$X^1$ is selected from $SO_2$, SO, CO and $CR^3R^4O$; wherein $R^3$ and $R^4$ are independently selected from hydrogen and (1–4C)alkyl;

$Y^1$ represents $CR^6R^7$, wherein $R^6$ and $R^7$ are independently selected from hydrogen and (1–4C)alkyl;

$Ar^1$ is a phenylene, naphthylene, a 5- or 6-membered monocyclic heteroaryl ring containing 1, 2 or 3 heteroatoms selected from nitrogen, oxygen and sulphur, or a 9- or 10-membered bicyclic heteroaryl ring containing 1, 2 or 3 heteroatoms selected from nitrogen, oxygen and sulphur;

Q is a group of formula $L^1X^2L^2Z$ in which $L^1$ is a bond, (1–4C)alkylene or (2–4C)alkenylene, $L^2$ is a bond or (1–4C)alkylene, $X^2$ is a bond, O, S, SO, $SO_2$, $CR^8R^9$, CO, $OSO_2$, $OCR^8R^9$, OCO, $SO_2O$, $CR^8R^9O$, COO, $NR^{10}SO_2$, $SO_2NR^{11}$, $NR^{12}CO$, $CONR^{12}$, $NR^{13}CONR^{14}$ and $NR^{14}$ in which $R^8$ and $R^9$ are independently selected from hydrogen, hydroxy and (1–4C)alkyl; and $R^{10}$, $R^{11}$, $R^{12}$, $R^{13}$ and $R^{14}$ are independently selected from hydrogen and (1–4C)alkyl;

Z is hydrogen, (1–4C)alkyl, phenyl, naphthyl, phenyl (2–4C)alkenyl, phenyl(2–4C)alkynyl or a heterocyclic moiety containing 1, 2, 3 or 4 heteroatoms selected from nitrogen, oxygen and sulphur;

and wherein the phenyl, naphthyl or heteroaryl moiety in $Ar^1$ and the alkyl, phenyl, naphthyl, or heterocyclic moiety in Z may optionally bear one or more substituents selected from halogeno, hydroxy, amino, nitro, cyano, carboxy, carbamoyl, (1–6C)alkyl, (2–6C) alkenyl, (2–6C)alkynyl, hydroxy(1–6C)alkyl, (1–6C) alkoxy, (3–6C)cycloalkyl, (3–6C)cycloalkyl(1–4C) alkyl, (1–4C)alkylenedioxy, (1–6C)alkylamino, di-[(1–6C)alkyl]amino, N-(1–6C)alkylcarbamoyl, di-N [(1–6C)alkyl]carbamoyl, (1–6C)alkanoylamino, (1–6C)alkoxycarbonyl, (1–6C)alkylthio, (1–6C) alkylsulphinyl, (1–6C)alkylsulphonyl, halogeno(1–6C) alkyl, halogeno(1–6C)alkoxy, (1–6C)alkanoyl, tetrazoyl, phenyl, phenoxy, phenylsulphonylpiperidinocarbonyl, morpholinocarbonyl, hydroxy(1–6C)alkyl and amino (1–6C)alkyl; wherein any phenyl containing substituents may optionally bear one or more substituents selected from halogeno, trifluoromethyl, trifluoromethoxy, cyano, amino, hydroxy, nitro, (1–4C) alkyl, (1–4C)alkoxy, (1–4C)alkylamino and di(1–4C) alkylamino;

provided that the compound is not N-[4-[4-(4-pyridyl) piperazin-1-ylcarbonyl]phenyl]-(E)-4-chlorostyrenesulphonamide or N-[4-[4-(4-pyridyl) piperazin-1-ylcarbonyl]phenyl]-4'-bromo-4-biphenylesulphonamide;

and pharmaceutically acceptable salts thereof.

2. A compound as claimed in claim 1 wherein there is provided a compound of formula I, or a pharmaceutically acceptable salt thereof, wherein $G^1$ is CH;

$G^2$ is CH;

n is 1 or 2;

R is hydrogen, halogeno, trifluoromethyl, trifluoromethoxy, cyano, amino, hydroxy, nitro, (1–4C) alkyl, (1–4C)alkoxy, (1–4C)alkylamino or di(1–4C) alkylamino;

A is methylene or ethylene; B is ethylene; and wherein A and B may independently optionally bear a substituent selected from (1–6C)alkyl, (1–6C)alkoxy, phenyl (1–4C)alkyl, halogeno and (1–6C)alkoxycarbonyl;

T is N;

$X^1$ is selected from $SO_2$, SO, CO and $CR^3R^4O$, wherein $R^3$ and $R^4$ are independently selected from hydrogen and (1–4C)alkyl;

$Y^1$ represents $CR^6R^7$, wherein $R^6$ and $R^7$ are independently selected from hydrogen and (1–4C)alkyl;

$Ar^1$ is a phenylene ring or a 5- or 6-membered monocyclic heteroaryl ring containing 1, 2 or 3 heteroatoms selected from nitrogen, oxygen and sulphur;

Q is a group of formula $L^1X^2L^2Z$ in which $L^1$ is a bond or (1–4C)alkylene, $L^2$ is a bond or (1–4C)alkylene, $X^2$ is a bond, S, SO, $SO_2$, $CR^8R^9$, CO, $NR^{10}SO_2$, $SO_2NR^{11}$, $NR^{12}CO$, $CONR^{12}$ and $NR^{13}CONR^{14}$ in which $R^8$, $R^9$, $R^{10}$, $R^{11}$, $R^{12}$, $R^{13}$ and $R^{14}$ are independently selected from hydrogen and (1–4C)alkyl;

Z is selected from phenyl, naphthyl, phenyl(2–4C) alkenyl, phenyl(2–4C)alkynyl and a heterocyclic moiety containing 1, 2, 3 or 4 heteroatoms selected from nitrogen, oxygen and sulphur;

and wherein the phenyl or heteroaryl moiety in $Ar^1$ and the phenyl, naphthyl, or heterocyclic moiety in Z may optionally bear one or more substituents selected from halogeno, hydroxy, amino, nitro, cyano, carboxy, carbamoyl, (1–6C)alkyl, (2–6C)alkenyl, (2–6C)alkynyl, (1–6C)alkoxy, (3–6C)cycloalkyl, (3–6C)cycloalkyl(1–4C)alkyl, (1–4C)alkylenedioxy, (1–6C)alkylamino, di-[(1–6C)alkyl]amino, N-(1–6C)alkylcarbamoyl, di-N[(1–6C)alkyl]carbamoyl, (1–6C)alkanoylamino, (1–6C)alkoxycarbonyl, (1–6C)alkylthio, (1–6C)alkylsulphinyl, (1–6C)alkylsulphonyl, halogeno(1–6C)alkyl, halogeno(1–6C)alkoxy, (1–6C)alkanoyl and tetrazoyl;

provided that the compound is not N-[4-[4-(4-pyridyl)piperazin-1-ylcarbonyl]phenyl]-(E)-4-chlorostyrenesulphonamide, and pharmaceutically acceptable salts thereof.

3. A compound as claimed in claim 1 wherein $X^1$ is CO or $SO_2$.

4. A compound as claimed in claim 1 wherein R and n are as defined in claim 1 and $X^1$, A, B and $Ar^1$ are selected from:
(a) $X^1$ is $SO_2$ or CO; A and B are both ethylene; $Ar^1$ is a phenyl ring;
(b) $X^1$ is $SO_2$ or CO, A and B are ethylene, $Ar^1$ is a phenyl ring and;
(e) $X^1$ is $SO_2$ or CO, A and B are ethylene, $Ar^1$ is a pyridyl ring.

5. A compound as claimed in claim 1 wherein $X^1$ is CO or $SO_2$, A and B are ethylene, and $Ar^1$ is phenyl.

6. A compound as claimed in claim 1 wherein Q is a group of formula $L^1X^2L^2Z$.

7. A compound as claimed in claim 1 wherein R and n are as defined in claim 1 and A, B, $X^1$, $Y^1$, and Q are selected from:
(a) A is ethylene, or methylene, B is ethylene, Q is a group of formula $L^1X^2L^2Ar^2$ in which $L^1$ is (1–4C)alkylene or a bond, $X^2$ is selected from $CONR^{12}$, $NR^{12}CO$, $NR^{10}SO_2$, $NR^{13}CONR^{14}$ and $SO_2$, L is a (1–4C) alkylene or a bond, $R^{10}$, $R^{12}$, $R^{13}$ and $R^{14}$ are independently selected from hydrogen and (1–4C)alkyl;
(b) A and B are ethylene, Q is a group of formula $L^1X^2L^2Ar^2$ in which $L^1$ is (1–4C)alkylene or a bond, $X^2$ is NHCO, $NHSO_2$, NHCONH or $SO_2$, $L^2$ is (1–4C) alkylene or a bond, and R and n are as hereinbefore defined;
(c) A and B are ethylene, Q is $L^1X^2L^2Ar^2$ in which $L^1$ is (1–4C)alkylene, $L^2$ is a bond, $X^2$ is NHCO, $NHSO_2$, NHCONH and $SO_2$; or
(d) A and B are ethylene, $Ar^1$ is phenyl, Q is a group of formula $L^1X^2L^2Ar^2$ in which $L^1$ is (1–4C)alkylene or a bond, $X^2$ is NHCO, $NHSO_2$, NHCONH or $SO_2$, $L^2$ is (1–4C)alkylene or a bond.

8. A compound as claimed in claim 1 wherein A and B are ethylene, $Ar^1$ is phenyl, Q is of formula $L^1X^2L^2Z$ in which $L^1$ is (1–4C)alkylene, $X^2$ is $NR^6SO_2$ in which $R^6$ is (1–4C) alkyl or hydrogen, and Z is phenyl, wherein the phenyl moiety of $Ar^1$ and Z may optionally be substituted as defined in claim 1 and R and n are as defined in claim 1.

9. A compound of the formula I as claimed in claim 1 wherein $Ar^1$ is a phenylene ring, a pyridyl ring, or a fused heterocyclic system containing 1, 2 or 3 heteroatoms, and may optionally bear one or more substituents selected from halogeno, nitro, cyano, (1–6C) alkyl, (1–6C)alkylthio, halogeno(1–6C)alkyl, halogeno(1–6C)alkylthio, halogeno(1–6C)alkoxy, (1–6C) alkoxycarbonyl, Q is a group of formula $L^1X^2L^2Ar^2$ in which $L^1$ is a bond or (1–4C)alkylene, $L^2$ is a bond or (1–4C)alkylene, $X^2$ is a bond, $NR^8$, O or S, in which $R^8$ is hydrogen or (1–4)C alkyl; and $Ar^2$ is selected from phenyl, and a monocyclic heterocyclic moiety containing 1, 2, 3 or 4 heteroatoms selected from nitrogen, oxygen and sulphur, and may optionally bear one or more substituents selected from halogeno, nitro, cyano, (1–6C)alkyl, (1–6C)alkylthio, halogeno (1–6C)alkyl, halogeno(1–6C)alkylthio, halogeno (1–6C)alkoxy, (1–6C)alkoxycarbonyl.

10. A compound as claimed in claim 1 wherein $Ar^1$ is a phenylene ring, a 2-pyridyl ring, a benzthiazol-2yl ring, a 2-quinoyloxy ring, a benzoxazolyl ring, a thiazolopyridin-2-yl or a quinoxalinyloxy ring.

11. A compound as claimed in claim 1 wherein R is hydrogen, halogeno or (1–4C)alkyl.

12. A compound as claimed in claim 1 wherein the substituent Q on $Ar^1$ is in the 4-position.

13. A compound as claimed in claim 1 wherein the substituent(s) on $Ar^1$ and/or $Ar^2$ are independently selected from methyl, methylthio, cyano, nitro, trifluoromethyl, trifluoromethoxy, trifluoromethylthio, chlorine, bromine, fluorine and methoxycarbonyl.

14. A process for preparing a compound of formula I, or a pharmaceutically acceptable salt thereof, as claimed in claim 1 which process is selected from:
(a) for the production of those compounds of the formula I wherein T is N and $X^1$ is CO, the reaction, conveniently in the presence of a suitable base, of an amine of the formula II,

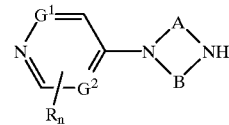

II with an acid of the formula III,

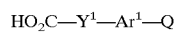

$HO_2C—Y^1—Ar^1—Q$   III or a reactive compound thereof;

(d) The reaction of an amine of formula II with a compound of formula VII,

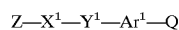

$Z—X^1—Y^1—Ar^1—Q$   VII wherein Z' is a displaceable group;

(e) the reaction of a compound of formula VIII

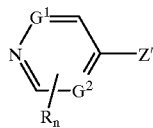   VIII wherein Z' is a displaceable group with a compound of formula IX

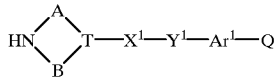   IX (f) for the production of those compounds of the formula I wherein $X^2$ is a group of the formula $NR^{10}SO_2$, the reaction of an amine of the formula X

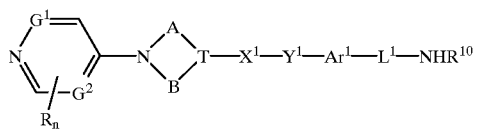   X with a compound of the formula XI,

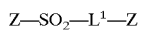   XI wherein Z' is a displaceable group;

(g) for the production of those compounds of the formula I wherein $X^2$ is a group of the formula $NR^{13}CONR^{14}$, the reaction, of an amine of the formula X, with a compound of the formula XII;

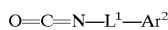   XII (h) for the production of those compounds of the formula I wherein $X^2$ is a group of the formula $NR^{10}SO_2$ and $R^{10}$ represents (1–4C)alkyl, the reaction of a corresponding sulphonamide of the formula XIII,

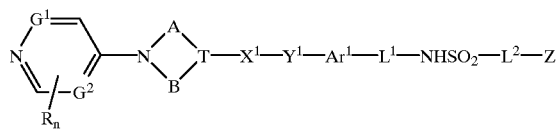   XIII with a compound of the formula XIV,

   XIV wherein Z' is a displaceable group;

(i) for the production of those compounds of the formula I wherein $L^1$ represents (1–4C)alkylene and $X^2$ is S, the reaction of a compound of the formula XV,

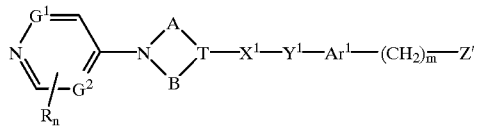   XV wherein m is 1, 2, 3 or 4, and Z' is a displaceable group with a thiol of the formula XVI;

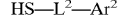   XVI (j) for the production of those compounds of the formula I wherein $Ar^1$ or Z bears a carboxy or carboxy-containing group, the hydrolysis of a compound of the formula I wherein $Ar^1$ or Z bears a (1–6C) alkoxycarbonyl group, (k) for the production of those compounds of the formula I wherein $Ar^1$ or Z bears a carbamoyl, N-(1–6C) alkylcarbamoyl or alkyldi-N[(1–6C)carbamoyl group, the reaction of a compound of the formula I wherein $A^1$ or Z bears a carboxy group, or a reactive compound thereof, with ammonia or an appropriate alkylamine or dialkylamine, (l) for the production of those compounds of the formula I wherein $X^1$ is a group of the formula SO or $SO_2$ wherein $Ar^1$ or Z bears a (1–6C)alkylsulphinyl or (1–6C)alkylsulphonyl, substituent or wherein $X^2$ is a group of the formula SO or $SO_2$, the oxidation of the corresponding compound of the formula I which contains a thio group; and whereafter when a pharmaceutically acceptable salt is required reacting the compound of formula I with an acid which affords a physiologically acceptable anion or a base which affords a physiologically acceptable cation.

15. A pharmaceutical composition comprising a compound of formula I, or a pharmaceutically acceptable salt thereof, as defined in any one of claims 1 to 13, together with a pharmaceutically acceptable carrier or diluent.

16. A method for treating diseases or medical conditions in which an inhibition of cholesterol biosynthesis is desirable comprising administering a compound of formula I, or a pharmaceutically acceptable salt thereof, as claimed in any one of claims 1 to 13.

17. A method for the treatment of hypercholesterolemia or atherosclerosis comprising administering a compound of formula I, or a pharmaceutically acceptable salt thereof, as claimed in any one of claims 1 to 8.

* * * * *